United States Patent
Rafiee et al.

(10) Patent No.: US 10,433,962 B2
(45) Date of Patent: Oct. 8, 2019

(54) ANNULOPLASTY PROCEDURES, RELATED DEVICES AND METHODS

(71) Applicants: Nasser Rafiee, Andover, MA (US); Stuart MacDonald, Andover, MA (US); Koosha Rafiee, Andover, MA (US); Rany Busold, Andover, MA (US); Robert J. Lederman, Chevy Chase, MD (US); Toby Rogers, Bethesda, MD (US)

(72) Inventors: Nasser Rafiee, Andover, MA (US); Stuart MacDonald, Andover, MA (US); Koosha Rafiee, Andover, MA (US); Rany Busold, Andover, MA (US); Robert J. Lederman, Chevy Chase, MD (US); Toby Rogers, Bethesda, MD (US)

(73) Assignees: Transmural Systems LLC, Andover, MA (US); The United States of America, as Represented by the Secretary, Department of Health and Human Services, Bethesda, MD (US)

(*) Notice: Subject to any disclaimer, the term of this patent is extended or adjusted under 35 U.S.C. 154(b) by 0 days.

(21) Appl. No.: 15/796,344

(22) Filed: Oct. 27, 2017

(65) Prior Publication Data
US 2018/0098850 A1 Apr. 12, 2018

Related U.S. Application Data

(63) Continuation-in-part of application No. PCT/US2017/031543, filed on May 8, 2017.
(Continued)

(51) Int. Cl.
*A61F 2/24* (2006.01)
*A61M 25/01* (2006.01)
(Continued)

(52) U.S. Cl.
CPC .......... *A61F 2/2451* (2013.01); *A61F 2/2466* (2013.01); *A61M 25/01* (2013.01);
(Continued)

(58) Field of Classification Search
CPC ..... A61F 2/2442; A61F 2/2451; A61F 2/2466
See application file for complete search history.

(56) References Cited

U.S. PATENT DOCUMENTS 4,917,698 A 4/1990 Carpentier et al.
5,041,130 A 8/1991 Cosgrove et al.
(Continued)

FOREIGN PATENT DOCUMENTS

EP 1 022 022 11/1999
EP 2742912 A2 6/2014
(Continued)

OTHER PUBLICATIONS

Alfieri, et al., "Future of transcatheter repair of the mitral valve", Abstract Only.*American Journal of Cardiology*, vol. 96, No. 12A, pp. 71L-75L, 2005.
(Continued)

*Primary Examiner* — Christopher D. Prone
(74) *Attorney, Agent, or Firm* — Crawford Maunu PLLC

(57) ABSTRACT

Devices and methods are disclosed for the treatment or repair of regurgitant cardiac valves, such as a mitral valve. An illustrative annuloplasty device can be placed in the coronary sinus to reshape the mitral valve and reduce mitral valve regurgitation. An improved protective device can be placed between the annuloplasty device and an underlying coronary artery to inhibit compression of the underlying coronary artery by the annuloplasty device in the coronary sinus. In addition, the protective device can inhibit compression of the coronary artery from inside the heart, such as from a prosthetic mitral valve that exerts radially outward (Continued)

pressure toward the coronary artery. The annuloplasty device can also create an artificial inner ridge or retaining feature projecting into the native mitral valve region to help secure a prosthetic mitral valve.

17 Claims, 62 Drawing Sheets

Related U.S. Application Data

(60) Provisional application No. 62/332,754, filed on May 6, 2016.

(51) Int. Cl.
  *A61B 17/04* (2006.01)
  *A61B 17/32* (2006.01)
  *A61B 17/3201* (2006.01)

(52) U.S. Cl.
  CPC ....... *A61B 17/0467* (2013.01); *A61B 17/3201* (2013.01); *A61B 17/320016* (2013.01); *A61F 2230/0045* (2013.01); *A61F 2250/0065* (2013.01); *A61M 2025/0175* (2013.01)

(56) References Cited

U.S. PATENT DOCUMENTS

| | | | |
|---|---|---|---|
| 5,061,277 A | 10/1991 | Carpentier et al. | |
| 5,064,431 A | 11/1991 | Gilbertson et al. | |
| 5,104,407 A | 4/1992 | Lam et al. | |
| 5,201,880 A | 4/1993 | Wright et al. | |
| 5,290,300 A | 3/1994 | Cosgrove et al. | |
| 5,350,420 A | 9/1994 | Cosgrove et al. | |
| 5,476,528 A | 12/1995 | Trimm et al. | |
| 5,888,015 A | 3/1999 | Brown et al. | |
| 5,972,030 A | 10/1999 | Garrison et al. | |
| 6,402,781 B1 | 6/2002 | Langberg et al. | |
| 6,485,760 B2 | 11/2002 | Matsuyama | |
| 6,716,459 B2 | 4/2004 | Matsuyama | |
| 6,726,716 B2 | 4/2004 | Marquez | |
| 7,073,511 B2 | 7/2006 | Schroeppel | |
| 7,090,695 B2 | 8/2006 | Solem et al. | |
| 8,211,171 B2 | 7/2012 | Kim et al. | |
| 8,231,671 B2 | 7/2012 | Kim | |
| 8,632,588 B2 | 1/2014 | Kim | |
| 9,271,833 B2 | 3/2016 | Kim et al. | |
| 9,743,922 B2 | 8/2017 | Kim et al. | |
| 9,943,409 B2 | 4/2018 | Kim et al. | |
| 2002/0128701 A1 | 9/2002 | Winters | |
| 2002/0198591 A1 | 12/2002 | Stergiopulos | |
| 2003/0078465 A1 | 4/2003 | Pai et al. | |
| 2003/0083538 A1 | 5/2003 | Adams et al. | |
| 2003/0130731 A1 | 7/2003 | Vidlund et al. | |
| 2004/0098116 A1 | 5/2004 | Callas et al. | |
| 2004/0102840 A1 | 5/2004 | Solem et al. | |
| 2004/0133273 A1 | 7/2004 | Cox | |
| 2004/0220657 A1 | 11/2004 | Nieminen et al. | |
| 2004/0254600 A1 | 12/2004 | Zarbatany et al. | |
| 2005/0027351 A1 | 2/2005 | Reuter et al. | |
| 2005/0027353 A1 | 2/2005 | Alferness et al. | |
| 2005/0038506 A1 | 2/2005 | Webler et al. | |
| 2005/0137451 A1 | 6/2005 | Lucas et al. | |
| 2005/0216039 A1 | 9/2005 | Lederman | |
| 2005/0222488 A1 | 10/2005 | Chang et al. | |
| 2006/0106279 A1 | 5/2006 | Machold et al. | |
| 2006/0184242 A1 | 8/2006 | Lichtenstein | |
| 2007/0027392 A1 | 2/2007 | Schwartz | |
| 2007/0073391 A1 | 3/2007 | Bourang et al. | |
| 2007/0118151 A1 | 5/2007 | Davidson | |
| 2007/0123978 A1 | 5/2007 | Cox | |
| 2007/0135826 A1 | 6/2007 | Zaver et al. | |
| 2007/0208376 A1 | 9/2007 | Meng | |
| 2007/0276437 A1 | 11/2007 | Call et al. | |
| 2008/0004697 A1 | 1/2008 | Lichtenstein et al. | |
| 2008/0125848 A1 | 5/2008 | Kusleika et al. | |
| 2008/0228198 A1 | 9/2008 | Traynor et al. | |
| 2008/0228267 A1 | 9/2008 | Spence et al. | |
| 2010/0114299 A1 | 5/2010 | Ben Muvhar et al. | |
| 2011/0054597 A1 | 3/2011 | Kim | |
| 2011/0112632 A1 | 5/2011 | Chau et al. | |
| 2011/0313434 A1 | 12/2011 | Kocaturk | |
| 2012/0029629 A1 | 2/2012 | Kim | |
| 2012/0232574 A1 | 9/2012 | Kim et al. | |
| 2013/0211510 A1 | 8/2013 | Lederman et al. | |
| 2015/0157459 A1 | 6/2015 | Macoviak et al. | |
| 2015/0342600 A1 | 12/2015 | Kim et al. | |
| 2016/0081798 A1 | 3/2016 | Kocaturk | |
| 2016/0193043 A1 | 7/2016 | Kim | |
| 2017/0119489 A1 | 5/2017 | Kim | |
| 2017/0150964 A1 | 6/2017 | Kim | |
| 2017/0209686 A1 | 7/2017 | Kim | |

FOREIGN PATENT DOCUMENTS

| | | |
|---|---|---|
| RU | 134785 | 11/2013 |
| WO | WO 95/006447 | 3/1995 |
| WO | WO 01/054618 | 8/2001 |
| WO | WO 02/100240 | 12/2002 |
| WO | WO 03/037171 | 5/2003 |
| WO | WO 04/045378 | 6/2004 |
| WO | WO 2005/046520 | 5/2005 |
| WO | WO 06/116129 | 11/2006 |
| WO | WO 06/132880 | 12/2006 |
| WO | 2007030417 A2 | 3/2007 |
| WO | 2008042229 A2 | 4/2008 |
| WO | 2008060553 | 5/2008 |
| WO | 2008089044 | 7/2008 |
| WO | 20120243898 | 4/2012 |
| WO | 2014191924 | 12/2014 |
| WO | 2015005690 A1 | 1/2015 |
| WO | 2015028986 A1 | 3/2015 |
| WO | 2015167194 A1 | 11/2015 |
| WO | 2015178612 A1 | 11/2015 |
| WO | 2015194754 A1 | 12/2015 |
| WO | 2016013763 A1 | 1/2016 |
| WO | 2016013765 A1 | 1/2016 |
| WO | 2016024710 A1 | 2/2016 |
| WO | 2016032177 | 3/2016 |

OTHER PUBLICATIONS

Block,"Percutaneous transcatheter repair for mitral regurgitation",Abstract Only, *Journal of Interv. Cardiology*, vol. 6,pp.547-551,2006.

Chinzei,et al.,"MR Compatibility of Mechatronic Devices: Design Criteria",*Int. Conj Med. Image Comput. Assita Interv.*, vol. 2,pp. 1020-1031,1999.

De Silva,et al.,"X-Ray Fused With Magnetic Resonance Imaging (XFM) to Target Endomyocarial Injections",*Circulation*, vol. 114,pp. 1342-2350,2006.

Mack,"New Techniques for percutaneous repair of the mitral valve",*Heart Fail. Rev.*, vol. 11,pp. 259-268,2006, Abstract Only.

Maniu,et al.,"Acute and chronic reduction of functional mitral regurgitation in experimental heart failure by percutaneous mitral annuloplasty", *Journal of American Coll. Cardiol.*, vol. 44,No. 8,pp. 1652-1661,2004.

Maselli,et al.,"Percutaneous Mitral Annuloplasty: An Anatomic Study of Human Coronary Sinus and Its Relation With Mitral Valve Annulus and Coronary Arteries", *Circulation*, vol. 114,pp. 377-380,2006.

Webb,et al.,"Percutaneous Transvenous Mitral Annuloplasty: Initial Human Experience With Device Implantation in the Coronary Sinus",*Circulation*, vol. 113,pp. 851-855,2006.

International Search Report and Written Opinion for International Application No. PCT/US2017/017367, 8 pages, dated May 25, 2017.

Federal Institute of Industrial Property/RU Search Authority. International Search Report and Written Opinion dated Aug. 24, 2017, regarding related International Patent Application No. PCT/US2017/031543, 9 pages.

(56) References Cited

OTHER PUBLICATIONS

June-Hong Kim et al. "Mitral Cerclage Annuloplasty, A Novel Transcatheter Treatment for Secondary Mitral Valve Regurgitation." Journal of the American College of Cardiology, vol. 54, No. 7, pp. 638-651 (2009).

International Preliminary Report on Patentability dated Nov. 15, 2018, for corresponding Int'l Patent Application No. PCT/US2017/031543.

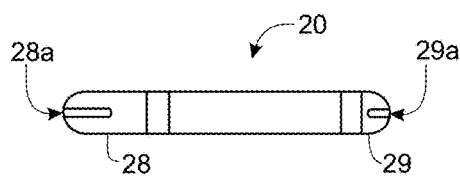
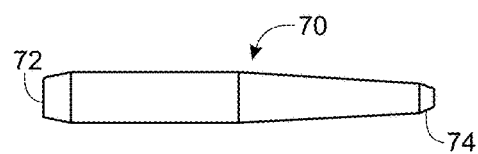
FIG. 1C    FIG. 1F
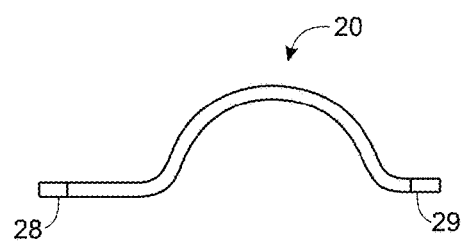
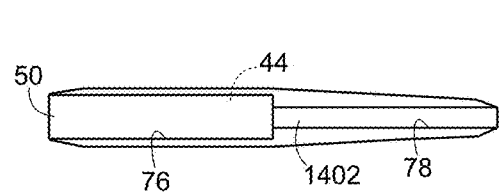
FIG. 1D    FIG. 1G
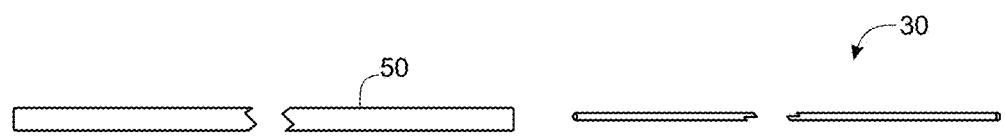
FIG. 1E    FIG. 1H

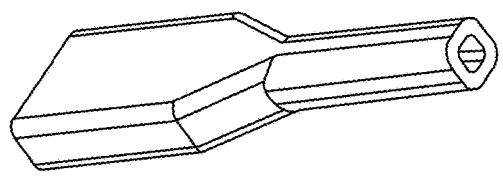
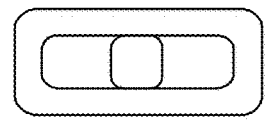
FIG. 1AE              FIG. 1AF
FIG. 1AG              FIG. 1AH
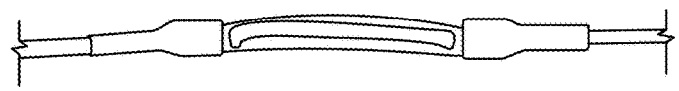
FIG. 1AI
FIG. 1AJ

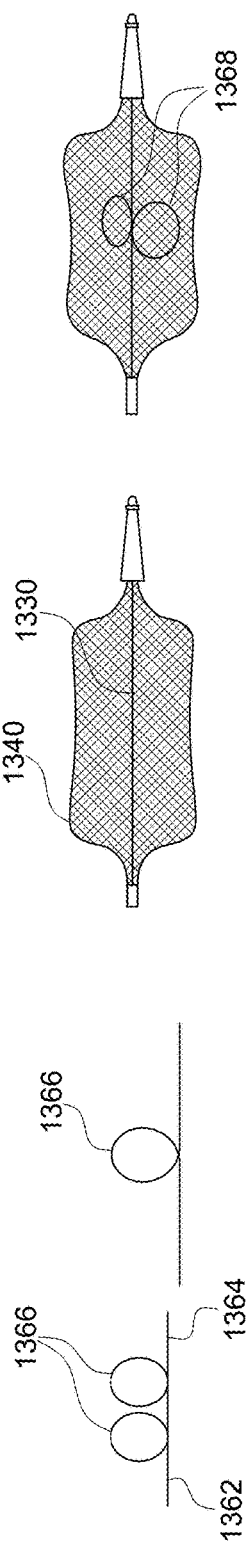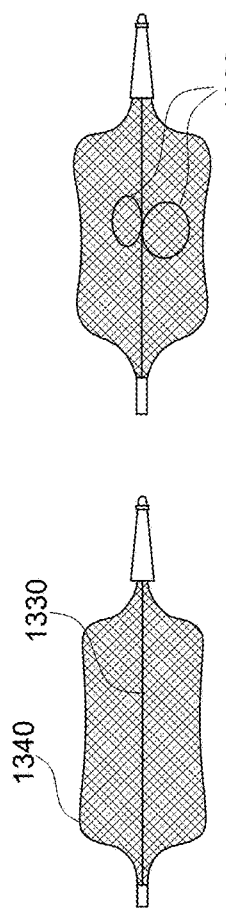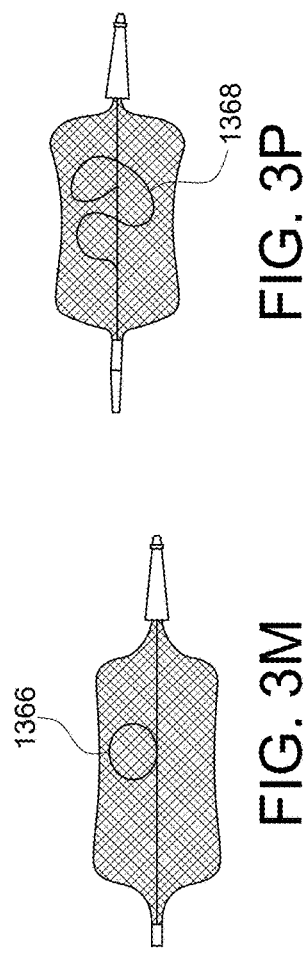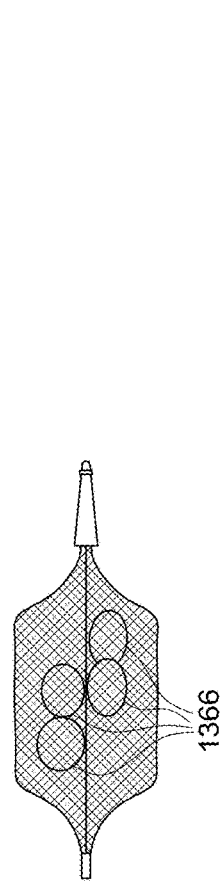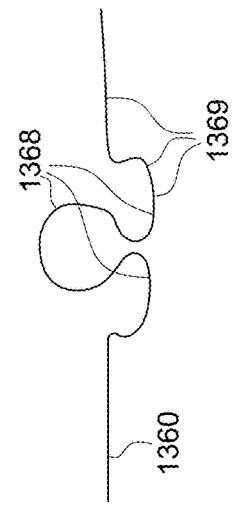

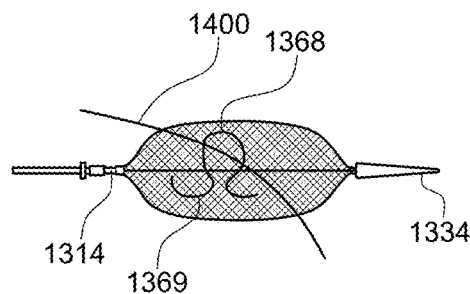 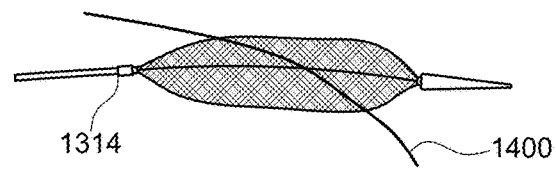
FIG. 3Q    FIG. 3R
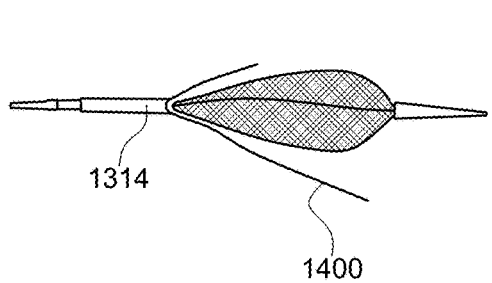 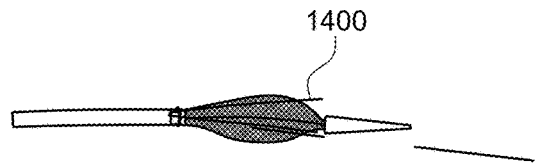
FIG. 3S    FIG. 3T
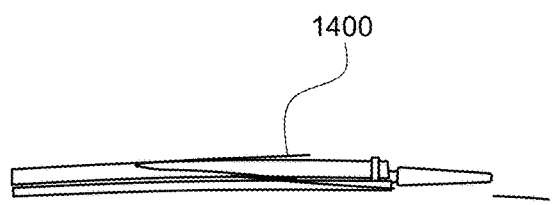
FIG. 3U

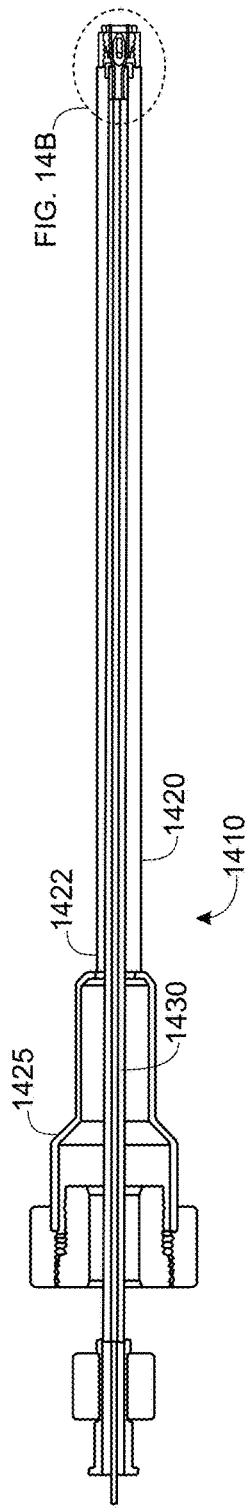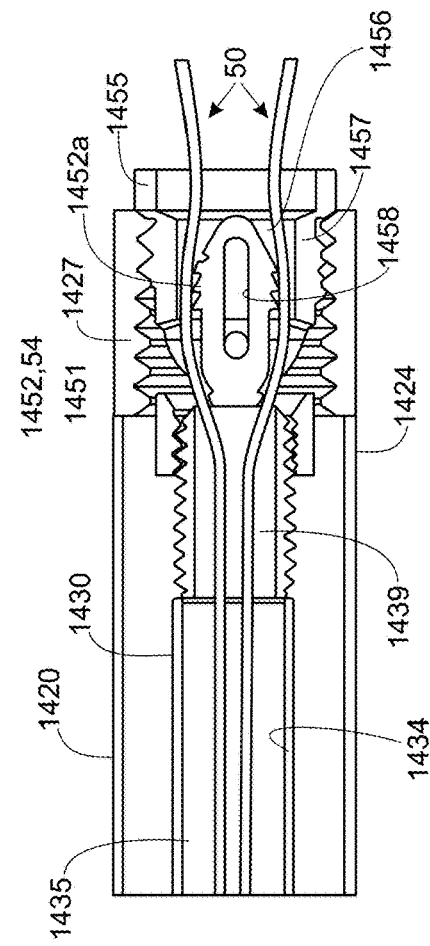
FIG. 14A
FIG. 14B

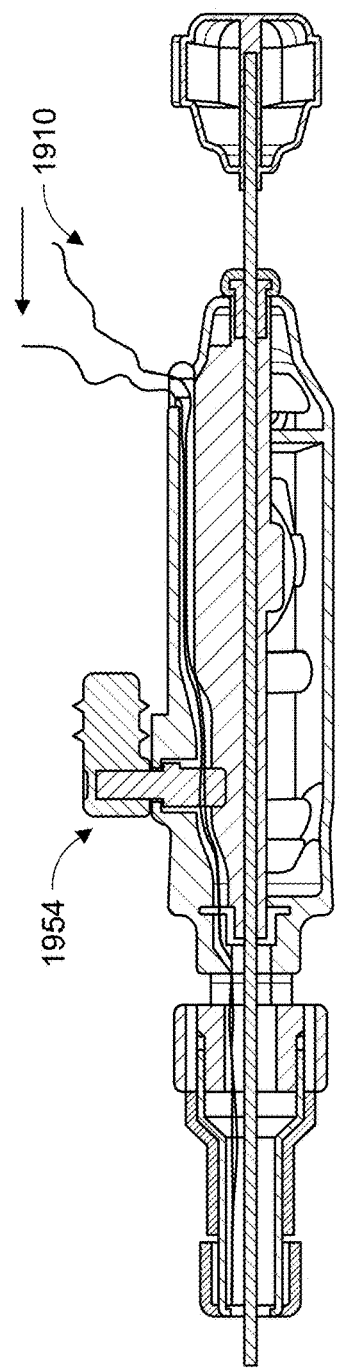

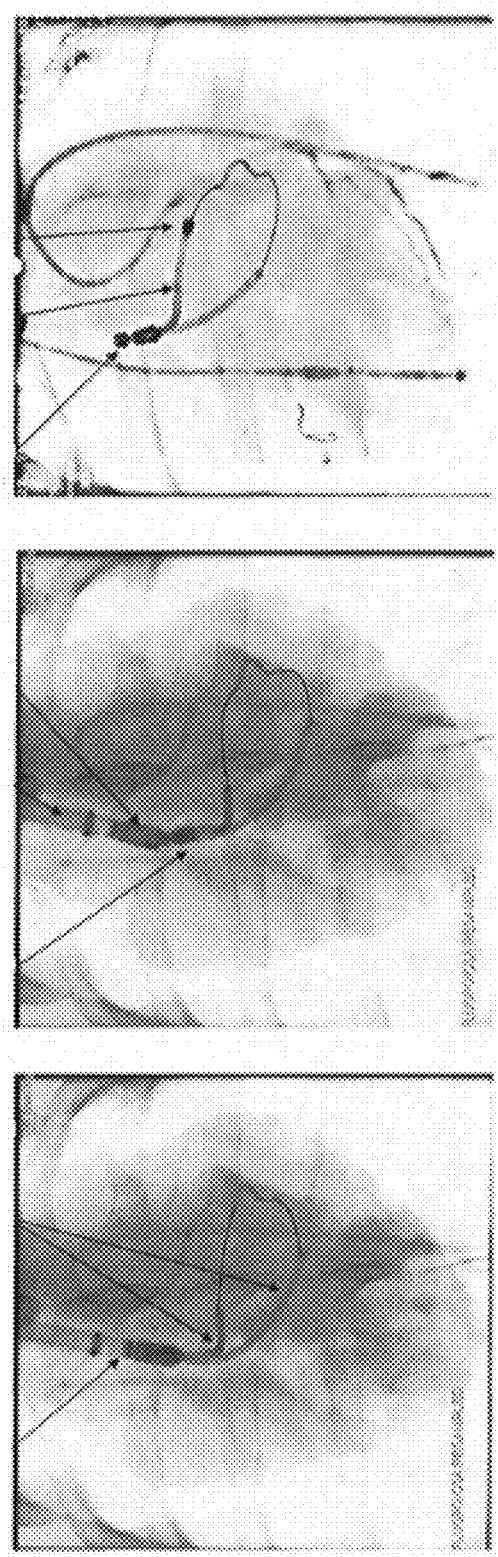

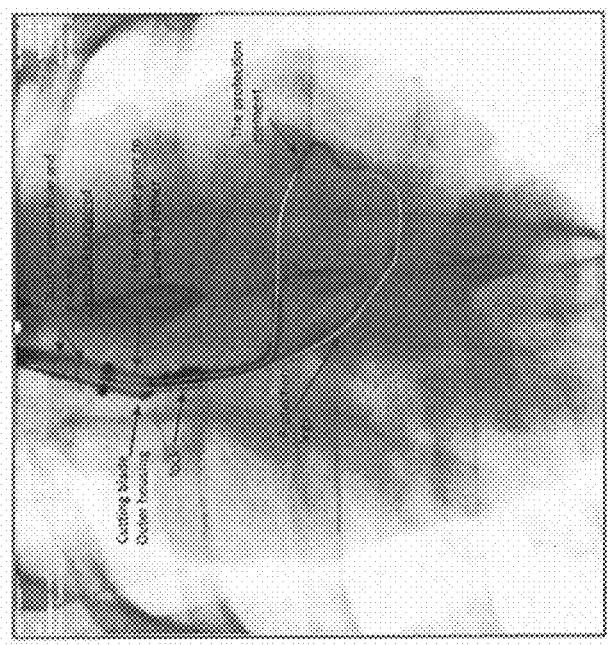
FIG. 22G
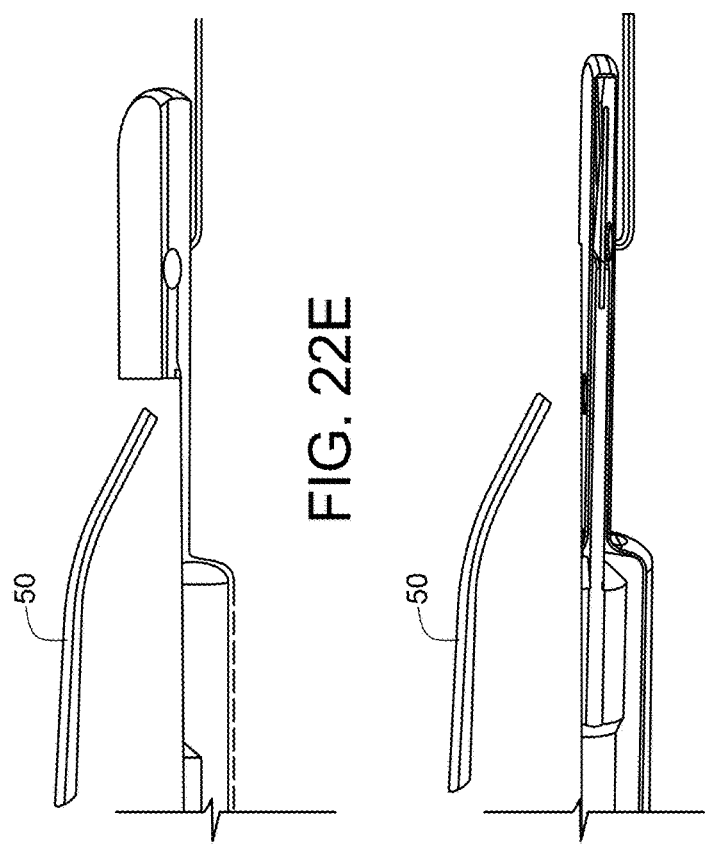
FIG. 22E
FIG. 22F

ANNULOPLASTY PROCEDURES, RELATED DEVICES AND METHODS

CROSS-REFERENCE TO RELATED APPLICATIONS

The present patent application is a continuation-in-part of and claims the benefit of priority to International Application No. PCT/US2017/031543, filed May 8, 2017, which in turn claims the benefit of priority to U.S. Provisional Patent Application Ser. No. 62/332,754, filed May 6, 2016. The disclosure of each of the foregoing patent applications is expressly incorporated by reference herein for any purpose whatsoever.

FIELD OF THE DISCLOSURE

The present disclosure relates to annuloplasty techniques and devices in which tensioning elements (e.g., tethers) are placed in the coronary sinus to perform mitral valve annuloplasty and treat mitral valve regurgitation.

BACKGROUND

Mitral valve regurgitation is a common cardiac valve disorder that can be caused by a primary valvular problem (such as damaged valve leaflets) or functional problems that impair leaflet coaptation. A common cause of functional mitral valve regurgitation is dilated cardiomyopathy caused by myocardial infarction, chronic myocardial ischemia, hypertension, myocarditis, or other causes of heart muscle injury. Enlargement of the mitral annulus and left ventricular cavity produce mitral valvular insufficiency that can cause volume overload that further exacerbates the underlying myopathy and worsens the valvular insufficiency. Mitral valve repair can reduce mitral regurgitation and correct secondary mitral annular dilation to thereby improve mitral valve leaflet coaptation. One such repair technique is an annuloplasty procedure, in which the annulus of the valve is surgically reconstructed or augmented by placement of a ring around the valve annulus to reduce its circumferential and septal-lateral dimensions. In patients with congestive heart failure and secondary mitral regurgitation, annuloplasty can provide a long-term symptomatic and survival benefit.

Traditional mitral valve annuloplasty requires open heart surgery with a sternotomy or thoracotomy and cardiac arrest and cardio-pulmonary bypass. For example, the annuloplasty procedure is performed through a surgical incision in which the effective size of the valve annulus is reduced by attaching a prosthetic annuloplasty ring to the left atrial aspect of the mitral valve annulus. A variety of rigid and flexible annuloplasty rings have been developed for this purpose, such as those shown in U.S. Pat. Nos. 4,917,698; 5,041,130; 5,061,277; 5,064,431; 5,104,407; 5,201,880; and 5,350,420. Although very effective, this open-heart procedure is accompanied by substantial morbidity and prolonged convalescence. As a result, the procedure often is not offered to patients who are insufficiently symptomatic to justify the surgical risk and morbidity, or to patients who suffer advanced disease, or to patients with substantial co-morbidity.

Percutaneous approaches to mitral valve repair have been developed to reduce the clinical disadvantages of the open-heart procedures. In some percutaneous techniques, a prosthesis is advanced in a catheter through the subject's vasculature to the vicinity of the mitral valve. These percutaneous techniques are attractive alternatives to conventional surgical treatment because they do not require open heart surgery or extracorporeal circulation, and they can be used in a closed and beating heart. The treatment is potentially less morbid and can be applied to a wider range of patients including those with less severe valvular dysfunction.

Examples of percutaneous mitral valve repair procedures include coronary-sinus shortening devices, transcameral fixtures, endoventricular annular plication, and direct leaflet stapling. Coronary sinus annuloplasty techniques have been disclosed, for example, in U.S. Pat. Nos. 6,402,781 and 7,090,695, as well as U.S. Patent Publication Nos. 2004/0254600; 2005/0027351; and 2007/0073391. Some trans-sinus approaches aim to improve mitral valve coaptation by introducing a prosthesis into the coronary sinus to exert forces that reduce the circumference of the posterior mitral annulus or move the posterior annulus toward the anterior leaflet. Coronary sinus methods take advantage of the proximity of the coronary sinus to the mitral valve annulus, such that the pressure of the prosthesis in the coronary sinus pushes the fibrous annulus or the nearby atrial wall inward to reduce the diameter of the annulus.

However, these techniques have shown only limited success in establishing circumferential tension that characterizes effective surgical ring annuloplasty. The sinus-shortening devices have induced only local shortening across the mitral commissures but do not adequately reduce the septal-lateral separation that characterizes functional mitral valve regurgitation. The leaflet procedures have not been able to reduce annular dilation and they can also impair the normal dynamic line of mitral valve coaptation that accommodates a range of volumes and inotropic states.

A more recent improvement of percutaneous annuloplasty is coronary sinus transcatheter-mitral-valve cerclage annuloplasty in which a tensioning material is placed around the mitral valve annulus using a catheter, such as a steerable guide wire or cannulation catheter. Certain cerclage trajectories can compensate for coronary sinus anatomy that is remote from the mitral valve annulus, by rotating the plane of circumferential tension toward the left ventricular outflow tract. In cerclage, a continuous strand of tensioning material (such as suture material) is applied along a pathway that extends at least partially through the coronary sinus and then reenters the right side of the heart, for example by passing through a basal septal perforator vein and penetrating a small distance through septal myocardium. The tensioning material is placed with the assistance of imaging technologies that may include X-ray fluoroscopy, magnetic resonance imaging, intracavitary or external ultrasound, electroanatomic mapping, X-ray computed tomography or a combination (fusion) of any of these imaging technologies.

SUMMARY OF THE DISCLOSURE

Trans-sinus approaches that use the cerclage technique or other indwelling coronary sinus prostheses can have limiting drawbacks, however, because the coronary sinus and its branches have now been found to cross the outer diameter of major coronary arteries in a majority of humans. As a result, pressure applied by any prosthetic device in the coronary sinus (such as tension on the annuloplasty device) can compress the underlying coronary artery and induce myocardial ischemia or infarction. In particular, the coronary sinus usually extends superficial to the circumflex coronary artery and its marginal branches near the great cardiac vein, and trans-sinus annuloplasty thus transmits pressure sufficient to constrict or occlude the underlying coronary artery. Whether coronary obstruction occurs during coronary sinus annuloplasty depends on the spatial relationship between the coronary artery and vein.

In a majority of humans, the coronary vein crosses over the left circumflex artery, which has limited the usefulness of coronary sinus annuloplasty. Given the foregoing, there is a need for methods that avoid constricting coronary artery branches during trans-sinus annuloplasty. Such improved techniques are described, for example, in U.S. Pat. No. 9,271,833, and U.S. patent application Ser. No. 15/056,599, filed Feb. 29, 2016, each of which is incorporated by reference herein in its entirety for any purpose whatsoever. The present disclosure provides still further improvements in such techniques and related devices to enhance the reliability and efficacy of cerclage procedures.

Thus, improved devices and methods are described herein for protecting underlying myocardial structures such as myocardial tissue or coronary artery branches from constriction during trans-sinus mitral annuloplasty. The disclosed embodiments can protect a coronary vessel from compression during mitral annuloplasty in which an annuloplasty element, such as a tensioning device, extends at least partially through the coronary sinus over a coronary artery. The device typically includes an improved surgically sterile bridge configured for placement within the coronary sinus at a location where the coronary sinus passes over a coronary artery, so that the protection device provides a support for a mitral annuloplasty element, such as a compressive prosthesis, including a tension element when it is placed under tension. The protection device has an arch of sufficient rigidity and dimensions to support the tensioning element over the coronary artery, redistribute tension away from an underlying coronary artery, and inhibit application of pressure to the underlying artery, for example when an annuloplasty tension element is placed under tension during mitral annuloplasty.

In some examples, the bridge can span a linear distance at its base of from about 0.45 inches to about 0.65 inches, in any desired increment of 0.01 inches. The support can have a height from its base to the bottom of the center of the arch that is about 0.14 to about 0.17 inches high, in any desired increment of 0.001 inch. The protective device can be made of a shape memory material, such as nitinol or other suitable material.

In particular embodiments, the protective device includes an improved arch-shaped support, or bridge, interposed in the coronary sinus between the annuloplasty device and the coronary artery that is more reliably installed. In one implementation, the protective device can be an implant that includes a bridge having a proximal end, a distal end, and an arched portion defined between the proximal end and the distal end of the bridge, a proximal core wire having a distal end near the proximal end of the bridge and having a proximal end extending proximally therefrom, a distal core wire having a proximal end near the distal end of the bridge and having a distal end extending distally therefrom, and a sheath material surrounding and encasing the proximal core wire, bridge and distal core wire.

In accordance with further embodiments, the disclosure provides implementations of an implant including a bridge having a proximal end, a distal end, and an arched portion defined between the proximal end and the distal end of the bridge. The implants can further include an elongate inner tether coupled to the bridge. The inner tether preferably includes radiopaque material along some or all of its length. The implants can still further include an outer sheath material surrounding and encasing the bridge and elongate inner tether, similar to the preceding embodiments.

If desired, said implants can further include an encasement surrounding the arch and a portion of the elongate inner tether that is co-incident with the bridge. For example, the encasement can be a polymeric tube that is shrunk around the bridge and elongate inner tether. The elongate inner tether can traverse at least one opening defined through the bridge. The elongate inner tether can pass over a top of the arch, for example, and through an opening near each end of the bridge, and underneath the end portions of the bridge. The implants can include a strain relief section, which can be of varying durometer along its length. The strain relief section(s) can surround one or both ends of the bridge, wherein the elongate inner tether passes through each strain relief section. The implants are preferably provided with a selectively removable proximal push tube disposed within the outer sheath material, a distal end of the proximal push tube abutting a proximal end region of the bridge, wherein the inner elongate tether passes through a central lumen of the proximal push tube. The implants can still further include a selectively removable distal pull tube disposed within the outer sheath material, a proximal end of the distal push tube abutting a distal end region of the bridge, wherein the inner elongate tether passes through a central lumen of the distal push tube. The proximal push tube and distal pull tubes can each be made at least in part from polymeric material. In some implementations, the inner tether can include a radiopaque wire inserted therein along its length. If desired, the inner tether can include radiopaque material embedded therein along its length. The push and pull tubes are referred to elsewhere herein as delivery tubes. These tubes can be made from any suitable, preferably polymeric, material, such as Pebax® polymeric materials and the like, and may be provided with one or more hydrophobic or hydrophilic lubricious coatings as described elsewhere herein.

If desired, the sheath material can be a continuous tubular member having a proximal region that covers the proximal core wire and a distal region covering the distal core wire. The proximal region of the sheath material can be crimped to the proximal core wire by a crimp affixed about the proximal end of the proximal core wire. The distal region of the sheath material can be crimped to the distal core wire by a crimp affixed about the distal end of the distal core wire. The proximal region of the sheath material can be compressed against the proximal core wire by a suture wrap. The distal region of the sheath material can be compressed against the distal core wire by a suture wrap. The sheath material can be compressed against a distal region of the proximal core wire and the bridge by a suture wrapped around the structure. The sheath material can be compressed against a distal region of the proximal core wire and the bridge by a heat shrunk polymeric sleeve. The sheath material can be compressed against a proximal region of the distal core wire and the bridge by a suture wrap. The sheath material can be compressed against a proximal region of the distal core wire and the bridge by a heat shrunk polymeric sleeve. If desired, the distal end of the proximal core wire can overlap lengthwise with the proximal end of the bridge.

In some implementations, the distal end of the proximal core wire can be at least partially received within a groove or slot formed in the proximal end of the bridge. The distal end of the proximal core wire can be at least partially received within a tubular member attached to the proximal end of the bridge. The tubular member can be attached to the proximal end of the bridge in a slot or groove formed into the proximal end of the bridge. The distal end of the proximal core wire can be at least partially received within a hole formed into the proximal end of the bridge. The proximal end of the distal core wire can overlap lengthwise with the distal end of the bridge, if desired. The proximal end of the distal core wire can be at least partially received within a groove or slot formed in the distal end of the bridge. If desired, the proximal end of the distal core wire can be at least partially received within a tubular member attached to the distal end of the bridge. The tubular member can be attached to the distal end of the bridge in a slot or groove formed into the distal end of the bridge. The proximal end of the distal core wire can be at least partially received within a hold formed into the distal end of the bridge. The proximal end and distal end of the bridge can be rounded to reduce trauma to surrounding tissue. The proximal end and distal end of the bridge can extend longitudinally outwardly along a longitudinal axis defined by the implant. The proximal and distal ends of the bridge can be planar, or any other suitable shape.

The core wires can be held in place with respect to the bridge by way of an interference fit, or may fit more loosely. The interference fit can be at least partially attributable to tension imparted by the sheath material, and/or friction between the core wires and a portion of the bridge. The sheath material can be formed from a plurality of braided fibers, and can be a hollow core suture material. The sheath material can includes radiopaque material. For example, the sheath material can include radiopaque fibers. The sheath material can include UHMWPE fibers. The implant can further include at least one crimp attaching the sheath material to at least one of the core wires. The crimp preferably compresses the sheath material against the distal end of the distal core wire. The implant can further include a second crimp that compresses the sheath material against the proximal end of the proximal core wire. The crimp preferably includes an elongate plastically deformable member that defines a first interior passage at a proximal end of the crimp for receiving at least one of the core wires surrounded by the sheath material. A second interior passage can be formed into a distal end of the crimp, the second interior passage having a smaller diameter than the first interior passage. The first interior passage and second interior passage can intersect. The second interior passage can be configured to receive a proximal end of a guidewire therein. At least one of the core wires can include a lubricious coating along at least a portion of its length, such as a hydrophobic coating (e.g., PTFE, PVDF) or a hydrophilic coating (e.g., PVP).

In some embodiments, the proximal end of the bridge can be elongated and extend proximally from the arched portion of the bridge to stiffen a portion of the wall of the heart to provide a reinforced region of the heart to facilitate implantation of a valve prosthesis within the mitral annulus. The proximal and distal ends of the bridge can be elongated and extend proximally and distally, respectively, from the arched portion of the bridge. One or both of the elongated ends of the bridge can converge toward a point. The proximal and distal core wires can be held in place with respect to the elongated ends of the bridge by way of a tubular member attached to at least one of the bridge and the core wires.

The disclosure provides a variety of methods, including but not limited to a method that includes some or all of directing a guidewire at least partially through a coronary sinus of a heart and over a coronary artery and into the right ventricle or the right atrium, withdrawing the distal end of the guidewire from the patient such that the proximal and distal ends of the guidewire are outside the patient, attaching an implant as disclosed herein to a proximal end of the guidewire, advancing the implant until the bridge straddles the coronary artery by pushing on the proximal core wire and pulling on the distal core wire, detaching the core wires from the bridge and withdrawing them from the patient, applying tension to the sheath material to reshape the mitral valve, and fixating the implant to maintain the tension in the sheath.

If desired, the method can further include implanting a transcatheter prosthetic mitral valve within the native mitral valve region, wherein the prosthetic mitral valve applies an outward expansion force on myocardium underlying the coronary artery, and further wherein the bridge inhibits application of compressive pressure to the coronary artery by the prosthetic mitral valve. If desired, the bridge of the implant can have an elongated proximal portion that forms a reinforced landing zone region to facilitate implantation of the prosthetic mitral valve. The method may include releasing the tension in the sheath material of the implant, repositioning the implant, and reapplying the tension to the sheath material.

The disclosure still further provides embodiments of a snare catheter that includes an elongate core member having a proximal end and a distal end, an elongate intermediate tubular member having a proximal end, a distal end and defining an elongate lumen therethrough for slidably receiving the elongate core member therein, a collapsible tubular perforated body formed from a plurality of braided members attached at a proximal end thereof to the distal end of the elongate intermediate tubular member, and at a distal end thereof to the distal end of the elongate core member, wherein relative axial displacement of the distal end of the elongate intermediate tubular member toward the distal end of the elongate core member causes the collapsible tubular perforated body to expand radially outwardly and for the braided members to mutually separate, and relative axial displacement of the distal end of the elongate intermediate tubular member away from the distal end of the elongate core member causes the collapsible tubular perforated body to collapse radially inwardly and for the braided members to collapse together. The snare catheter can further include a target wire disposed within the collapsible tubular perforated body that extends along the elongate core member and has a proximal end attached to the elongate intermediate tubular member and a distal end attached to the elongate core member. The target wire can be configured to assume a first generally straight configuration when the collapsible tubular perforated body is collapsed radially inwardly, and a second substantially nonlinear configuration when the collapsible tubular perforated body is expanded radially outwardly. The snare catheter can further include an elongate tubular longitudinally displaceable sheath having a proximal end, a distal end and defining an elongate lumen therethrough for slidably receiving the elongate core member, elongate intermediate tubular member, collapsible tubular perforated body, and target wire therein when the collapsible tubular perforated body is in a generally radially collapsed state.

If desired, the elongate core member of the snare catheter can be a tubular member defining a guidewire lumen therethrough. The snare catheter can be provided with an atraumatic distal tip formed from compliant material that is attached to the distal end of the elongate core member. The snare catheter (or any device described herein) can further include radiopaque marker bands disposed near the distal end of the catheter and the distal end of the elongate intermediate tubular member. If desired, the snare catheter can include a plurality of radiopaque marker bands formed on the target wire. The target wire can be formed at least in part from radiopaque material. The collapsible tubular perforated body can be formed at least in part from radiopaque material.

In some implementations, the target wire can include at least one loop and/or undulation formed therein when it is longitudinally contracted. If desired, the target wire can include a plurality of loops and/or undulations formed therein when it is longitudinally contracted. The target wire and loop (and/or undulation) can substantially lay in a single plane parallel to a longitudinal axis of the catheter when the target wire is longitudinally contracted. The target wire and loop(s) and/or undulation(s) can define a three dimensional geometry when the target wire is longitudinally contracted. If desired, a plurality of target wires can be provided having one or more loops and/or undulations when the target wires are longitudinally contracted. The target wire can include composite wire, such as a wire that includes a core portion made from a first material, and a cladding portion made from a second material different from the first material.

The disclosure further provides a lock delivery catheter that includes an elongate inner tubular member having a proximal end and a distal end, an elongate outer tubular member having a proximal end, a distal end and defining an elongate lumen therethrough for slidably receiving the elongate inner tubular member therein, and a deployable lock attached to the lock delivery catheter including a lock body and a wedge, the wedge being configured to wedge against the lock body when the lock body and wedge are pressed together.

The lock body is typically detachably attached to the distal end of the elongate outer tubular member, and the wedge is typically detachably attached to the distal end of the elongate inner tubular member. The lock delivery catheter can further include at least one guiding suture routed between the lock body and the wedge and extending proximally through the elongate inner tubular member. The at least one guiding suture can be a snare suture including a loop formed at a distal end thereof for attaching to a second suture to facilitate drawing the second suture through the lock delivery catheter. The lock body can include a pin that spans the lock body, and the pin can pass through a portion of the wedge to couple the lock body to the wedge. The pin can pass through a longitudinal groove formed in the wedge, such that the lock body and wedge can slide with respect to each other along the longitudinal groove. The wedge can include a proximal portion defining a proximal opening that extends into a central passage in the proximal portion that divides into two passages that terminate at two distal openings defined in two surfaces that lay on either side of an elongate portion of the wedge that defines a longitudinal slot therein. Each of the two distal openings each can include a suture passing therethrough that extend proximally through the elongate inner tubular member and distally between the lock body and the wedge. The lock body can define a distal opening for routing at least one suture therethrough. The distal opening of the lock body can include at least one distally extending sleeve disposed therein for guiding a suture therethrough. The distal opening of the lock body can include two distally extending sleeves disposed therein for guiding a suture therethrough. At least one of the sleeves can include two concentric sleeves that cooperate to form a telescoping sleeve capable of being adjustable to more than one length. At least one of the sleeves can include an atraumatic distal tip formed thereon. If desired, at least one of the sleeves can include an opening formed through a wall thereof configured to permit a tether to pass therethrough, rather than having the tether traverse the full length of the sleeve.

In some implementations, the lock delivery catheter can further include a handle attached to a proximal portion of the outer tubular member that can be provided with one or more actuators. The lock delivery catheter can be provided with a tether loop routed through a portion of the lock body and extending proximally to a tether clamp, the tether loop being configured to hold the lock body fast against a distal end of the outer tubular member. The handle can be provided with at least one spring loaded clamp configured to selectively maintain tension on a tether of an implant, or on any other desired filament. In some implementations, the distal end of the outer tubular member can be configured to interdigitate with the lock body so that the outer tubular member can transmit torque to the lock body. If desired, the distal end of the outer tubular member can be shaped to guide the lock body into the distal end of the outer tubular member.

The disclosure further provides a cutting catheter that can include an elongate inner member having a proximal end and a distal end with a distally facing blade mounted on the distal end, and an elongate outer tubular member having a proximal end, a distal end and defining an elongate lumen therethrough for slidably receiving the elongate inner tubular member therein, wherein the elongate outer tubular member defines a pair of laterally offset holes therethrough near the blade for receiving a suture material therethrough, wherein distal advancement of the elongate inner member with respect to the elongate outer tubular member passes the blade past the suture to cut the suture. If desired, the distally facing blade can be mounted on a generally planar distal region of the elongate inner member that is configured to slide within a flattened distal portion of the elongate outer tubular member.

The disclosed devices may be used in methods of improving the function of a mitral valve in a subject in which an annuloplasty element, for example an element that exerts compressive tensile remodeling forces on the mitral valve (such as a tensioning element), is introduced at least partially around the mitral valve, for example at least partially through the coronary sinus and over a coronary artery. The protective device is placed between the annuloplasty element and the coronary artery, with the annuloplasty element separated from the underlying coronary artery by the bridge of the device. Reinforcing core elements can then be removed from the device and a lock can be introduced over the device and advanced to a location where it can maintain tension on the implant.

Compressive remodeling forces are exerted by the annuloplasty device (for example by applying tension on a tensioning element to alter the shape or configuration of the mitral valve annulus to reduce its circumference) while supporting the annuloplasty element on the bridge to inhibit application of pressure to the coronary artery. The function of the mitral valve in the patient is thereby improved without impairing coronary blood flow.

In one example of a method in accordance with the disclosure, a catheter is introduced into the great cardiac vein, and a guidewire or other penetrating device (such as a needle, radiofrequency energy ablation device or laser ablation device) into a basal blood vessel such as the first septal coronary vein. From there the penetrating device directly traverses under imaging guidance the septal myocardium or annulus fibrosis and reenters the right ventricle or right atrium.

The guidewire is then retrieved using, for example, a target catheter having a deployable basket forming an outer envelope that is complemented by a three dimensional internal winding. The guidewire is captured by passing it through at least a portion of the basket, and preferably, at least a portion of the internal winding. The basket is then collapsed to draw the guidewire into a body of the target catheter, and the guidewire is percutaneously withdrawn from the patient, resulting in both ends of the guidewire being exposed. The implant is then crimped onto the proximal end of the implant, and the implant is advanced into the body until the bridge portion of the implant straddles a coronary artery, such as the left circumflex ("LCx") artery. The location of the LCx artery can be identified, for example, by radiocontrast angiography or by fusion of prior computed tomography angiography and live X-ray or using intravascular ultrasound. In an alternative approach, coronary veins are entered in the other direction from the right atrium or right ventricle under imaging guidance into a branch of the coronary sinus.

At this point, the guidewire and crimp are preferably external to the body, as well as the proximal end of the implant. Core wires that run through the proximal and distal portions of the implant inside of a sheath are then preferably removed, leaving behind the implant, wherein the sheath material is long enough to extend out of the patient. A lock can then be threaded over both proximal and distal sheath portions of the implant that respectively contact the bridge portion using a lock delivery catheter, and the lock can be advanced into the patient's heart. Tension can be imposed in the sheath of the implant to achieve the desired anatomical change. Tension is preferably applied to the proximal and distal sheath portions under imaging guidance until the desired degree of mitral annular circumferential reduction is accomplished, or until the mitral valve regurgitation is reduced, or until other deleterious endpoints are achieved such as mitral valve inflow obstruction. The lock can be locked via manipulation of the lock delivery catheter, which then in turn can be removed, and a cutting catheter can be advanced over the proximal and distal sheath portions of the implant. The sheath portions are preferably internal to the lock and lock catheter. Excess sheath can be removed using the cutting catheter as disclosed herein, and the cutting catheter can both be removed from the patient, completing the procedure.

It is to be understood that both the foregoing general description and the following detailed description are exemplary and are intended to provide further explanation of the embodiments disclosed herein.

The accompanying drawings, which are incorporated in and constitute part of this specification, are included to illustrate and provide a further understanding of the method and system of the disclosure. Together with the description, the drawings serve to explain the principles of the disclosed embodiments.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 3A is a left lateral external perspective view of the heart showing the lateral coronary artery branching from the ascending aorta, the branch of the lateral circumflex artery, and the great cardiac vein.

FIG. 3B is an enlarged view of a section of the arteries showing the coronary sinus crossing superficial to the left circumflex coronary artery at the level of the great cardiac vein.

FIG. 3C is a view similar to FIG. 3B but showing placement of a ligature (for example, and without limitation, a wire or suture) during annuloplasty without the protective device in place. When the ligature is tightened during the annuloplasty procedure, pressure is exerted on the branch of the coronary artery, restricting blood flow and myocardial perfusion.

FIG. 3D is an enlarged view of this same structure showing placement of the protective device over the ligature within the coronary sinus and superficial to the coronary artery.

FIGS. 14A and 14B illustrate aspects of a lock delivery system in accordance with the disclosure.

FIGS. 19C-19AH illustrate aspects of further embodiments of a lock delivery system in accordance with the disclosure.

FIGS. 20A-20C illustrate deployment of the lock on the exemplary cerclage device in an animal.

FIGS. 22A-22F illustrate further aspects of the cutting instrument of FIG. 19.

FIG. 22G illustrates placement of the cutting instrument of FIG. 19 in a procedure.

DETAILED DESCRIPTION OF ILLUSTRATIVE EMBODIMENTS

I. Explanation of Terms

Figure 1A:
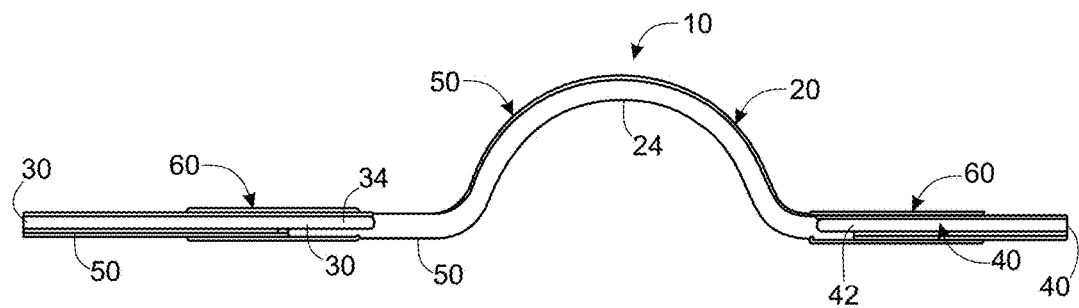
FIGS. 1A-1AR illustrate aspects of various embodiments of improved cerclage implants in accordance with the present disclosure.
Figure 1B:
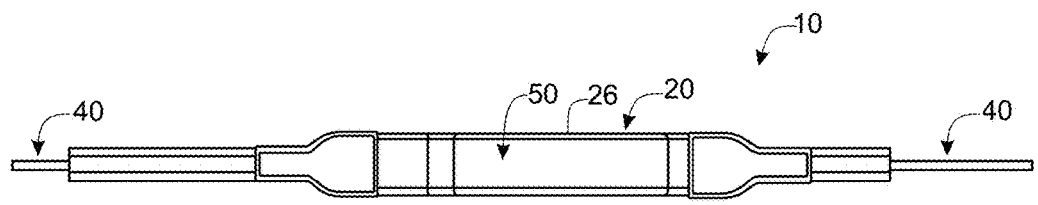
Figure 1I:
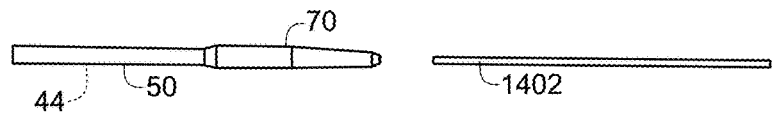
Figure 1J:
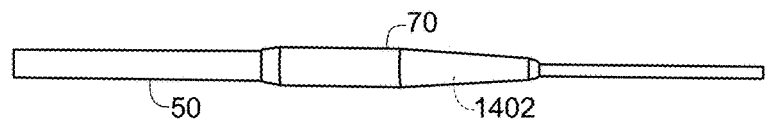
Figure 1K:
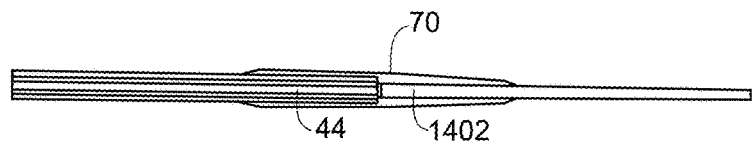
Figure 1L:
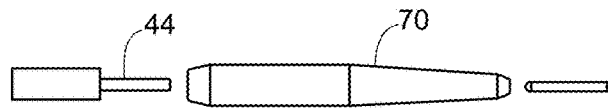
Figure 1M:
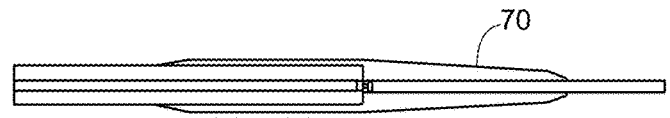

Unless otherwise noted, technical terms are used according to conventional usage. In order to facilitate review of the various embodiments of the disclosure, the following explanation of terms is provided:

"Annuloplasty element" refers to a device that induces reshaping of an annulus of the heart to repair valvular insufficiency. Such devices include those that are placed in the coronary sinus and exert their action by compressive forces on the annulus, for example by expansion of a resilient annuloplasty element, or placement of the annuloplasty element under tension, as in cerclage annuloplasty.

The term "comprises" means "includes without limitation." Thus, "comprising a guiding catheter and a guide wire" means "including a guiding catheter and a guide wire," without excluding additional elements.

The term "guide wire" refers to a simple guide wire, a stiffened guide wire, or a steerable guide-wire catheter that is capable of puncturing and/or penetrating tissue. The guide-wire also can deliver energy to augment its ability to penetrate tissue, for example by puncturing it, delivering radiofrequency ablative energy or by delivering laser ablative energy.

These are examples of a "penetrating device," which is a device capable of penetrating heart tissue, such as the myocardium.

As used herein, the term "ligature" is meant to encompass any suitable tensioning material and is not limited to only suture material. The term "tensioning material" or "ligature" includes sutures and annuloplasty wires.

A "mitral valve cerclage annuloplasty" refers to an annuloplasty procedure in which a tensioning element is placed through at least a portion (and preferably all) of the coronary sinus so that the circumferential tension is delivered around the mitral valve annulus and so that a tensioning element can be placed under selective degrees of tension to perform the annuloplasty. An example of cerclage annuloplasty is disclosed in co-pending prior application Ser. No. 11/127,112 (U.S. Patent Publication No. 2005/0216039), and the disclosure of the description of that technique is incorporated herein by reference for any purpose whatsoever. However, the mitral valve cerclage annuloplasty technique also includes other cerclage trajectories, such as those disclosed herein, including a trajectory through a proximal coronary septal perforator vein and myocardium or annulus fibrosis interposing between that vein and the right ventricle or right atrium to create circumferential cerclage annuloplasty tension.

The protective (or protection) device disclosed herein can be made of an "MRI-compatible" material. Such materials are safe to use in the body during magnetic resonance imaging of the body, and do not substantially affect imaging quality of the MRI. An "MRI-safe" material is one that does not add substantial risk to a human or equipment by placing it in the magnetic field of an MR environment. Examples of MRI-compatible materials are non-ferrous materials, such as ceramics, plastics and nonmagnetic composite materials. Austenitic stainless steels (of the 300 series) are neither ferromagnetic nor paramagnetic and therefore are MRI-compatible. Titanium and aluminum are MRI-compatible, even though they are not ideally paramagnetic. Particularly disclosed MRI-compatible materials of which the protective device may be made include nitinol, MP35N and cobalt-chromium alloys.

"Tensioning material" is any material suitable to perform a coronary sinus mitral valve cerclage annuloplasty, in which an encircling material is placed under tension to remodel the mitral valve annulus. Examples of suitable tensioning materials are preferably a sheath material (e.g., made from a woven polymeric material) as described herein.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. The term "or" refers to a single element of stated alternative elements or a combination of two or more elements, unless context clearly indicates otherwise. For example, the phrase "rtMRI or echocardiography" refers to real-time MRI (rtMRI), echoradiography, or both rtMRI and echocardiography. Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

II. Protection Devices to Protect Coronary Arteries

Coronary sinus mitral valve cerclage annuloplasty is an example of a percutaneous mitral valve repair procedure for which the disclosed protective device can be used. Although the device and methods of its use are broadly applicable to any prosthetic annuloplasty element placed in the coronary sinus, the methods will be described in connection with the particular example of cerclage annuloplasty. This specific example should not be construed to limit the procedure to use with cerclage annuloplasty, but only to illustrate its use in a particular embodiment.

Cerclage annuloplasty percutaneous repair carries a lower risk or morbidity than conventional mitral valve surgery, and thus can be used in patients who have less severe or more severe valvular dysfunction. Placing cerclage tethers, or ligatures, at least partially through the coronary sinus takes advantage of the proximity of the coronary sinus to the mitral valve annulus, and of the ready catheter access to the coronary sinus and tributary veins. These approaches also have limiting drawbacks, however, in that compression of nearby coronary artery branches is a serious risk in a majority of human subjects. The coronary sinus usually runs superficial to the circumflex coronary artery and its marginal branches near the great cardiac vein, and therefore trans-sinus annuloplasty can transmit pressure sufficient to constrict or occlude the coronary artery or its branches. Devices and methods that prevent this compression of the coronary artery, such as those disclosed herein, can dramatically increase the safety and efficacy of trans-sinus mitral cerclage annuloplasty.

An exemplary transcatheter-mitral-valve-cerclage annuloplasty involves the introduction of a tensioning material or device around the mitral valve annulus using a guiding catheter and a secondary catheter, such as a steerable microcatheter directing coaxial guide wires or canalization catheter. Access to the area around the mitral-valve annulus can be accomplished using a variety of percutaneous approaches, including access from and through the coronary sinus. In particular embodiments, a tensioning material that constitutes a portion of an implant is applied around the mitral-valve annulus along a pathway that, in certain embodiments, includes an extra-anatomic portion. For example (and without limitation), the tensioning material can traverse a region between the anterobasal-most portion of the coronary sinus and the coronary-sinus ostium. As another non-limiting example, such tensioning material can be applied across the atrial aspect of the mitral valve from the posterolateral aspect to the anterior aspect of the coronary sinus, or from the septal aspect to the lateral aspect of the mitral-valve annulus. This procedure reduces the mitral annular cross-sectional area and septal-lateral wall separation, thereby restoring a line of coaptation of the mitral valve.

Because it has been found that mitral annuloplasty via the coronary sinus unintentionally transmits pressure sufficient to constrict or occlude the underlying coronary artery, the devices disclosed herein have been developed to increase the safety and efficacy of the procedure. The disclosed improved devices and related methods protect an underlying vessel from compression during mitral annuloplasty in which a cerclage ligature extends at least partially through the coronary sinus over a coronary artery. As discussed in U.S. patent application Ser. No. 15/056,599, filed Feb. 29, 2016, a coronary protection element is disclosed for use with a cerclage device. However, the presently disclosed embodiments provide significant improvements over that disclosure.

In one embodiment shown in FIG. 1A, the device 10 includes a surgically sterile protection device or bridge 20 of a suitable shape and size to permit its introduction through a transvascular catheter into the coronary sinus. As illustrated, the bridge 20 includes a solid generally arcuate body having an upper face 22, lower face 24 and two arcuate sides 26 that flattens out to two flattened, rounded proximal and distal ends 28, 29 wherein the two ends 28, 29 of the body 20 extend in approximately the same plane, and are longitudinally aligned with a distal end 32 of a proximal core wire/push wire 30 and a proximal end 42 of a distal core wire/push wire 40. These components are then in turn encased in an elongate sheath 50 that is preferably made from a knit or woven polyester or other suitable material that stretches over the bridge 20 and core wires 30, 40. In the illustrated embodiment, suture wraps 60 are applied to hold the sheath 50 in place with respect to the core/push wires 30, 40 to maintain the physical positioning of the various components of device 10. In another embodiment, shrink tubing segments or the suture wrap material 60 could be applied over the junction of the bridge 20 and each core wire 30, 40 to hold the core wires in place.

While the core wires 30, 40 could simply abut either end of the protection element 20 or lay over the top or bottom of the end of the protection element 20, in the illustrated embodiment, a short hypotube length can be used that is either attached to the grooves 28a, 29a or the flattened ends 28, 29 generally, such as by soldering, welding or other suitable attachment method. In another embodiment, a longitudinal indentation or groove 28a, 29a can be formed at each flattened end 28, 29 of the protection element 20 that is sized and shaped to receive the ends 32, 42 of the core wires.

As illustrated in FIG. 1C, the slot 28a/short hypotube length corresponding to the distal end 32 of the proximal core wire 30 is longer than slot 29a/short hypotube length corresponding to proximal end 42 of the distal core wire 40, and the respective flattened ends 28, 29 of the bridge 20 are correspondingly longer. That is to say, the flattened proximal region 28 of the bridge 20 is noticeably longer than the distal region 29 of the bridge. Elongation of the proximal region of the bridge with the correspondingly longer groove 28a provides a longer overlap with the core wire 30 and thus enhances stability. The distal end 29, on the other hand, is comparatively short so as to reduce contact with the septum wall when implanted as the LCx is typically very close to the septum wall.

In use, as discussed in detail further below, distal core wire 40 is advanced through the vasculature first while advancing the protection element 20 to its final location within the heart. Specifically, proximal core wire 30 effectively "pushes" bridge 20 while wire distal wire 40 effectively "pulls" bridge 20. The entire assembly of components 20, 30, 40 is held in place as an integral unit by the continuous outer sheath 50. The core wire ends 32, 42 are held in place with respect to the bridge 20 by virtue of compression exerted on the sheath 50 and wires 30, 40 by the suture wrap 60. When the protection bridge 20 is positioned, the core wires 30, 40 may be pulled out of the sheath 50 to structurally separate the sheath 50 from each core wire 30, 40, and applying tension to each respective core wire on one end, and the sheath 50 on the other end, leaving the protection element 20 behind covered by the sheath. Bridge 20 fits snugly within sheath 50, making relative movement of one with respect to the other unlikely. Either end of the sheath material 50 may then be tensioned to reshape the mitral annulus, locked off, and the excess sheath 50 may be cut off, described in further detail below. Suture wrap 60 can be, for example, a TEVDEK® 5-0 USP (e.g., ~0.004 inch thick) PTFE impregnated braided polyester fiber nonabsorbable surgical suture from Teleflex, Inc. Suture wrap 60 remains on the implant 10 after removal of the core wires 30, 40, and may be applied to the junction of the sheath 50, core wires 30, 40, and the bridge 20 as well as extending proximally and distally along the sheath and core wires.

The protection element 20 is preferably made from rolled wire that is radiopaque, such as 0.020 inch by 0.070 inch nitinol wire, but it will be appreciated that other materials can be used of similar or differing dimension. Being made from a shape memory material allows the bridge 20 to be deformed (for example toward a linear configuration) that is adaptable to introduction through the vascular system. However, the shape memory material preferably returns to the arched configuration shown in the drawings after the device is deployed.

The member 20 may have a round cross section or rectangular cross section having a diameter, or respective height and width between about 0.010 inches to about 0.080 inches and in any desired increment of 0.001 inches between those values. As illustrated, the ends of the protection element 20 are preferably rounded so as to not cause trauma to the wall of the coronary sinus as it is advanced. The protection device 20 preferably has an arcuate, or semi-circular shape of sufficient radius to extend closely over an underlying coronary artery (e.g., the LCx) to inhibit the transmission of compressive forces from the tension element to the underlying artery. The compressive forces are instead distributed on and along the protection device to protect the artery from compression that impairs myocardial perfusion. Protection element end portions 28, 29 effectively form "feet" that can rest against a wall of the coronary sinus while straddling a coronary artery to retain protection device 20 in position over the left circumflex artery and bear and distribute the compressive forces that are applied by the sheath 50 when the under tension after the core wires 30, 40 are removed.

The embodiment of FIG. 1A has a central arch bridging a linear distance at its base of from about 0.4 inches to about 0.7 inches, for instance, in any desired increment of 0.01 inches therebetween. The illustrated central arch has a height h from about 0.10 inches to about 0.20 inches high, for instance, in any desired increment of 0.01 inches therebetween.

As can be appreciated from FIGS. 1C-1E, the hollow tether/sheath material 50 and the bridge 20 are ultimately implanted, whereas the core wires 30, 40 are removed. As illustrated in FIG. 1H, the core wires 30, 40 are preferably formed from a stainless steel alloy and are coated with a lubricious material, such as PTFE, PVDF, or PVP, to facilitate removal from the body after they are detached from the bridge 20. The core wire may be, for example, between about 0.010 and about 0.020 inches in diameter, or any increment therebetween of 0.001 inches. The sheath/tether 50 can be made from a hollow braided material. In the present disclosure, sheath material 50 may also be referred to as a "tether" or a "suture".

Figure 1N:
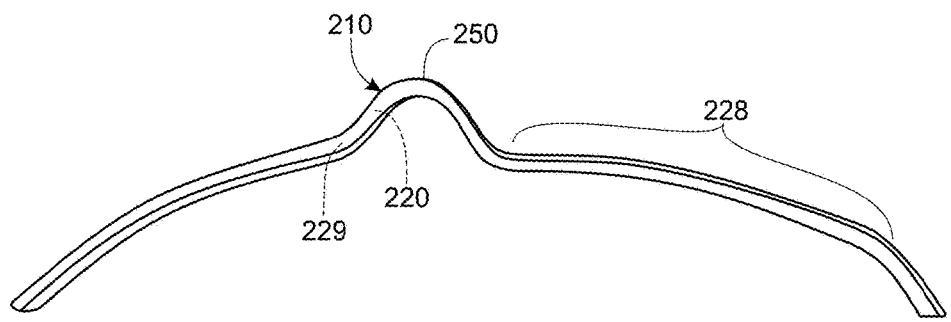
Figure 1O:
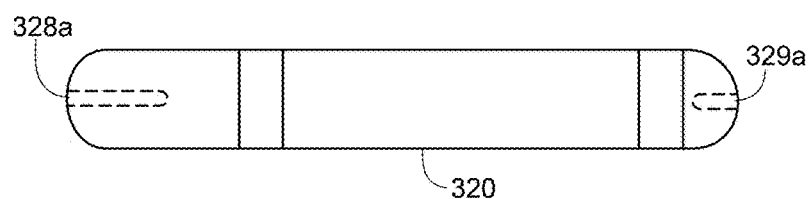
Figure 1P:
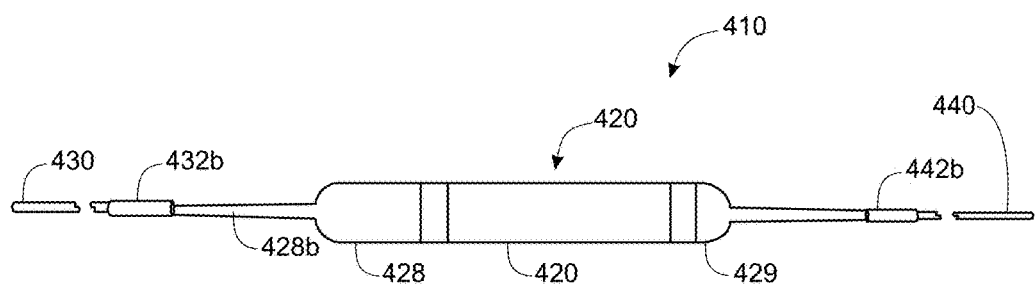
Figure 1Q:
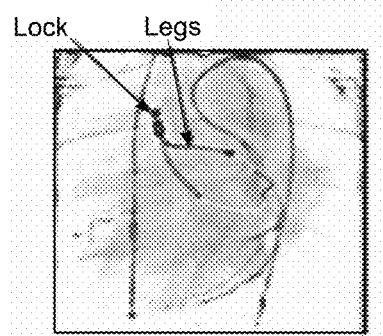
Figure 1R:
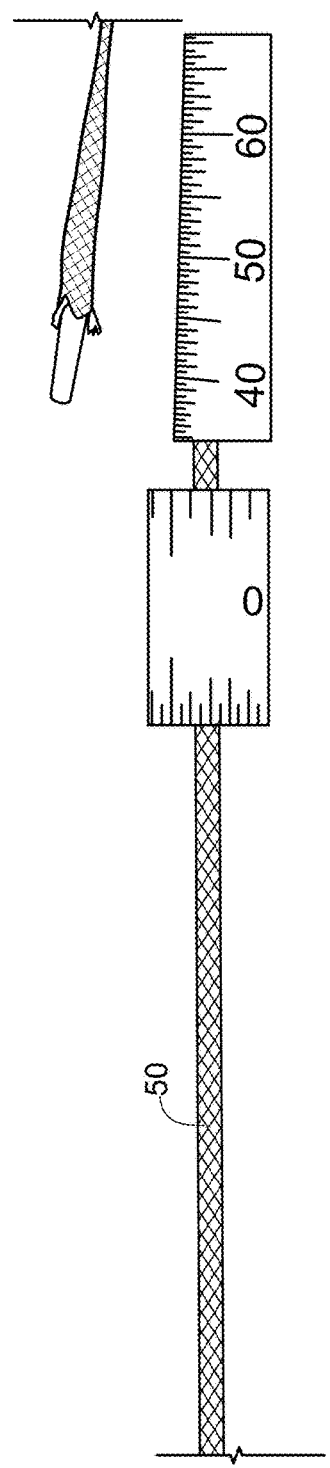

In one embodiment, as illustrated in FIG. 1R, sheath 50 can be made from a 1-2 mm ultra high molecular weight polyethylene ("UHMWPE") coreless round braid from DSM, Dyneema or Teleflex. Preferably, the tether/sheath 50 is loaded with at least 20% bismuth by weight to enhance radiopacity. For example, the sheath may be loaded with between about 20 and about 70% bismuth or barium sulfate, or to any degree therebetween in increments of about 1% by weight. Additionally or alternatively, additional or alternative radiopaque materials can be incorporated into the sheath material, such as tungsten, tantalum, and barium sulfate. These materials can be incorporated, for example, as drawn metallic (e.g., platinum, or other radiopaque material) wires incorporated into the braiding, such as by weaving, or by directing the drawn wire along a central channel defined within the tether. In a further embodiment, ultra high molecular weight polyethylene can be used as a tether material for improved creep resistance, and is preferably 1-2 mm in size, and is commercially available from Teleflex Corporation. While braided materials are illustrated for tether/sheath 50, it will be appreciated that any other suitable material can be used.

FIGS. 1F and 1G depict an exterior side view, and cross sectional view, respectively, of a crimp 70 that provides a transition region from a guidewire to the distal end of the distal core wire 40. A second crimp at the proximal end of the implant, if provided, can provide an alternative or additional structural attachment location for affixing the proximal end of the tether 50 to a proximal end of the proximal core wire 30. Further views of the crimp and its manner of use are also illustrated in FIGS. 1I-1M. As illustrated, the crimp 70 includes an external proximal tapering generally conical surface 72, an external distal tapering generally conical surface 74 and two intermediate tapering external conical surfaces. The distal end of the crimp is smaller in diameter than the proximal end of the crimp 70 to define a relatively large proximal bore 76 for receiving the distal end 44 of the distal core wire 40 housed within sheath 50, and a relatively narrow, intersecting distal bore 78 that is sized to receive the proximal end 1402 of a guidewire 1400. The crimp 70 is preferably made from a deformable metallic material that is initially affixed to the core wire 40 of the implant 10. Once the guidewire is introduced and has been properly routed through the heart and out of the body (discussed in further detail below), the crimp 70 of implant 10 is then crimped onto the guidewire (e.g., with a hand crimper), and the implant 10, including core wires 30, 40, protection element 20 and sheath 50 with suture wraps 60 are advanced through the vasculature until the protection element straddles the LCx artery.

FIG. 1N illustrates a further embodiment of an implant 210 that includes a protection device 220, or arch, that has a significantly elongated proximal portion 228 that forms a "landing zone", or stiff, stable structure when implanted within the coronary sinus. This landing zone can then serve as a location for implanting a replacement valve after the transcatheter annuloplasty procedure has been completed. Specifically, having a relatively rigid surface within the heart provided by the landing zone created by elongated proximal portion 228 facilitates anchoring of such a replacement valve to the native tissue. The proximal portion 228, if provided, can thus have any suitable length between, for example, 3 and 80 mm, and in any desired increment of 1 mm therebetween. The distal portion 229, if provided, can have any suitable length between 0.5 mm and about 10 mm, and in any desired increment of 0.5 mm therebetween.

FIG. 1O illustrates a third embodiment of a protection device, or bridge, 320 that may be used in the disclosed implants (e.g., 10, 210). Bridge 320 includes proximal and distal slots 328a, 329a at the proximal and distal ends 328, 329 of the bridge 320 for receiving welded hypotube lengths therein to in turn receive core wires 30, 40, therein for enhanced alignment and stability. Rather than slots with hypotube segments, holes can instead be bored into each end of the bridge 20 by way of electrical discharge machining ("EDM") techniques.

FIG. 1P illustrates yet another embodiment of an implant 410 that includes a protection bridge 420 having proximal and distal extensions 428b, 429b extending outwardly from proximal and distal regions 428, 429 of the bridge 420. Proximal extension 428b is in turn received by a distal end sleeve 432b of proximal core wire 430, and proximal extension 429b is similarly received by a proximal end sleeve 442b of distal core wire 440. Core wires 430, 440 are provided to facilitate pushability and pullability of the sheath and protection bridge 420 while it is being advanced along a patient's vasculature. Core wires 430, 440 are preferably coated with a lubricious hydrophobic or hydrophilic material, such as PTFE, PVDF, other suitable fluoropolymer or PVP, for example. While extensions 428b, 429b may be of any desired length, in some embodiments, the extensions are sufficiently long to each traverse 5, 10, 15, 20, 25, 30, 35 or 40 percent of the annular extent of the implant 410 when installed, or in any desired increment of one percent therebetween. In another implementation, the extensions 428b, 429b, if provided, can have any suitable length between, for example, 3 and 100 mm, and in any desired increment of 1 mm therebetween. In such an embodiment, the extensions 428b, 429b may be of sufficient length to overlap with sleeve portions of a lock portion of the implant as illustrated in FIG. 1Q. The lock and sleeves are discussed in further detail below with respect to FIGS. 14-20.

Figure 1S:
Figure 1T:
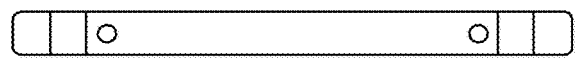
Figure 1U:
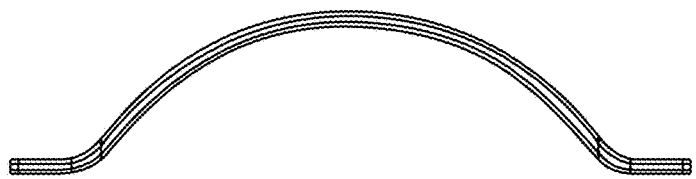
Figure 1V:
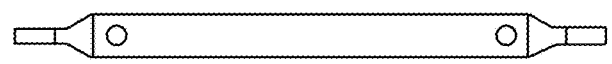

FIGS. 1S and 1T illustrate aspects of a fifth embodiment of a protection bridge in accordance with the present disclosure, while FIGS. 1U and 1V illustrate aspects of a sixth embodiment of a protection bridge in accordance with the present disclosure. These embodiments differ from the preceding embodiments in several respects. For example, while the entire implant structure is preferably incorporated into a tubular sheath material 50 (which is not specifically illustrated), an additional, preferably radiopaque, tether is provided along the length of the implant that is woven through and/or around the protection element. As illustrated, this additional tether is routed through openings defined through the protection element. As illustrated, each of the fifth and sixth illustrative embodiments of the protection bridge has proximal and distal extensions extending outwardly from proximal and distal regions of each bridge. The fifth embodiment has relatively wider feet at its ends to provide a more stable platform for seating the bridge, whereas the sixth embodiment has tapered feet at each end to provide a more gradual transition in stiffness from the protection bridge proximally and distally along the length of the implant. The interior tether so routed through the protection element is preferably radiopaque along its entire length by providing radiopaque material inside the tether along its length, or by incorporating radiopaque material into the fabric of the tether itself.

Figure 1W:
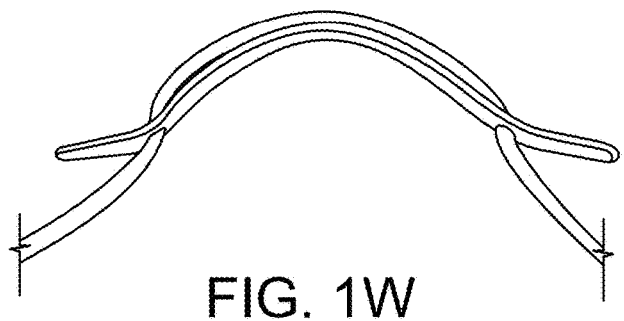
Figure 1X:
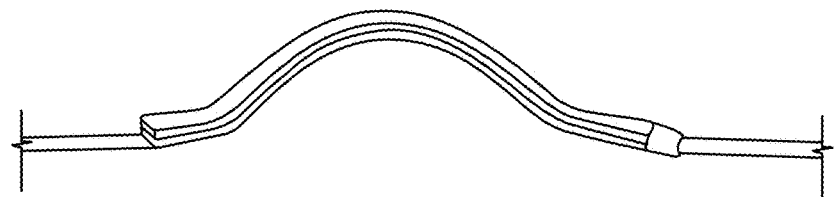
Figure 1Y:
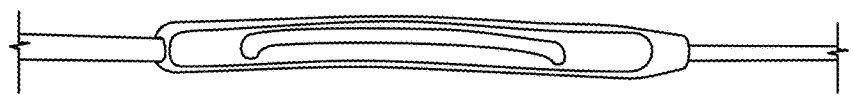
Figure 1Z:
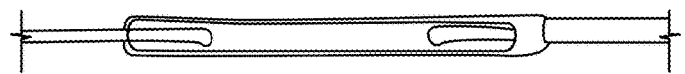
Figure 1A:
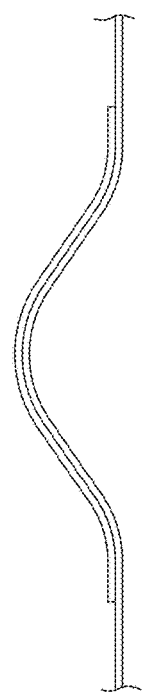
Figure 1A:
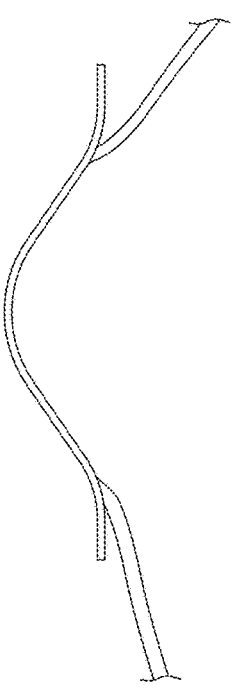
Figure 1A:
Figure 1A:
Figure 1A:
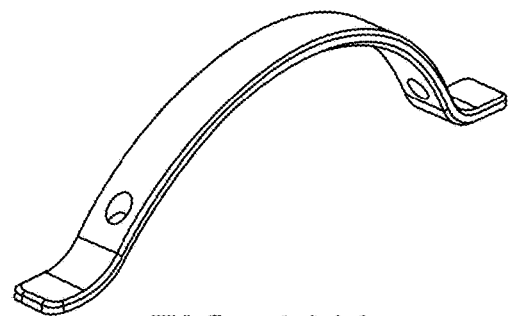
Figure 1A:
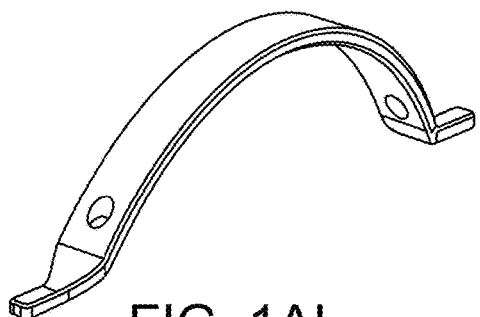
Figure 1A:
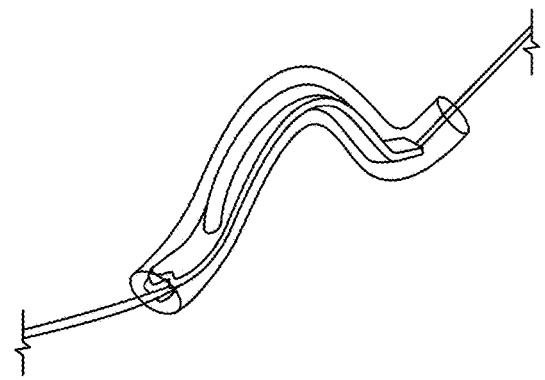
Figure 1A:
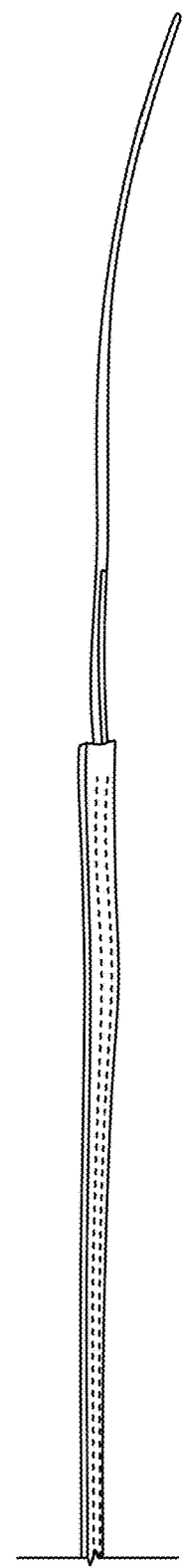
Figure 1A:
Figure 1A:
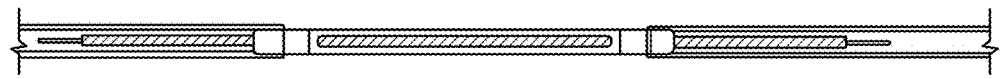
Figure 1A:
Figure 1A:
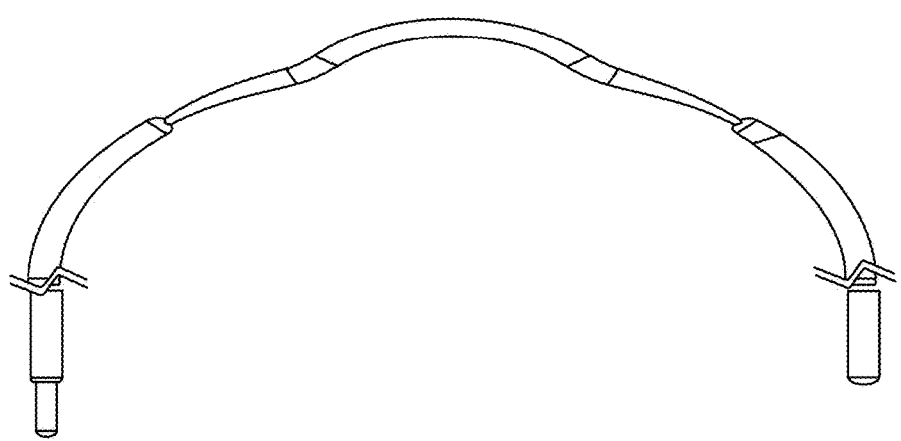

As illustrated in FIG. 1W, with respect to the fifth embodiment, a side view of the protection element is provided, and an isometric view is provided in FIG. 1AK, wherein the (preferably radiopaque) tether is threaded through the holes of the protection element during assembly. As presented, the tether is threaded over the arch, and underneath the seating portions/ends of the protection element. As shown in FIG. 1X, which presents a further side view of the protection element and tether, if desired, a cover is applied over the combination of the tether and protection element, such as a tube of heat shrinkable material, a wound thread, or tubular fabric material. In the illustration, a tube of heat shrinkable PTFE is applied to the structure, thereby holding the relative positions of the tether and the protection element. FIG. 1Y presents a top view of the assembly of FIG. 1W, illustrating routing of the tether over the top of the arch of the protection element, whereas FIG. 1Z illustrates routing of the tether underneath the seating area/end portions of the implant.

As illustrated in FIG. 1AA, with respect to the sixth embodiment, a side view of the protection element is provided, and an isometric view is provided in FIG. 1AL, wherein the tether is threaded through the holes of the protection element during assembly. As presented, the tether is threaded over the arch, and underneath the seating portions/ends of the protection element. As shown in FIG. 1AB, which presents a further side view of the protection element and tether, if desired, a cover is applied over the combination of the tether and protection element, such as a tube of heat shrinkable material, a wound thread, or tubular fabric material. In the illustration, a tube of heat shrinkable PTFE is applied to the structure, thereby holding the relative positions of the tether and the protection element. FIG. 1AC presents a top view of the assembly of FIG. 1AA, illustrating routing of the tether over the top of the arch of the protection element, whereas FIG. AD illustrates routing of the tether underneath the seating area/end portions of the implant.

FIGS. 1AE-AG present isometric, rear and front views, respectively, of a strain relief cap that can be incorporated into the implant. The strain relief includes an interior channel along its length for at least partially (preferably fully) surrounding the circumferential extent of the tether and protection bridge, having a relatively wide rear portion with a relatively large channel for accommodating the foot/seating area of the implant that tapers down toward a relatively narrow front portion that is configured and adapted to surround the sheath material. FIG. 1AH illustrates placement of the strain reliefs with respect to the protection element. FIGS. 1AI and 1AJ present top and side views, respectively, of the strain relief placed over the combined structure of the protection element, tether, and heat shrinkable tube. The strain reliefs can be made from heat shrinkable material and/or can be held in place with adhesive or the like. Moreover, the strain relief could be a braided tubular material, a wound polymeric or metallic wire, or a molded polymeric material of a soft durometer, wherein the tapered structure of the strain relief provides a gradient in durometer along its length to help achieve the function of relieving strain. The strain reliefs help provide a gradient in stiffness along the length of the implant from the protection element to the sheath to help avoid binding and stress concentrations that could be present in the absence of the strain reliefs. FIG. 1AM presents an isometric view of the implant without strain reliefs.

Preferably, the inner tether is radiopaque along its entire length to enhance visualization thereof during and after installation. FIG. 1AN illustrates a break away view showing the tether, in this case a braided tether, with a radiopaque (e.g., platinum) wire inserted inside of it to enhance radiopacity. Thus, while radiopacity can be enhanced by the presence of the illustrated platinum wire, the wire, or filament, can be formed from a tungsten loaded polymer, a tantalum loaded polymer, and/or a braided suture material can be used that is impregnated in one manner or another (e.g., by incorporation into the underlying polymer, or into the woven material) with one or more of bismuth, tungsten, tantalum, barium sulfate, and the like.

FIG. 1AO presents a top view of the combined structure of the protection bridge of Embodiment 5 (although the tapered Embodiment 6 of the protection bridge could similarly be used) with the tether routed therethrough, and with a radiopaque wire running the length of the tether inside of the interior tether.

The schematics of FIGS. 1AP and 1AR includes the aforementioned elements, and shows the addition of, and the relative positioning of, a removable push tube and a removable pull tube that is disposed over, or abutting, the ends of the protection bridge. The push and pull tubes perform a similar function to the core wires (e.g., 430, 440) of preceding embodiments. The push and pull tubes, as well as all other components of the implant, are surrounded by sheath (e.g., sheath 50) (illustrated surrounding the bridge and in combination with the delivery tubes in FIG. 1AR) as with the preceding embodiments. The removable push/pull tubes are assembled over the continuous inner tether on each side, running from the protection bridge to the exchange crimp (as illustrated in FIG. 1AR) to aid in exchanging out the guide wire for the cerclage implant. The push tube and pull tube can be made from polymeric material, for example, such as PEEK, HDPE, or the like, as desired. When the implant is in place, the push tube and pull tube are removed by pulling them out, as with the core wires (e.g., 430, 440) described elsewhere herein. FIG. 1AQ presents the same structural elements as FIGS. 1AO and 1AP, but further illustrates relative placement of the strain reliefs on either end of the protective bridge. It will be appreciated that the implant also preferably includes a further tubular element disposed over the sheath and protection element under the strain reliefs, as disclosed herein, and further includes the sheath 50 disposed over the entire structure. It will be understood that the interior, preferably radiopaque, sheath is of smaller diameter than the outer sheath 50. It will be further appreciated that, while an inner sheath of braided material is illustrated, other materials may be used including polymeric wires, metallic wires, and the like. The sheath 50 surrounding the structure can, in turn, include a lubricious coating along at least a portion of its length or all of its length, such as a hydrophobic coating (e.g., PTFE, PVDF) or a hydrophilic coating (e.g., PVP). This can be provided, for example, in the form of one or more tubes of PTFE shrink tubing. A larger diameter shrink tube can cover the central portion of the implant including the bridge 20 (when bridge 20 is provided) that overlaps with smaller diameter shrink tubing on either end to cover sheath 50. In one embodiment, the larger central shrink tube overlaps and covers the ends of the smaller tubes that adjoin it, or the opposite can be done. In a further embodiment, the distal end of the proximal smaller tubing section can be overlapped/covered by the proximal end of the larger tube, and the distal end of the larger tube can be covered and overlapped by the proximal end of the distal section of shrink tubing. The overlap regions can act as a strain relief to help provide regions of transitioning stiffness. The shrink tubing can be a multi-layer co-extrusion as described elsewhere herein that can include an intermediate braided layer formed from polymeric or metallic material, and may include radiopaque material.

Figure 2:
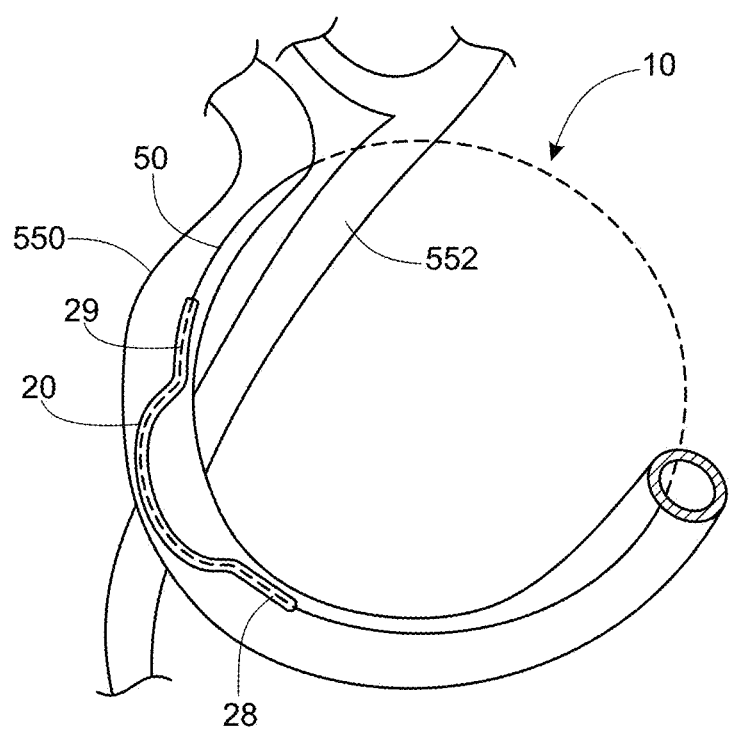
FIG. 2 is a schematic view showing an exemplary coronary protective device in position during a cerclage annuloplasty procedure.

FIG. 2 schematically illustrates the use of implant 10 using a protection device 20 in a mitral valve cerclage annuloplasty procedure. FIG. 2 depicts sheath material 50 used as a tensioning element (in a preferred embodiment, braided suture material) extending through a portion of the coronary sinus 550 over a circumflex coronary artery 552. FIG. 2 shows implant 10 positioned within coronary sinus 550 with protection element 20 extending over coronary artery 552, and proximal and distal portions 28, 29 being located on either side of coronary artery 552. As tension is placed on the tether portion 50 of implant 10, the proximal and distal portions 28, 29 are held in place on either side of coronary artery 552 and transmit compressive forces to the wall of coronary sinus 550 instead of on to underlying coronary artery (LCx) 552.

FIGS. 3A, 3B, 3C and 3D provide an alternative view of the function of cerclage annuloplasty protection device 10.

Figure 3A:
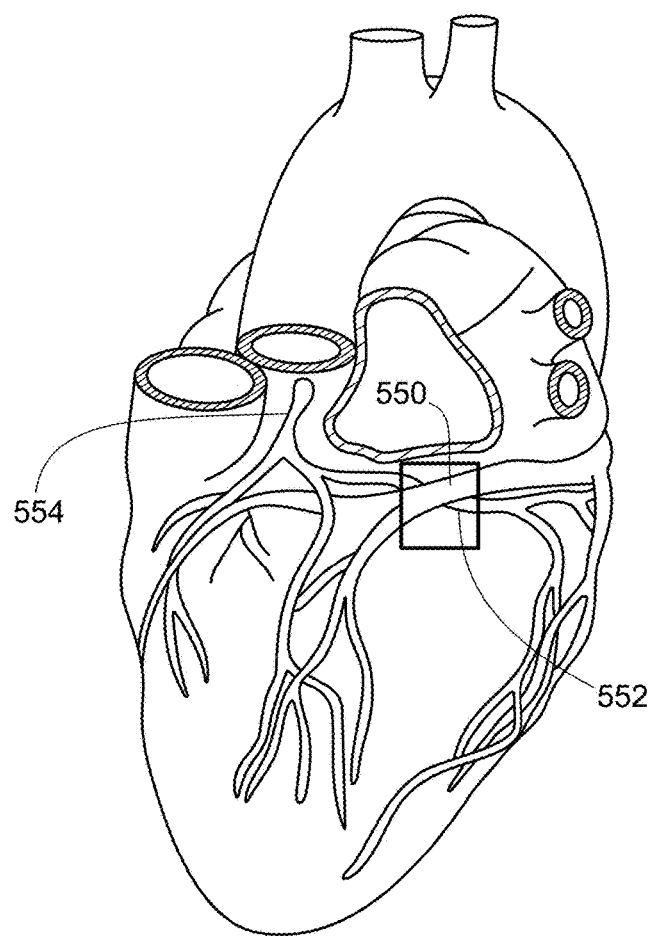
FIGS. 3A-3D is a set of drawings showing the region of the heart involved in trans-sinus coronary annuloplasty and illustrating the use of the protective device to prevent pinching of the coronary artery when tension is applied to a cerclage tensioning device.
Figure 3B:
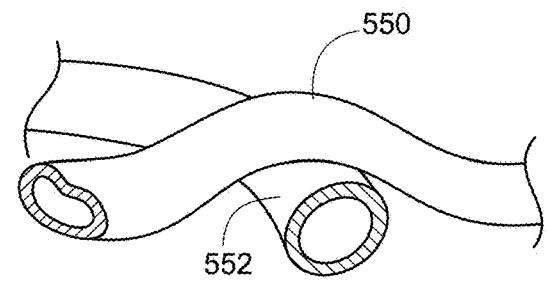
Figure 3C:
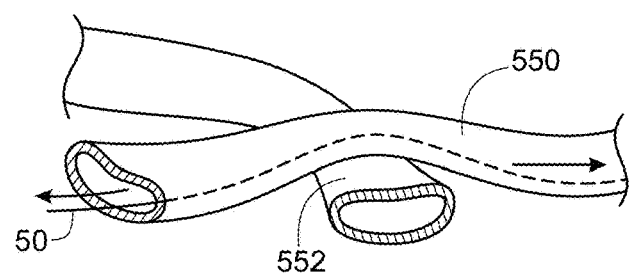
Figure 3D:
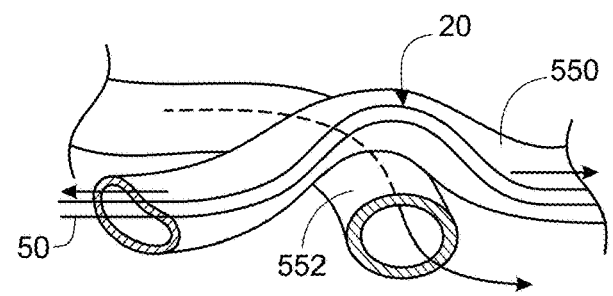
Figure 3F:
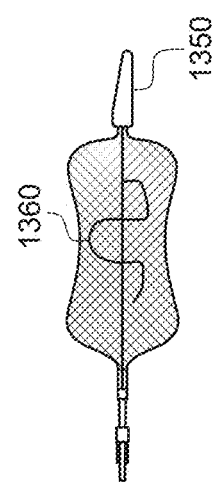
FIGS. 3E-3Y illustrate an exemplary snare catheter for capturing a guidewire, in accordance with the disclosure.
Figure 3H:
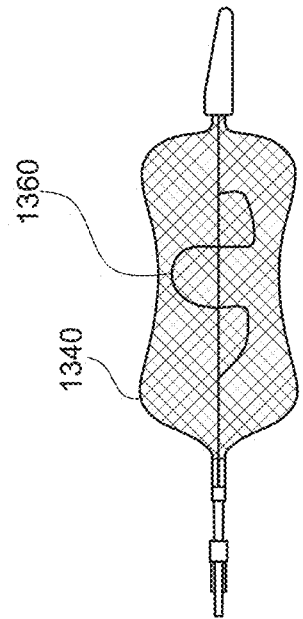

FIG. 3A shows the external anatomy of the heart, with coronary sinus 550 extending over a circumflex branch 552 of a left coronary artery 554. FIG. 3B shows an enlarged view of the overlapping relationship of coronary sinus 550 to coronary artery 552. FIG. 3C illustrates hollow tether 50 placed under tension during cerclage annuloplasty which is compressing underlying coronary artery 552 and interfering with myocardial perfusion. FIG. 3D shows hollow tether 50 extending through protection device 20 which is inhibiting the application of compressive force to coronary artery 552 which therefore remains patent and able to normally perfuse myocardial tissue.

It will be appreciated that the bridge/protection device (e.g., 20, 220, 320, 420) can assume a variety of shapes and configurations that support the hollow tether material 50 away from an underlying coronary artery (e.g., LCx). The protection device/bridge 20 can be pre-shaped to the desired configuration, or it can be made of a memory alloy material that is generally linear when being advanced through the vasculature but assumes the desired protection device shape once it is fully deployed. The bridge 20 can have curvature in three dimensions, as desired, to conform to a unique anatomy of an individual.

III. Percutaneous Mitral Valve Cerclage Annuloplasty

A. Mitral Regurgitation

Regurgitation (leakage) of the mitral valve or tricuspid valve can result from many different causes, such as ischemic heart disease, myocardial infarction, acquired or inherited cardiomyopathy, congenital defect, traumatic injury, infectious disease, and various forms of heart disease. Primary heart muscle disease can cause valvular regurgitation through dilation, resulting in expansion of the valvular annulus leading to malcoaptation of the valve leaflets through overstretching, degeneration, or rupture of the papillary muscle apparatus, or through dysfunction or malpositioning of the papillary muscles. This regurgitation can cause heart rhythm abnormalities such as atrial fibrillation, which itself can cause inexorable deterioration in heart muscle function. Such deterioration can be associated with functional impairment, congestive heart failure and significant pain, suffering, lessening of the quality of life, or even premature death.

A less dangerous, minimally invasive procedure, such as percutaneous annuloplasty, permits more patients to undergo mechanical treatment of valvular regurgitation.

B. Percutaneous Cerclage Annuloplasty

Because the risks and complications of surgery are reduced (compared with open-heart surgery), catheter-based heart-valve procedures are suitable for a broader population of patients. Disclosed herein are improved devices and methods for catheter-based valve repair that can be used to repair damaged or malfunctioning cardiac valves, for instance, by re-apposing valve leaflets by percutaneous-cerclage annuloplasty (reconstruction or augmentation of the ring or annulus of a defective cardiac valve). In some instances, percutaneous cerclage annuloplasty is used to deliver circumferential or radial tensioning devices. Examples of some of these procedures are described in detail in WO2004/045378 and US 2005/0216039, which are incorporated herein by reference in their entireties for any purpose whatsoever.

In general, the system used to carry out an annuloplasty procedure can include a guiding catheter (GC), such as a preformed transjugular balloon-tipped guiding catheter which is introduced into the coronary (venous) sinus. A retrograde coronary radiocontrast venogram pressurizes and visualizes the great cardiac vein and septal perforator veins. A high performance guidewire designed for coronary artery recanalization may be steered using a deflectable microcatheter, for example, into the great cardiac vein and thereafter into a basal septal perforator vein.

In general, an annuloplasty procedure also can include using an imaging system to image the internal bodily tissues, organs, structures, cavities, and spaces of the subject being treated. For example, transmitter or receiver coils can be used to facilitate active-device navigation using an imaging system, such as magnetic-resonance imaging (MRI). This imaging can generally be conducted along arbitrary or predetermined planes using various imaging methods based on X-ray technologies, X-ray fluoroscopy, MRI, electromagnetic-positron navigation, video technologies (such as endoscopy, arthroscopy, and the like), ultrasound, and other such technologies. In some embodiments, real-time MRI (rtMRI), intracardiac ultrasound, or electromagnetic guidance is employed. A particularly useful adjunct in cerclage annuloplasty is XFM, in which X-Ray is used with MRI to target myocardial structures, for example to help guide the annuloplasty wire in its trajectory through the structures of the heart. The XFM technique is disclosed, for example, in de Silva et al., *Circulation* 114:2342-2350 (2006). The guiding catheter enables percutaneous access into a subject's body, for example, percutaneous access to the heart, such as a chamber of the heart through an arm, neck, or leg vein. In some embodiments, the guiding catheter is designed for access to the ventricle and/or atrium of the heart. The guiding catheter permits introduction of one or more secondary catheters, including a valve-manipulation catheter or microcatheter or canalization-needle catheter, for example. The secondary catheter (or catheters) is used to treat, affect, or manipulate an organ, tissue, or structure of interest in the subject's body, such as the heart or particular structures within the heart. If the guiding catheter is used for percutaneous (or other) access to the heart, the guiding catheter permits introduction of one or more secondary catheters, such as a valve-manipulation catheter, into the heart while maintaining hemostasis. The secondary catheters may be coaxial or adjacent to each other, or may be introduced from multiple points of access outside the body.

Guiding catheters are available in different shapes to suit the appropriate component of the mitral-valve-repair procedure. For example, guiding catheter shapes can be provided to suit different coronary sinuses with different radii of curvature, to suit different coronary veins, transaortic as well as transseptal access routes, or to suit atria and ventricles of different calibers. All such shapes can be accommodated with appropriate primary, secondary, and tertiary curves. Examples of catheter configurations suitable to perform percutaneous transvascular mitral valve annuloplasty are known in the art and are described in detail in U.S. Patent Publication No. 2005/0216039, which is incorporated by reference herein in its entirety for any purpose whatsoever.

Figure 4A:
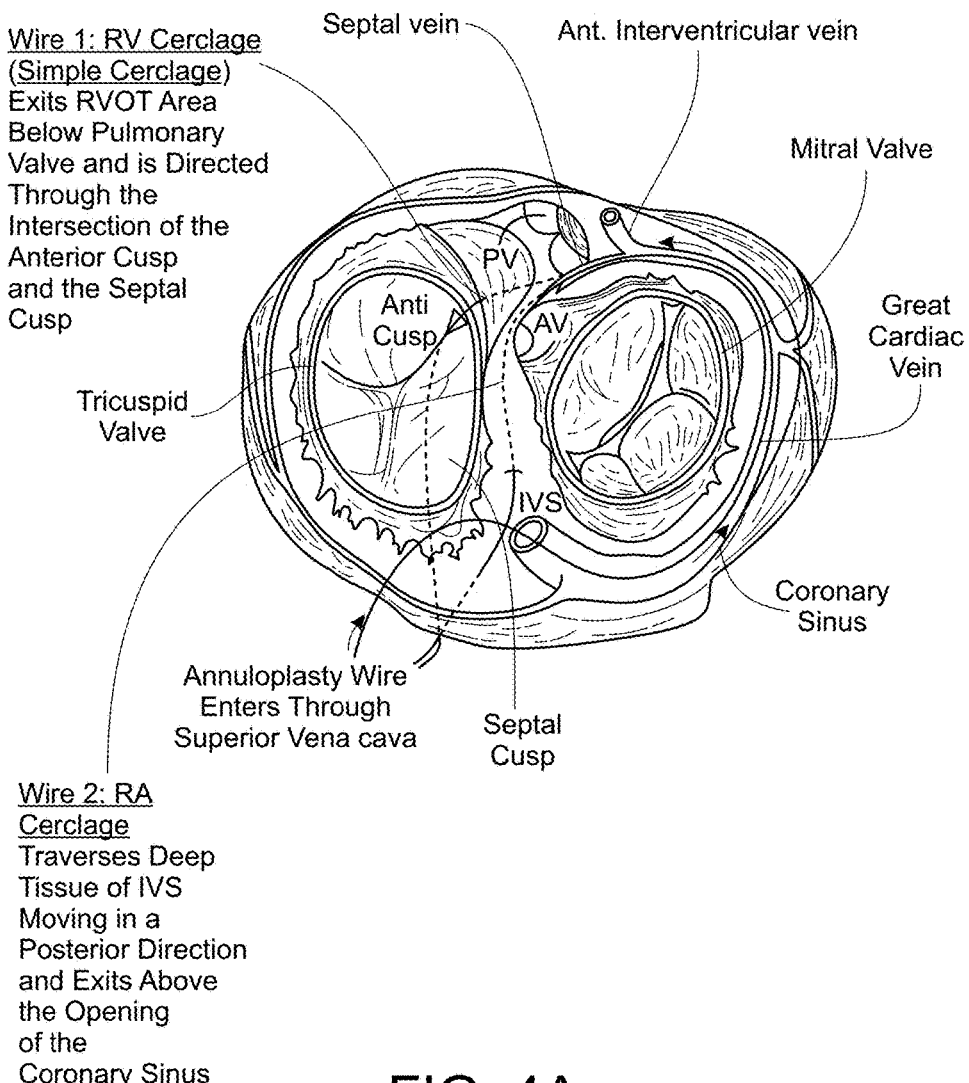
FIG. 4A is a schematic top view of a human heart, taken at the level of the atrioventricular valves, showing in dashed lines two alternative trajectories of the cerclage annuloplasty ligature around the mitral valve.
Figure 4B:
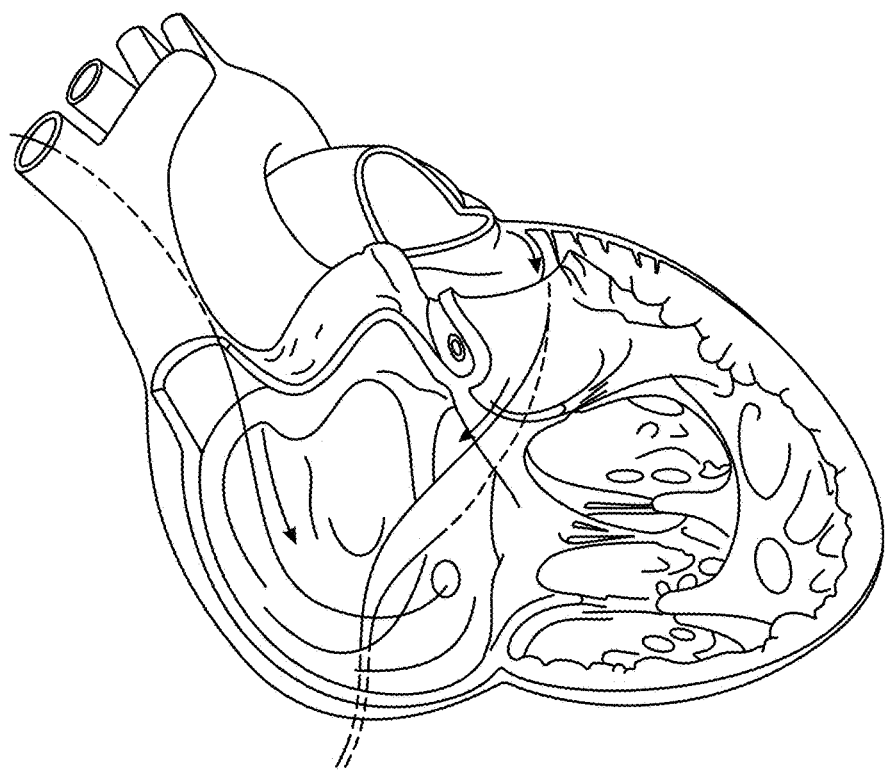
FIG. 4B is a front perspective view of the heart with portions of the myocardial wall broken away to show the cerclage annuloplasty trajectories of FIG. 4B.

Although any available approach to the coronary sinus may be used, a venous approach is preferred, for example through the jugular vein. As yet another example, the guiding catheter can be introduced into a vein, such as the femoral or jugular vein, and guided through the inferior or superior vena cava into the right ventricle of the heart. Two examples of trajectories for cerclage annuloplasty are shown in FIG. 4A and FIG. 4B. The first trajectory (labeled a "simple" or "RV" trajectory) is one in which the annuloplasty wire enters the right atrium through the superior vena cava and is then introduced through the coronary ostium into the coronary sinus. The wire is advanced through the great cardiac vein into a basal blood vessel, such as a basal septal perforator vein. The wire then exits the septal perforator vein through myocardial interstitium into the right ventricle, re-entering the right atrium along the septal tricuspid valve commissure (at the intersection of the anterior cusp and the septal cusp).

The guidewire is then retrieved using, for example, a vascular snare. Any suitable instrument can be used to capture the distal end of the guidewire and withdraw it through the vasculature until it is exposed outside the body. An illustrative preferred and improved snare system to facilitate guidewire retrieval is also described further herein at FIGS. 3E-3Y.

Figure 3E:
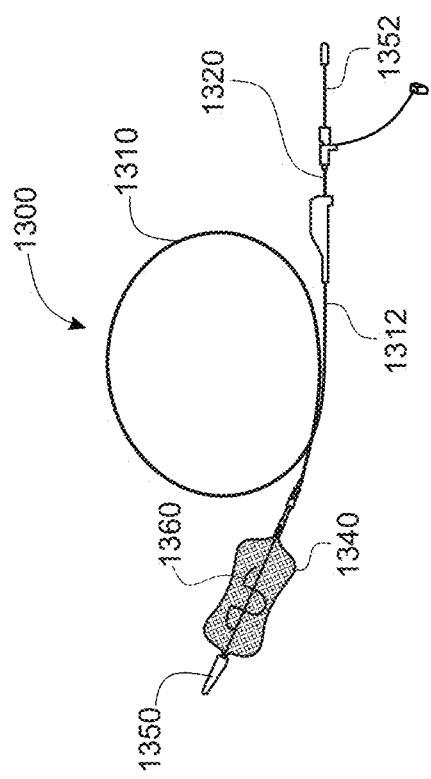
Figure 3G:
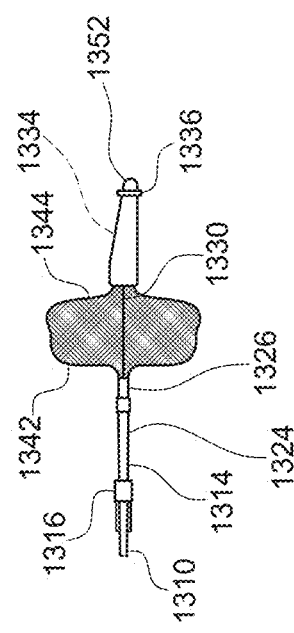

As illustrated in FIG. 3E, a snare catheter 1300 is provided defined by an elongate outer tubular member, or sheath, 1310 that slidably receives an intermediate tubular member 1320 therein along its length. The intermediate tubular member 1320, in turn, includes a further elongate inner tubular member 1330, such as a hypotube, slidably disposed therein along its length. Relative axial displacement of tubular members 1320, 1330 causes a braided snare basket 1340 to expand or collapse. Snare basket 1340 is defined by a braided surface, and has a proximal end 1342 attached to the distal end 1324 of intermediate tubular member, and a distal end 1344 attached to distal end 1334 of inner tubular member 1330. As such, when the ends 1324, 1334 are pulled away from each other by sliding tubular member 1330 distally with respect to tubular member 1320, the braided filaments of the basket 1340 are elongated and collapse radially inwardly, permitting basket 1340 to then be pulled proximally with respect to outer tubular member or sheath 1310. Inner tubular member 1330 is preferably a metallic member, such as a stainless steel or nickel-titanium alloy hypotube that defines a further lumen along its length that can accommodate a guidewire therethrough. An atraumatic conically tapering atraumatic distal tip 1350 is preferably formed over the distal end 1334 of the inner tubular member 1330 and the distal end portion 1344 of the snare basket 1340. Tip 1350 can be overmolded over these components, o it may be pre-formed and adhered to the system, such as with UV activated adhesive and the like. Preferably, tip 1350 defines a distal opening therethrough to permit a guidewire to pass therethrough after traversing the lumen defined inside inner tubular member 1330. Tip 1350 may be made from polymeric material such as PEBAX polymer, 35D Nylon material, or any other suitable atraumatic material or other material, and may be provided with a lubricious hydrophobic or hydrophilic coating as described elsewhere herein (e.g., PVP). Having tip 1350 be defined from atraumatic material facilitates passage of snare catheter 1300 through tortuous vasculature including sharp turns to arrive in the right ventricle proximate the pulmonary valve to intercept the guidewire passing through the septum wall after passing through the wall of the coronary sinus, or passing the guidewire between the target septal perforator vein and the Right Ventricular Outflow Tract (RVOT). The inner tubular member 1330 may traverse substantially the entire length of tip 1350, but preferably stops short of the distal end of tip to permit the tip to flex as it passes through vasculature.

Marker bands 1316, 1326 and 1336 are preferably formed on the distal end portions 1314, 1324, 1334 of tubular members 1310, 1320, 1330, respectively. Also, if desired, an inner target filament, or wire, 1360 may be provided having a two or three dimensional looped geometry to facilitate capture of the distal end of a guidewire passed through the wall of the septum into the region of the right ventricle near the pulmonary valve. The wire 1360 has a proximal end 1362 attached to the distal end 1324 of the intermediate tubular member and a distal end 1364 attached to the distal end 1334 of the inner tubular member 1330. The target wire 1360 further defines one or more wire loops 1366 therein laying in one or more planes. When the basket 1340 is elongated by virtue of longitudinally displacing the distal ends of relative longitudinal motion of the tubular members 1320, 1330, the target wire 1360 similarly lengthens and the loop(s) 1366 collapse.

FIG. 3I illustrates two different target wires 1360, wherein the one on the left has two loops and the one on the right includes a single loop. In either case, the wire 1360 essentially lies in a single plane. In contrast, the embodiment of FIG. 3J includes two wires, each having two pairs of loops oriented in planes that are oriented about 90 degrees with respect to one another. The purposes of the target wire 1360 is to more strongly capture the guidewire therein when the guidewire passes between the filaments of the basket 1340. Specifically, the target wire loops help capture the guidewire passing into the left ventricle after passing through the septum from the coronary sinus, and elongation and collapse of the basket 1340 and the wire loop(s) 1366 increase the capture efficiency of the snare catheter 1300 and facilitates withdrawing the basket with the captured guidewire 1340 therein proximally into the distal end 1314 of the outer tubular member 1310. FIG. 3K illustrates a variation of the wire wherein three loop-like undulations 1368 are provided that mimic the loops 1366, but are formed in more than one plane using a single filament. As depicted, two of the undulations lay in the same plane, and are separated by a third undulation 1368 that is in a second plane that is offset by about ninety degrees with respect to the plane of the other two undulations. The wire 1360 can be made from a variety of materials, such as nitinol or other material, and may be provided with a plurality of marker bands 1369 (FIG. 3K). In one embodiment, wire 1360 is formed from a composite wire, such as DFT® wire, available from Fort Wayne metals.

FIG. 3L illustrates a distal region of a snare catheter having a deployable mesh basket 1340 without an inner filament 1360. FIG. 3M illustrates such a basket, but includes a single loop filament 1360. If a DFT® wire is used, it is typically radiopaque and visible, even if the material of the basket 1340 is not. FIG. 3N illustrates a basket with two double loop wires, as illustrated in FIG. 3J, wherein the sets of double loops are oriented in different planes. FIG. 3O discloses a similar arrangement wherein one wire loop is provided on each of two filaments, wherein each loop is oriented in a different plane. FIG. 3P presents a mesh basket 1340 containing within it the wire 1360 of FIG. 3K.

FIGS. 3Q-3U present an exemplary method of using the illustrative snare catheter 1300. FIG. 3Q illustrates a snare catheter that has been fully deployed, for example, in the region of the right ventricle. A guidewire 1400 has passed through the mesh basket 1340 of the snare catheter, as well as the undulations 1368 of the wire 1360 disposed therein. Marker bands 1369 on the wire 1360 enhance visualization. FIG. 3R illustrates progressive axial elongation of the mesh basket 1340 and its contemporaneous reduction in radial dimension. FIGS. 3S-U illustrate proximal withdrawal of the basket 1340 and intermediate tubular member 1320 into the distal end 1314 of the outer tubular member or sheath. Elongation of the basket 1340 also causes the undulations 1368 in the wire to straighten out, and entangle the guidewire 1400. As the ensnared guidewire is pulled into the sheath 1310 it becomes trapped. The snare catheter 1300 can then be withdrawn proximally from the patient until the guidewire is accessible, such as by being brought externally of the patient.

Figure 3V:
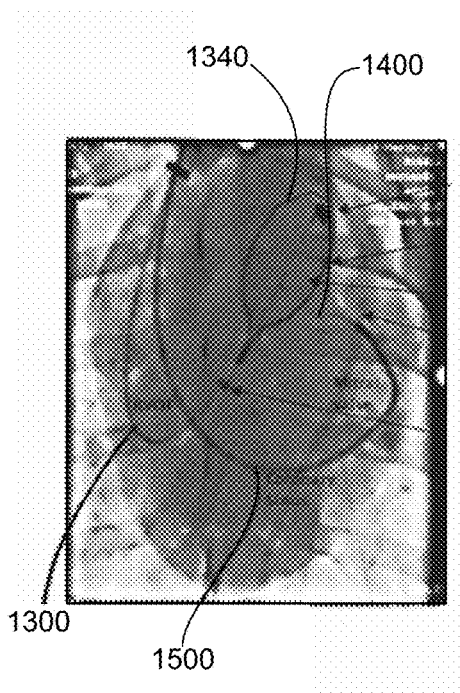
Figure 3W:
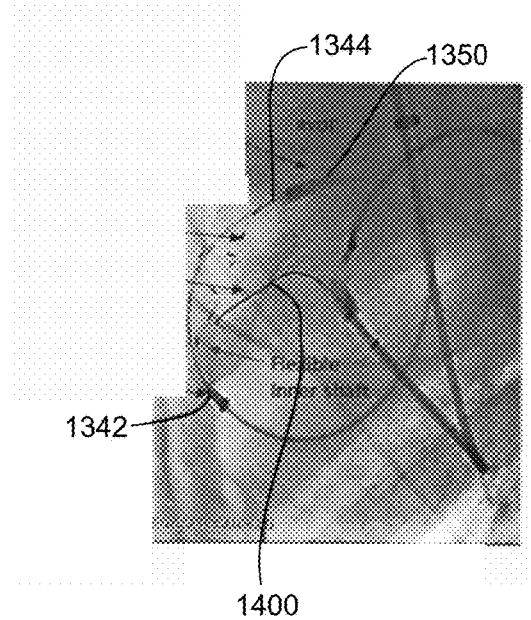
Figure 3X:
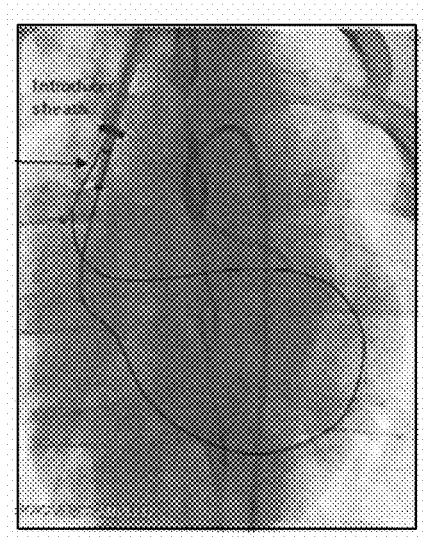
Figure 3Y:
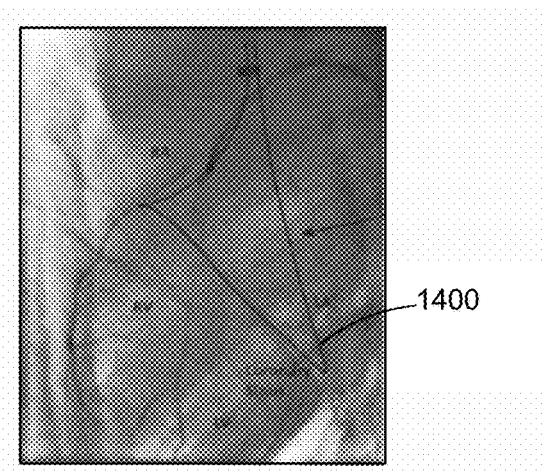

FIGS. 3V-3Y illustrate snare catheter 1300 in actual use via still images taken under fluoroscopy. FIG. 3V illustrates a guiding catheter 1500 routed into the coronary sinus, and the distal end of guidewire 1400 has passed through the septum wall such that it can be captured by the braided basket 1340 of the snare catheter 1300. FIG. 3W is an enlarged view more clearly illustrating the relative placement of the components. FIG. 3X illustrates the collapsed basket 1340 withdrawn proximally into sheath 1310, thereby trapping and grasping the guidewire 1400. FIG. 3Y illustrates the guidewire distal end having been withdrawn, as well as the guiding catheter 1500, leaving the guidewire 1400 in place following the path to be occupied later by the cerclage implant (e.g., 10) after the implant is crimped to the proximal end of the guidewire 1400 by way of crimp 70, discussed below.

After snaring the guidewire and removing the distal end thereof from the patient, the implant (e.g., 10) is exchanged for the guidewire by crimping the implant onto the proximal end of the guidewire via crimp (e.g., 70). The implant (e.g., 10) can then be advanced along the path of the guidewire as the guidewire is withdrawn from the patient until the distal end (e.g., 29) of the protection device or bridge (e.g., 20) is proximate the septum wall and the bridge is traversing the LCx artery. The location of the jeopardized coronary artery is confirmed, for example, by radiocontrast angiography. In an alternative approach, coronary veins are entered in the opposite direction from the right atrium or right ventricle under imaging guidance into a branch of the coronary sinus.

An alternative or "complex" right atrial cerclage trajectory shown in FIGS. 4A and 4B extends further posterior through the basal septal myocardium into the right atrium near the coronary sinus. The wire traverses deep tissue of the septum moving in a posterior direction and exits above the opening of the coronary sinus. The plane of the resulting cerclage annuloplasty is shown in FIG. 4C to be related to and in the plane of the coronary sinus 560 such that annuloplasty remains uniquely feasible even if the coronary sinus is remote from the mitral valve annuloplasty. As the figure indicates, the plane of cerclage 560 enhances mitral valve coaptation, even when the coronary sinus is geometrically remote from the mitral valve annulus, because it is "tilted" toward the left ventricular outflow tract. The illustrated angle α between the cerclage plane 560 and the plane of the mitral valve annulus 562 is therefore advantageous. Moreover, the illustrated trajectories of the cerclage annuloplasty induces reciprocal mitral valve coaptation and left ventricular outflow tract relaxation during ventricular systole.

The guide wire is dimensioned to operate with the guiding catheter and is usually longer than the guiding catheter. For example, a guide wire of about 100 to about 250 centimeters in length and about 0.1 to about 2 mm in diameter can be used with the guiding catheter described above. If a secondary catheter, such as a tension delivery catheter, is intended for use with the guiding catheter, that secondary catheter also is dimensioned to operate with the guiding catheter and is usually longer than the guiding catheter.

The guiding catheter can be made of any suitable material or combination of materials that provide both the strength and flexibility suitable to resist collapse by external forces, such as forces imposed during bending or twisting. Exemplary materials include, but are not limited to: polymers, such as polyethylene or polyurethane; carbon fiber; ceramic; or metals, such as nitinol, platinum, titanium, tantalum, tungsten, stainless steel, copper, gold, cobalt-chromium alloy, or nickel. The guiding catheter optionally can be composed of or reinforced with fibers of metal, carbon fiber, glass, fiberglass, a rigid polymer, or other high-strength material. In particular embodiments, the guiding catheter material is compatible with MRI, for example, braided nitinol, platinum, tungsten, gold, or carbon fiber. Additionally, the exterior surfaces of the guiding catheter can be coated with a hydrophobic material or substance, such as Teflon® or other lubricous material, such as a hydrophilic material (e.g., PVP) that aids with the insertion of the guiding catheter into the body of the subject and/or aids in the movement of the guiding catheter through the subject's body.

Additionally, the guiding catheter can include a deflectable tip, such as a simple deflectable tip having a single degree of axial freedom. Exemplary (non-limiting) fixed-fulcrum and moveable-fulcrum-deflectable-tip catheters are commercially available, such as the deflectable-tip catheters described in U.S. Pat. Nos. 5,397,321; 5,487,757; 5,944,689; 5,928,191; 6,074,351; 6,198,974; and 6,346,099, each of which being incorporated by reference herein in its entirety for any purpose whatsoever. Thus, any suitable fixed-fulcrum or moveable-fulcrum deflectable-tip catheter can be adapted for use as a guiding catheter disclosed herein. The guiding catheter also can include structures or mechanisms for aiding in the rotation of the catheter about its longitudinal axis.

The guiding catheter can include a guide collar, handgrip, handle, and other structures or devices at its proximal end that aid in operation of the guiding catheter. Various control mechanisms, including electrical, optical, or mechanical control mechanisms, can be attached to the catheter via a guide collar. For example, a guide wire can be included as a mechanical control mechanism. The guide collar can include additional operational features, such as a grip for aiding manual control of the guiding catheter, markers indicating the orientation of the guiding catheter lumen or subdivided lumens, markers to gauge the depth of guiding catheter advancement, instruments to measure guiding catheter operation or physiological signs of the subject (for example, a temperature gauge or pressure monitor), or an injector control mechanism coupled to the guiding catheter lumen for delivering a small, precise volume of injectate. In some embodiments, the guide collar contains instrumentation electrically coupled to metallic braiding within the guiding catheter, thus allowing the guiding catheter to simultaneously be used as a receiver coil for MRI.

A guide wire used with the system for guiding the guiding catheter into and through a subject's body can be composed of any suitable material, or combination of materials, including the materials described above in relation to the guiding catheter. Exemplary (non-limiting) guide wires are composed of material having the strength and flexibility suitable for use with the device, such as a strand of metal (for example, surgical stainless steel, nitinol, platinum, titanium, tungsten, copper, or nickel), carbon fiber, or a polymer, such as braided nylon. Particular (non-limiting) guide wires are composed of a strand of Nitinol or other flexible, kink-resistant material. The guiding catheter or guide wire can include an image-enhancing feature, structure, material, or apparatus, such as a radiopaque marker (for example, a platinum or tantalum band around the circumference of the guide wire) adjacent its distal end. As another example, the guide wire can include etchings or notches, or be coated with a sonoreflective material to enhance images obtained via intravascular, intracardiac, transesophogeal, or other ultrasound-imaging methods. As another example, the guide wire can be coated with a T1-shortening or T2-shortening agent to facilitate passive visualization using MRI. As yet another example, a fiber-optic secondary catheter can be inserted into and through a secondary-catheter lumen of the guiding catheter to assist in visualizing the position of the guide wire within the subject as a guide wire is deployed through the distal guide-wire lumen port. In some embodiments, the guide wire and/or guiding catheter includes a structure, apparatus, or device at its distal tip useful for penetrating tissue, such as myocardial skeleton, muscle, or connective tissue. For example, the distal tip of the guide wire can be sharpened to a point for puncturing through tissue, or a secondary catheter having a coring mechanism or forceps at its distal tip can be used in conjunction with the guiding catheter. In alternative embodiments, the guide wire can deliver radiofrequency or laser ablative energy to assist with traversal of tissue. However, in alternative embodiments, the distal end of the guide wire is bent to provide a J-shaped or a pigtail-shaped tip to protect against perforation of tissue by the guide wire during manipulation. In still other alternative embodiments, the guide wire itself has a deflectable tip to facilitate traversal of tissue irrespective of natural tissue planes. One or more secondary catheters can be deployed within the lumen of the guiding catheter. Like the guiding catheter, each secondary catheter has a proximal end and a distal end; however, not all secondary catheters have a lumen. For example, non-lumen secondary catheters can include various probes, such as temperature probes, radiofrequency or cryogenic ablation probes, or solid needles.

An exemplary non-limiting secondary catheter is a canalization needle catheter, which can be deployed through the guiding catheter and into a chamber of the heart to place cerclage annuloplasty ligature through the coronary sinus around the mitral valve. A canalization-needle catheter is a type of secondary catheter that can be used to apply a suture to a bodily tissue, organ, or structure of interest.

C. Application of Tension

Tension is applied via the annuloplasty cerclage through the sheath material 50, which is preferably a hollow braided suture material as described above. Tension can be applied to both ends of the sheath 50 as they are externalized at the point of vascular access in concert with a lock delivery catheter as described in further detail below that directs both ends of the suture through a lock mounted at the end of the lock delivery catheter. Tension can be applied under imaging guidance to the tethers through the lock at a distal end of the lock delivery catheter until the desired degree of mitral annular circumferential reduction is accomplished, or until the mitral valve regurgitation is reduced, or until other deleterious endpoints are achieved such as mitral valve inflow obstruction. Tension in the sheath 50 can then be secured by locking the lock of the lock delivery catheter such as that described in copending U.S. patent application Ser. No. 14/074,517, filed Nov. 7, 2013, or the lock delivery catheter described below with reference to FIGS. 14-20 herein. Alternatively, a knot may be tied and pushed through a guiding catheter. The lock or knot, as desired, can be located at the right atrium or right ventricle where the two cerclage trajectories cross, or at the point of vascular access, or in between the two. Tension can thus be delivered, if desired, by counterpressure against the fixation device, for example, applied through a delivery catheter. Before fixation, tension can be released or reduced, for example, to reposition the protection device or to achieve a lower degree of mitral annular circumferential reduction.

As tension is applied, valvular regurgitation is preferably assessed repeatedly and non-invasively by an appropriate imaging technique. Such imaging techniques include X-ray angiography, electromagnetic position detection, MRI, external or intracavitary or intravascular ultrasound, X-ray computed tomography, pressure transducers in an affected chamber such as the left atrium or the pulmonary vein or the pulmonary artery, or a "fusion" or combination of any of the above. After the valvular regurgitation has been reduced (or even eliminated) and a desired tension is achieved, the tension is fixed using a lock or knot delivery system as mentioned above, and the excess sheath material proximal to the lock or knot can be cut and removed in any desired manner. In accordance with one aspect of the disclosure a cutting instrument can be used as described further below with reference to FIGS. 21-22 herein.

If the resulting circumferential sheath 50 is knotted to form a closed loop, the sheath 50 essentially becomes a cerclage suture. Without further elaboration, it is believed that one skilled in the art can, using this description, utilize the present discoveries to their fullest extent.

The use of the implant with protective device (e.g., 20) has been disclosed for use in a cerclage annuloplasty technique. However, the disclosed implants can be used with any other annuloplasty device that extends even partially through the coronary sinus in a region that crosses an underlying coronary artery. For example, the protective device (e.g., 20) can be used to protect against compression of coronary arteries with any coronary sinus annuloplasty device, such as the coronary sinus device in U.S. Pat. No. 7,090,695 or the inflatable coronary sinus device shown in U.S. patent Ser. No. 10/787,574 (U.S. Patent Publication No. 2004/0254600). Although these devices are designed for endovascular delivery, the protection device disclosed herein can also be used with annuloplasty devices that are implanted using an open-chest surgical repair instead of a catheter based approach. The problem of coronary artery compression is also encountered with these devices, and the protective device disclosed herein may be used to avoid that problem. Hence the presently disclosed embodiments are not limited to a protective device for use with cerclage annuloplasty, nor is it limited to use of the device with catheter based delivery techniques.

When used with a coronary sinus annuloplasty implant of any kind, the protective device (e.g., 20) can be provided as an integral part of the implant (e.g. 10) or as a separate device suitable for placement between the implant and an underlying coronary artery to be protected. When provided as an integral part of the implant, the implant is positioned in the coronary sinus so that the arch of the support extends over the underlying coronary artery. In alternative embodiments the protection device can be provided as a separate device that is advanced through a catheter system until it is positioned over the coronary artery to be protected.

A mitral cerclage annuloplasty device, as described herein, can push heart tissue radially inwardly and create a retaining structure projecting into the heart near the native mitral valve region to allow implantation and securement of a prosthetic transcatheter mitral valve (TMV). As used herein, the terms prosthetic mitral valve, transcatheter mitral valve, TMV, prosthetic mitral device, prosthetic mitral implant, and the like, include any prosthetic device implantable within or adjacent to the native mitral valve region, including valved devices and as well as devices that do not include a valve component (e.g., frames, stents, rings, fasteners, tethers, portions of a valved device, etc.). In some embodiments, cerclage annuloplasty can create an internal ridge, landing zone (as described herein above), fixation plane, etc. (referred to herein generally as a "retaining structure") for a TMV to be secured.

The TMV secured to the retaining structure within the heart can comprise a radially compressible and radially expandable prosthetic device that is delivered into the heart in a radially compressed state using a transcatheter, transvascular delivery approach, for example. Once inside the heart, the TMV can expand, either using applied expansion force (e.g., an inflatable balloon) or using intrinsic self-expanding materials (e.g., nitinol) that cause the TMV to self-expand upon removal of a compressive force applied during delivery. Upon expansion, the TMV can become secured to the retaining structure created by the mitral cerclage annuloplasty device to inhibit the TMV from migrating out of position within the heart. For example, the TMV can comprise a tubular frame that expands around both sides of the retaining structure and/or clamps onto the retaining structure.

When expanded, the implanted TMV can apply a radially outward force on the heart tissue. This radially outward force can undesirably compress blood vessels in the heart tissue and cause constriction and reduced blood flow. At the same time, the radially inward force applied by the mitral cerclage annuloplasty device can also undesirably compress blood vessels in the heart tissue from the outside. This dual compression on the cardiac blood vessels can exacerbate the risk of ischemia, heart attack, and other complications. Of particular concern are the circumflex coronary artery and its marginal branches near the great cardiac vein, which can between the implanted TMV and the surrounding mitral cerclage annuloplasty device. Accordingly, protection devices as disclosed herein can help protect such blood vessels from compression from both the outside-in (via the mitral cerclage annuloplasty device) and from inside-out (via the TMV).

Figure 6:
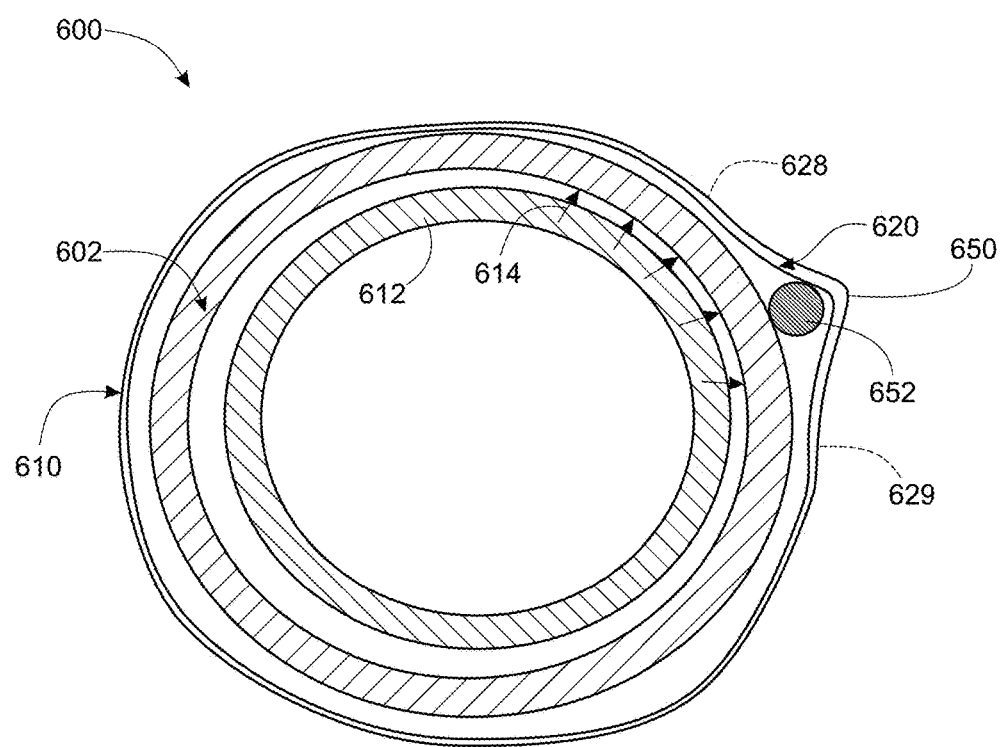
FIG. 6 is a schematic cross-sectional view of the mitral valve region of a heart wherein a prosthetic heart valve is positioned within the mitral valve region and applies an outward expansion force and a mitral cerclage implant in accordance with the disclosure is positioned around the mitral valve region and applies an inward force, and a coronary protection device in accordance with the disclosure is positioned along the mitral cerclage device to protect the coronary artery from being compressed.

FIG. 6 is a schematic cross-sectional view of the mitral valve region of a heart showing an exemplary implant system 600 that includes an implanted TMV 612 positioned within the heart wall 602 and a mitral cerclage annuloplasty device 610 positioned around the heart wall. The device 610 includes an arched protection device 620 spanning over a coronary artery 652 to protect the artery from compression applied by both the device 610 from the outside and outward expansion force 614 applied on the inside of the heart wall 602 by the TMV 612. The exemplary protection device 620 includes an arched portion extending between two flattened, generally coplanar proximal and distal segments 628, 629. The bridge, or protective device 620 can have any combination of features and dimensions described herein with regard to other exemplary protection devices.

Figure 7:
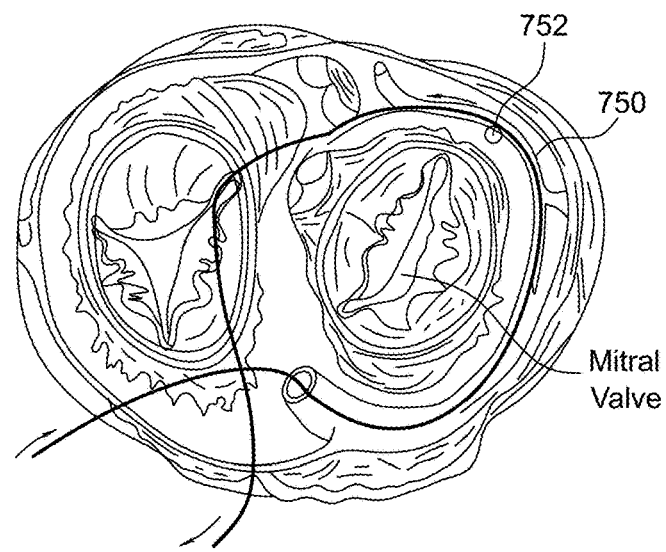
FIG. 7 is a cross-sectional view of a heart with a mitral cerclage device being delivered through the coronary sinus and around the mitral valve.

FIG. 7 shows a tensioning suture (e.g., 50) extending through the coronary sinus 750 partially around the mitral valve without the inclusion of the disclosed protection device. Consequently, the circumflex coronary artery 752 is entrapped under the tensioning suture as the coronary sinus overlaps the artery, applying unwanted compression on the artery. When a TMV is also implanted within the mitral valve, it can apply additional inside-out compression force on the artery 752. Without the protection device, the artery 752 can collapse and/or be pinched by the opposing forces.

Figure 8:
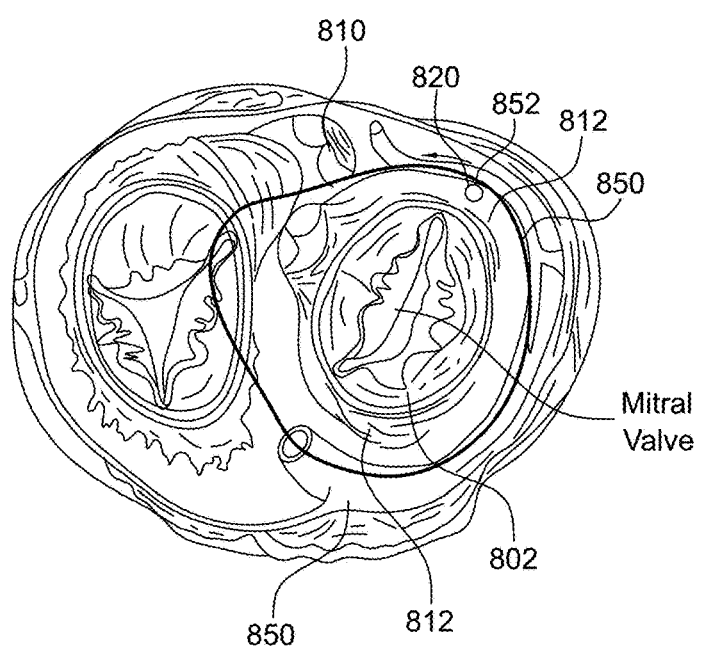
FIG. 8 is a cross-sectional view of a heart with a prosthetic mitral valve mounted within the native mitral valve region and a mitral cerclage device positioned through the coronary sinus and around the mitral valve region with a protection device protecting the coronary artery from compression.

FIG. 8 shows the approximate locations of the disclosed mitral cerclage annuloplasty device 810 and an exemplary TMV 812 when implanted. As illustrated, the protection device 820 can bridge over the artery 852 (at least partially) and protect it from compression (at least partially) from both the tensioning member on the outside and the TMV on the inside of the heart wall 802. FIG. 8 illustrates the use of a protection member 820 that has an arch portion sized to extend over only about half of the radial thickness of the artery 852, leaving the artery partially exposed to compression. In the illustrated arrangement of FIG. 8, the radially inner half of the artery 852 can be compressed by the opposing forces of the tensioning member and the TMV, leaving the artery partially compressed. In other embodiments, the radial height of the arch can be larger (e.g., at least as large as the maximum radial diameter of the artery) to accommodate the most of, or all of, the radial thickness of the artery 852, thereby protecting the artery from compression to a greater degree (e.g., completely or substantially completely) compared to what is shown in FIG. 8. For example, the height of the arch can be at least 3.5 mm. The retaining structure created within the heart by the mitral cerclage annuloplasty device can be oriented in a different plane from an annular or supraannular mitral valve annuloplasty ring or band, whether implanted using surgical techniques or using transcatheter techniques.

Figure 5:
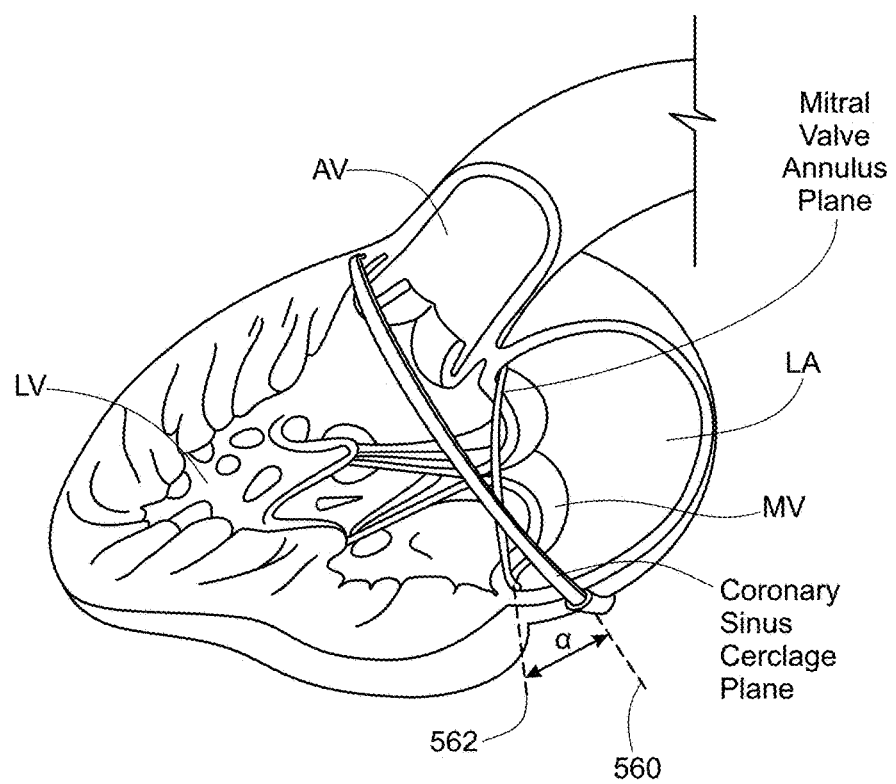
FIG. 5 is a rear perspective view of the heart showing the tilted plane of the coronary sinus cerclage annuloplasty. The drawing schematically illustrates a smaller traditional surgical mitral valve annuloplasty ring over the mitral valve annular plane and the larger coronary artery cerclage in a plane that is tilted to the mitral plane so as to encompass the left ventricular outflow tract.

An example of discordant cerclage and mitral annular planes is illustrated in FIG. 5. The retaining structure created by the disclosed mitral cerclage annuloplasty can be non-circumferential in part because of the discordant cerclage and annular planes. However, as shown in FIG. 8, the retaining structure can extend around more than half of the full circumference of the mitral valve region so that a TMV can be assured fixation to the retaining structure without undesirable displacement or migration of the TMV.

Figure 9:
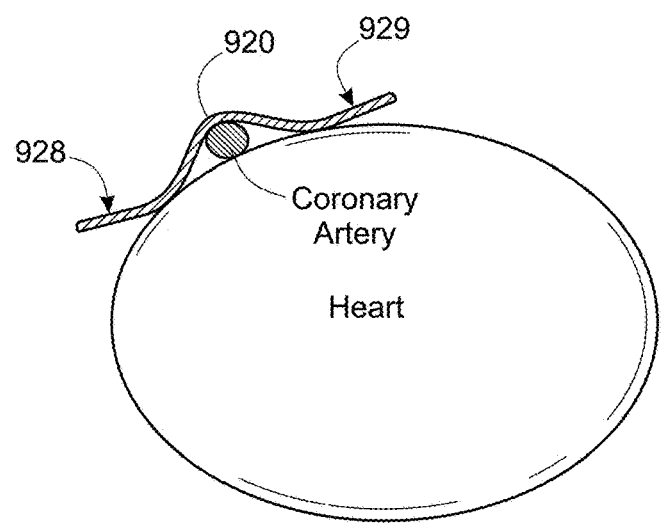
FIG. 9 illustrates an embodiment of a protection device with an upwardly extended central arch that is improperly configured.
Figure 10:
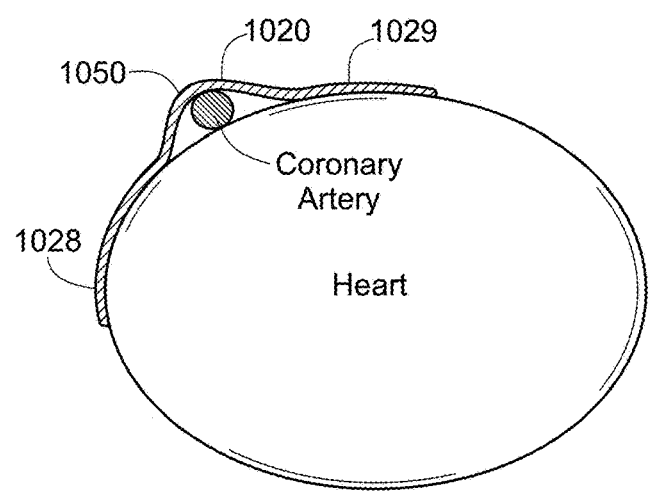
FIG. 10 illustrates an embodiment of a protection device with an upwardly extended central arch that is properly configured.

As discussed, a protection device configured to protect against "inside-out" compression of an entrapped coronary artery can have an increased arch height to more fully protect the artery. However, the increased height can lead to proportionally longer arch length (compared to the length of the protection device) unless the height-to-length ratio is increased. As shown in FIG. 9, this can create an undesired effect where the proximal and distal regions 928, 929 of the protection device 920 bend upwardly causing stress concentrations at the bottom of the central, arched region of the protection device 920 that poke into the myocardium and exert a more concentrated compression force right next to the coronary artery rather than having the compression force evenly distributed along the proximal and distal regions 928, 929 of the protection device 920. As shown in FIG. 10, embodiments of the feet, or proximal and distal regions 1028, 1029 of the protection device 1020 can include a curvature along the main longitudinal axis of the protection device 1020 to allow it to better conform to the curved wall of the heart. This allows a greater height to the coronary artery while avoiding focused compression at the points of contact of the arch elbows along the myocardium immediately alongside the coronary artery. That focused compression limits the protective effect of the arch and may cause undesirable compression or injury or erosium to the myocardium. The curve conformation of the rigid protection member can redistribute the radial force imparted by cerclage tension to better effect protection of the entrapped coronary artery.

Figure 11:
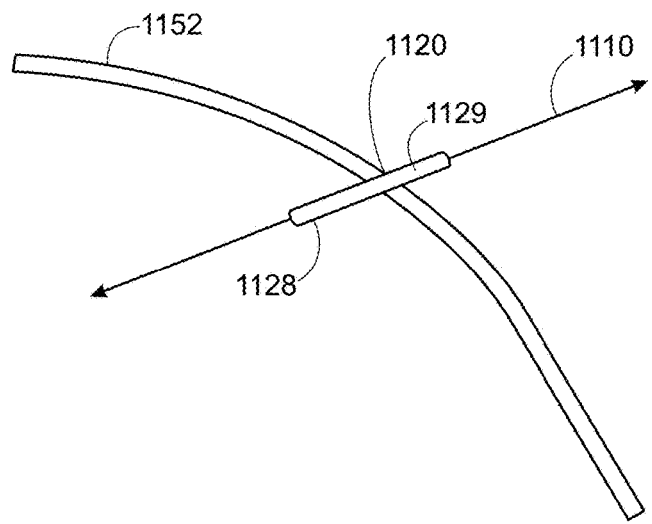
FIG. 11 illustrates an oblique crossing angle as the mitral cerclage device and protection member pass over the coronary artery.

Some embodiments of the protection member can have an asymmetric chirality. For example, the protection member can have a helical or corkscrew shape along is longitudinal axis such that it has a three dimensional curvature, rather than the previously described two dimensional curvature. More generally, the protection member can have a three-dimensional or multi-planar curvature, at least along the arch portion. The asymmetric chirality or multi-planar curvature of the protection member can address the problem of the oblique crossing angle of the cerclage tension device with respect to the underlying coronary artery (see FIG. 11). With an symmetrical arched protection member 1120 that appears linear when viewed from above the arch (as shown in FIG. 11), the oblique crossing angle reduces the effective width of the arch and reduces its ability to protect the coronary artery 1152 against compression.

Figure 12:
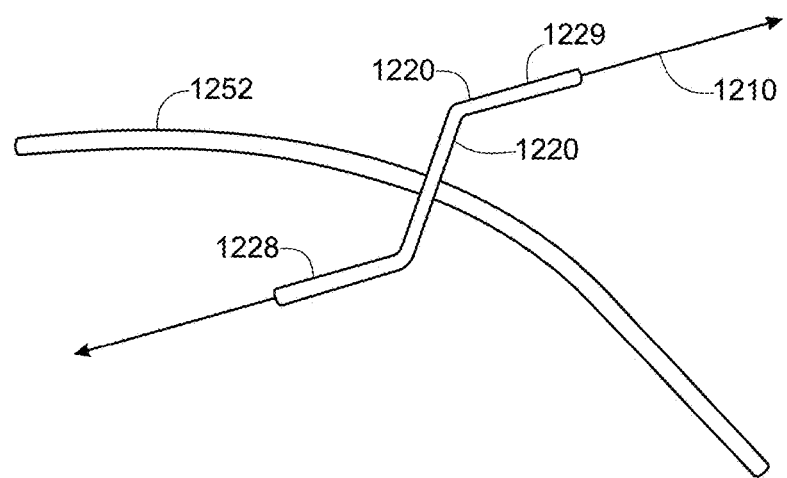
FIG. 12 illustrates an exemplary protection device having a chiral shape that allows it to cross at an angle perpendicular to the coronary artery.
Figure 13:
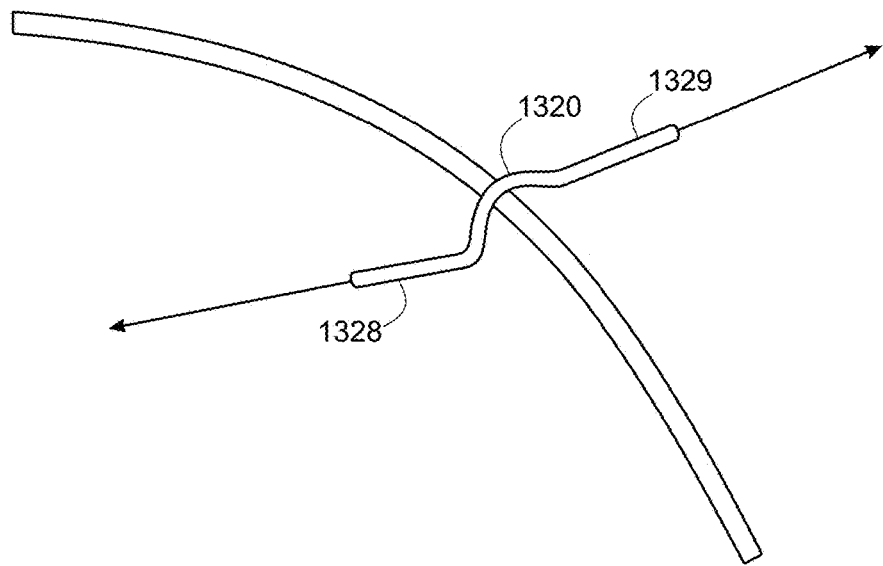
FIG. 13 shows another exemplary protection device having a chiral shape that includes a three-dimensional curvature.
Figure 15A:
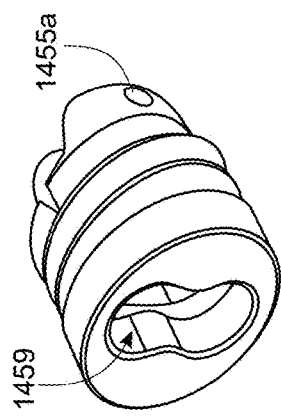
FIGS. 15A-15F illustrate aspects of a lock for delivery using the delivery system of FIG. 14.
Figure 15B:
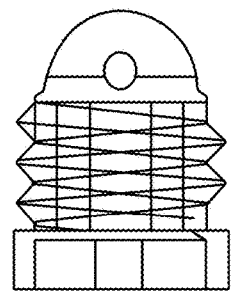
Figure 15C:
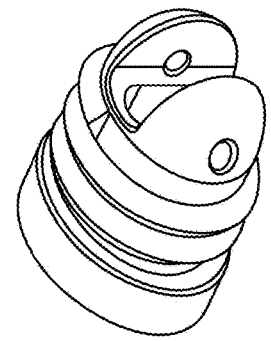
Figure 15D:
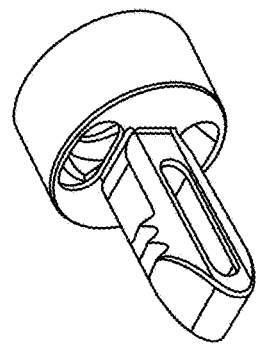
Figure 15E:
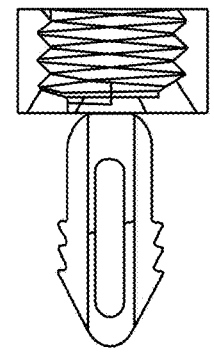
Figure 15F:
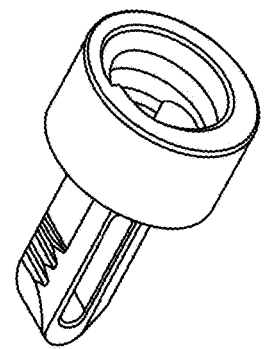

FIG. 12 illustrates an exemplary chiral shaped protection member 1220 that curves laterally as it arches over the coronary artery 1252 and then curves back the other lateral direction such that the two feet 1228, 1229 appear generally parallel but offset when viewed from above the top of the arch (e.g., radially inwardly). This allows the arched portion to cross the coronary artery 1252 nearly perpendicularly rather than at an oblique angle as shown in FIG. 11. FIG. 13 shows another exemplary chiral shaped protection device, or bridge, 1320 from a partial elevation view, showing an asymmetric chiral shape. The bridge 1320 can have a three-dimensional curvature that curves up and over the artery and also curves laterally side-to-side to provide a shorter, more efficient crossing of the artery while keeping the feet 1328, 1329 oriented along the coronary sinus and facing inward toward the mitral valve.

FIGS. 14A and 14B illustrate aspects of a lock delivery system in accordance with the disclosure. For purposes of illustration, and not limitation, the lock delivery system 1410 includes a delivery catheter having a proximal end and a distal end with a lock 1450 attached to its distal end. More specifically, lock delivery system 1410 includes an outer tubular member 1420 having an inner tubular member 1430 disposed therein. The outer tubular member 1420 includes a proximal end 1422 attached to a glanded, hemostatic delivery device hub 1425 with a flush port for flushing an annular space defined between tubular members 1420, 1430, and a distal end 1424 including an outer internally threaded (female) fastener 1427 incorporated thereto for receiving threaded fastener portion 1457 of outer portion 1455 of lock 1450. Inner portion 1452 of lock 1450 includes external threading 1454 to mate with externally threaded fastener 1439 formed at the distal end 1434 of inner tubular member 1430. While fasteners 1427, 1454, 1439, 1457 are disclosed as being threaded fasteners, any suitable fastener can be used. The inner tubular member 1430 is slidable within elongate outer tubular member 1420. Elongate lumen 1435 defined along the interior of inner tubular member 1430 is configured to receive sheath/tethers (e.g., 50) therethrough of implant (e.g., 10). Inner and outer portions 1452, 1455 of lock 1450 are coupled by a limiting pin 1451 that is affixed to and extends transversely across outer portion 1455 of lock 1450 received by openings 1455a, and extends through an elongate slot 1458 defined in elongate distal portion 1456 of the inner portion 1452 of lock. In use, barbs 1452a disposed on inner portion 1452 of lock 1450 wedge tethers (e.g., 50) against inner passage 1459 of outer portion 1455 of lock. The tethers/sutures/sheath 1450 are also routed through longitudinal openings 1452b defined on inner portion 1452 of lock 1450.

Inner tubular member 1430 can be made from any suitable material, preferably a polymeric material such as PEEK. Outer tubular member 1420 is preferably provided as a braided catheter material, such as a polymeric co-extrusion including a braided layer. The threaded connection between fastener portion 1452 and inner tubular member 1430 permits attachment of the two components to each other to thereby permit remote opening and closing of the lock, as well as permitting the lock to be removed and retrieved, if desired, even after full deployment of the lock.

FIGS. 15A-15F illustrate aspects of the illustrated lock 1450 for delivery using the delivery system 1410 of FIG. 14. As illustrated, inner portion 1452 of lock includes a proximal generally annular shaped body that is internally threaded along its center to define a central passage. This central passage is in fluid communication with openings 1452a defined on either side of elongate distal portion 1456 of the inner portion 1452 of lock for the routing of the tethers. Elongate slot 1458 passes laterally through laterally opposed sides of elongate distal portion such that the slot defines a generally rectangular volume to permit sliding engagement with pin 1451 that passes laterally therethrough. The relative axial displacement possible between outer portion 1455 and inner portion 1452 of lock is delimited by the length of slot 1458 as the pin 1451 is configured to butt up against either end of slot 1458. Moreover, the coupling provided by pin 1451 and slot 1458 also provides that the inner 1452 and outer 1455 portions of the lock 1450 cannot be rotationally displaced with respect to each other. This permits the application of torque to both portions of the lock 1450 at the same time by rotation of inner tubular member 1430 with respect to outer tubular member 1420.

The components of lock 1450 are preferably composed of metallic material such as stainless steel. The threaded connection connecting outer lock portion 1455 and outer tubular member 1430 provides suitable control for securing the lock 1450 in place while activating the lock 1450. Routing each sheath/suture (e.g., 50) through openings 1452a help ensure that the sheath material does not interfere with movement of the inner tubular member 1430, which is advantageous as inner tubular member 1430 rides over the sutures both when attached and detached from inner lock portion 1452.

Figure 16D:
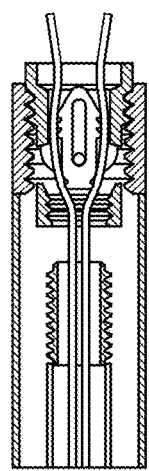
FIGS. 16A-16E illustrate further aspects of use of the lock delivery system in accordance with the disclosure.
Figure 16E:
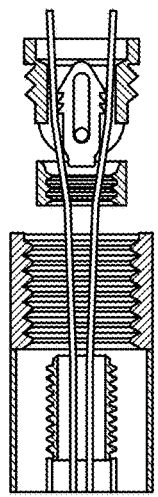
Figure 16A:
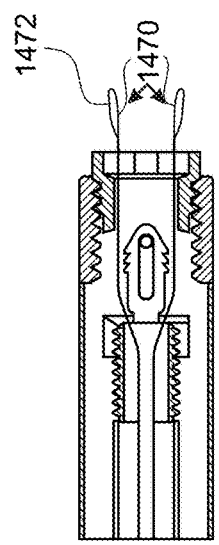
Figure 16B:
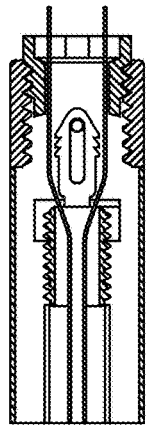
Figure 16C:
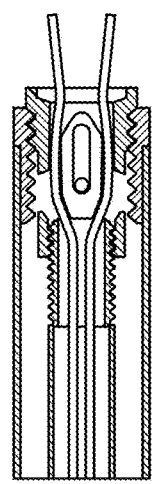

FIGS. 16A-16E illustrate further aspects of use of the lock delivery system in accordance with the disclosure. FIG. 16A depicts a first step of threading the lock delivery system 1410 by introducing a pair of snaring sutures 1470, each defining a distal loop 1472 for receiving tether material (e.g., 50) therethrough. This step is accomplished with the lock in an "open" position whereby the inner and outer lock portions 1452, 1455 are relatively longitudinally separated such that the pin 1451 resides at a distal end of the slot 1458. Each end of the suture/sheath material (e.g., 50) of implant (e.g., 10) is threaded through a respective distal loop 1472 of a respective snaring suture 1470 and withdrawn proximally through the lumen of inner tubular member 1430, after the removal of core wires (e.g., 30, 40) of implant (e.g., 10), as depicted in FIG. 16B. The distal end of system 1410 is then advanced distally, riding over the tethers (e.g., 50) of the implant (e.g., 10) to a location where the lock 1450 is to be delivered to maintain tension on the implant (e.g., 10) to reshape the mitral valve, for example. As depicted in FIG. 16, once the lock is in the correct location within the heart to apply tension the implant is tensioned by pulling the tethers/sutures proximally until the desired tension is applied. The inner tubular member 1430 is then advanced distally with respect to the outer tubular member 1420 to cause pin 1451 to slide distally within slot 1458, bringing barbs 1452a to urge the tethers/sutures against the inner wall of the central bore in outer lock member 1455, thus trapping the tethers/sheath material in place, under tension. Next, as depicted in FIG. 16D, the inner tubular member is detached from the inner portion 1452 of the lock 1450, in this embodiment, by detaching the threaded connection between the two components. The final step, as depicted in FIG. 16E, is to release the outer lock portion 1455 from the outer tubular member 1420 by uncoupling the threaded connection between the two components and preferably pulling the inner and outer tubular members proximally in a passive manner so as to not disturb the lock 1450 that is now fixed in position.

Figure 17:
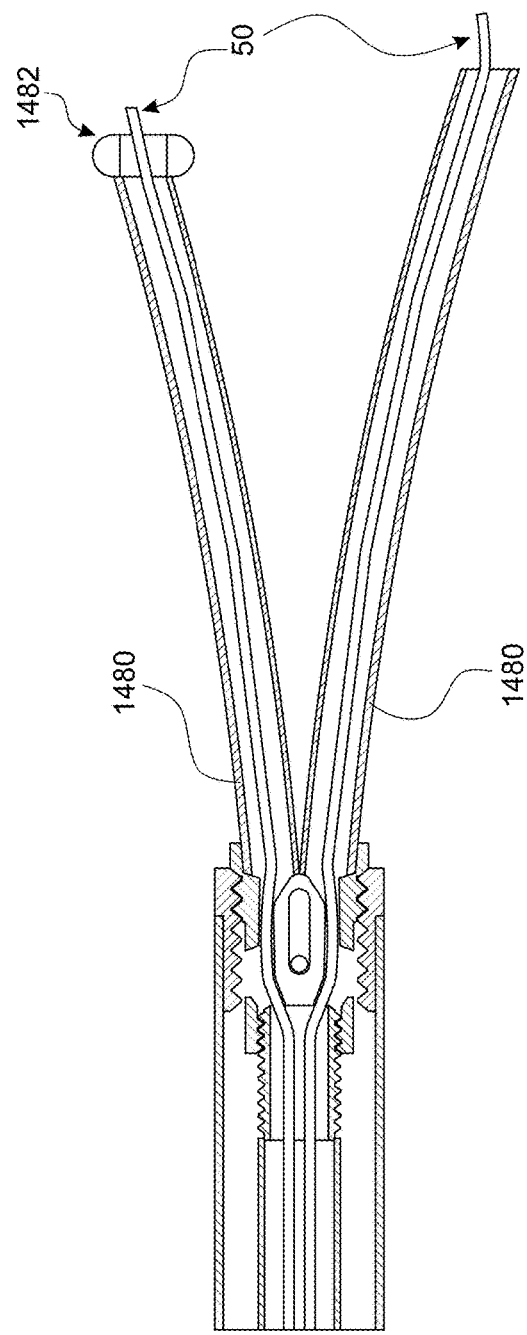
FIG. 17 illustrates a further embodiment of a lock in accordance with the disclosure including strain relief segments.

FIG. 17 illustrates a further embodiment of a lock in accordance with the disclosure including strain relief segments. While not required, in the specific context of a mitral cerclage procedure as described herein, it can be useful to provide strain relief segments 1480, or protection elements, that are attached at a proximal end to outer portion 1455 of lock 1450. In the illustrated embodiment, outer portion 1455 of lock 1450 includes a distal opening having a figure-eight shaped perimeter, wherein each half of the opening is sized to receive a strain relief/protection member 1480 that may, if desired, be provided with a protection ball 1482 at a distal end thereof. As such, the lock 1450 could be supplied without protection elements 1480, or with one or two such elements, which may, if desired, be supplied with a distal protection ball 1482. Protection elements 1480 help distribute the load imposed by applied tension to the sheath/tether material over a larger surface area in the coronary sinus and other tissues, for example, thereby reducing the chances of tissue damage arising from the cerclage procedure. With reference to FIGS. 1P and 1Q, in one embodiment, the length of segments 1480 and extensions 428b, 429b are sufficient to overlap to some extent to provide a robust structure that can be used to facilitate implantation of a partial or full replacement mitral valve, for example. Legs 1480 can be a coiled metallic, plastic or composite material, or can, if desired, be comprised of a flexible polymer sleeve.

Figure 18:
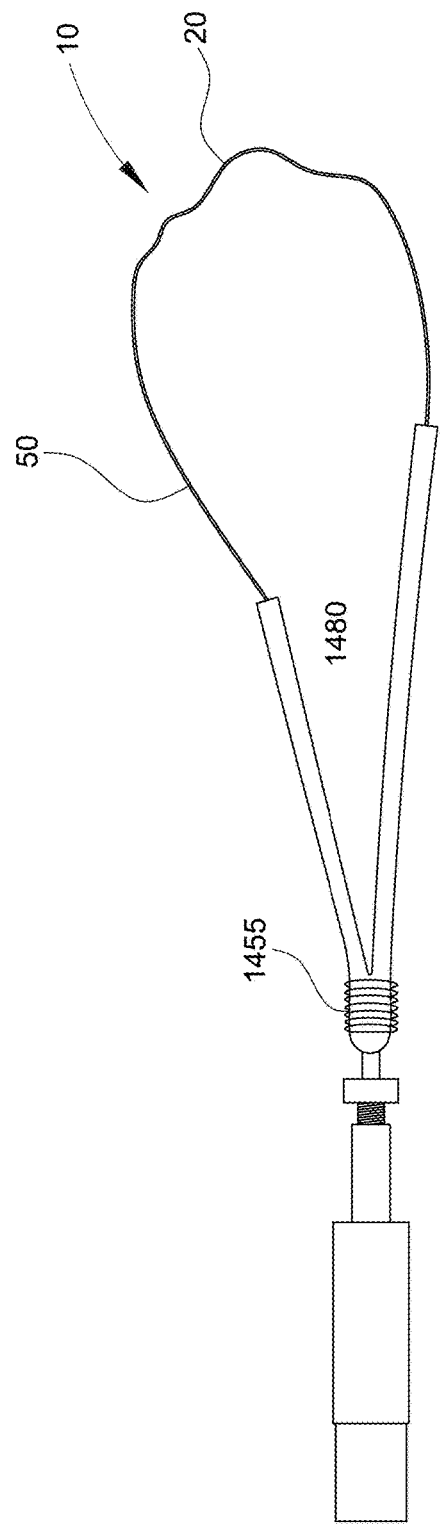
FIG. 18 illustrates the lock delivery system coupled to an exemplary cerclage implant.

FIG. 18 illustrates the lock delivery system 1410 coupled to an exemplary cerclage implant. In this embodiment, a lock 1450 including protection elements 1480 without protection balls 1482 is shown with sutures 50 of implant routed therethrough after removal of the core wires 30, 40. The implant 10 in cooperation with the lock 50 provide a full circumferential structure for maintaining tension on the mitral valve after the cerclage procedure is completed.

Figure 19A:
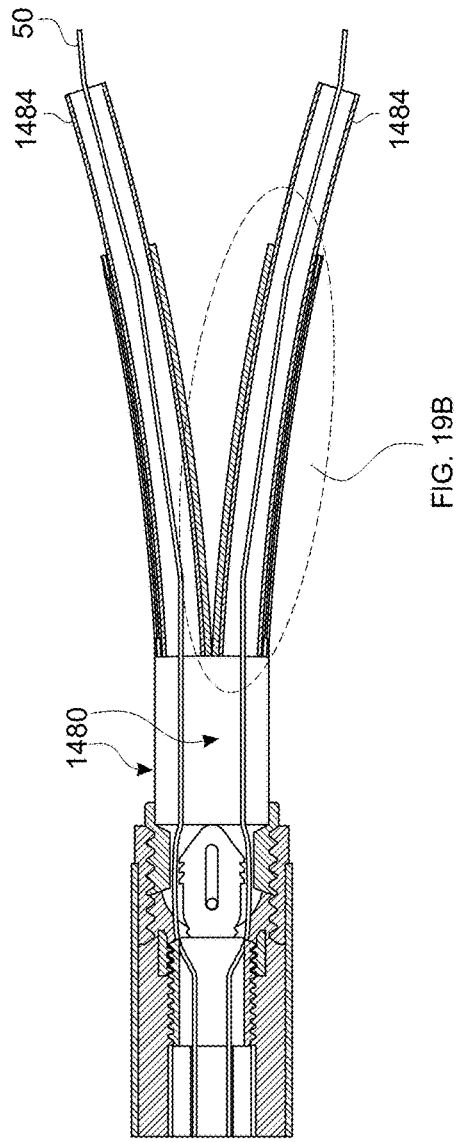
FIGS. 19A-19B illustrate further aspects of the strain relief of the disclosed illustrative lock in accordance with the disclosure.
Figure 19B:
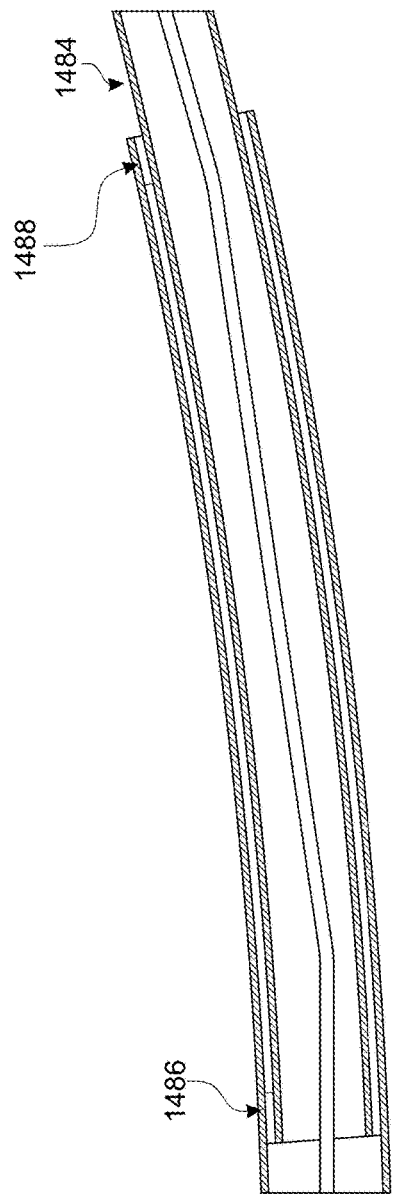

FIGS. 19A-19B illustrate a further embodiment of the protection element or strain relief 1480 of the disclosed illustrative lock in accordance with the disclosure. In this embodiment, the strain relief or protection legs 1480 are further provided with a telescoping distal sleeve 1484 that is slidably received within each leg 1480. As depicted, each inner telescoping sleeve includes a stop, or boss 1484 formed on an external proximal surface thereof. Each leg 1480 further includes a distal stop 1488 formed on an inner distal surface thereof. In use, stops 1486, 1488 contact each other, preventing sleeve 1484 from falling out from sleeve 1480 by physically contacting and interfering with each other. Sleeve 1484 is preferably made out of a flexible material that can be the same type of material as leg 1480.

Figure 19C:
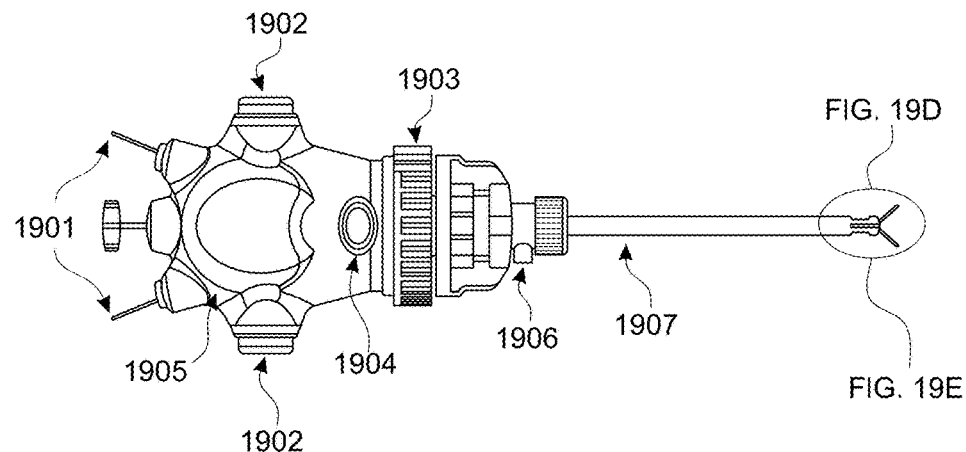
Figure 19D:
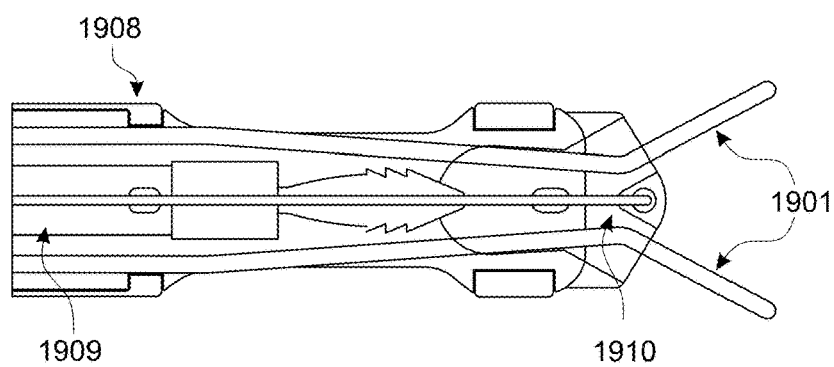
Figure 19E:
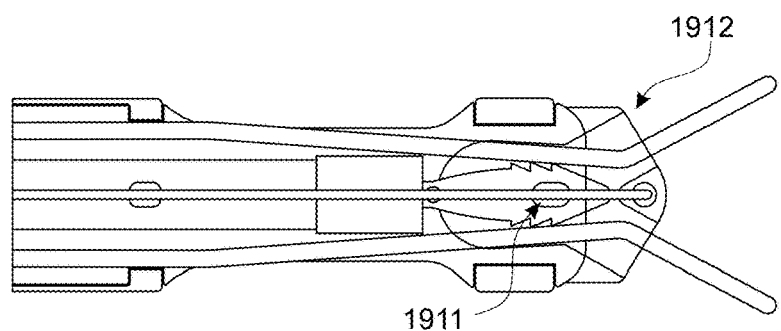
Figure 19F:
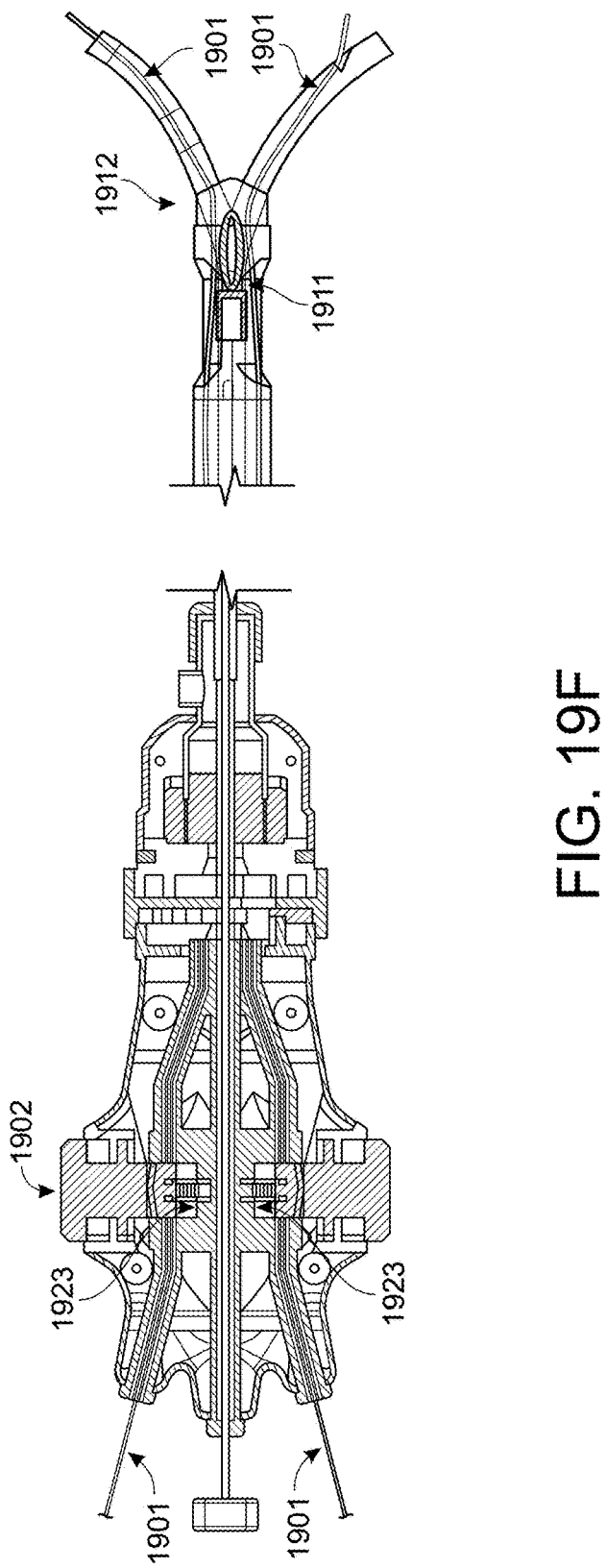
Figure 19G:
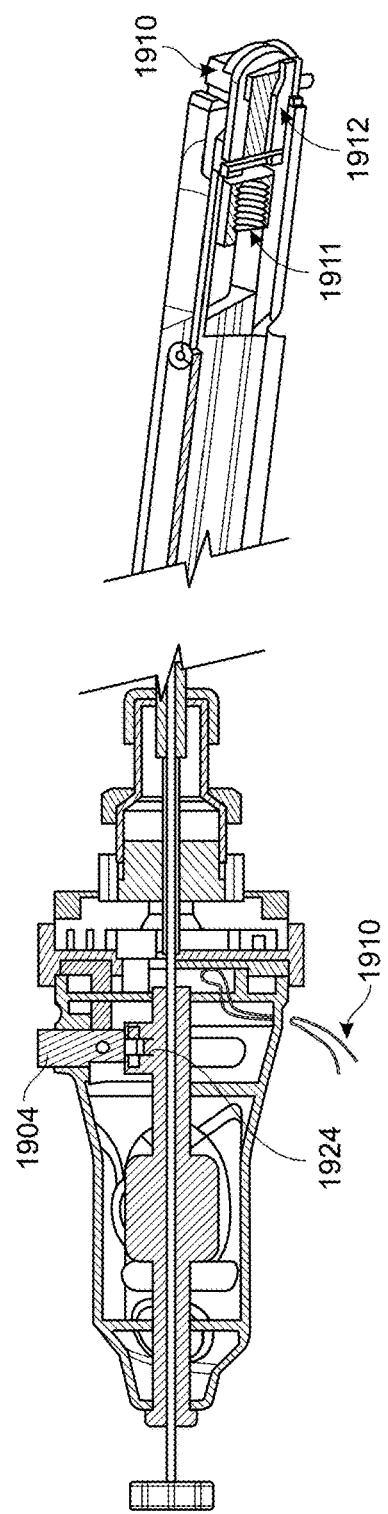
Figure 19I:
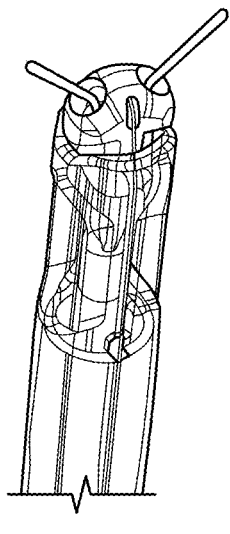
Figure 19K:
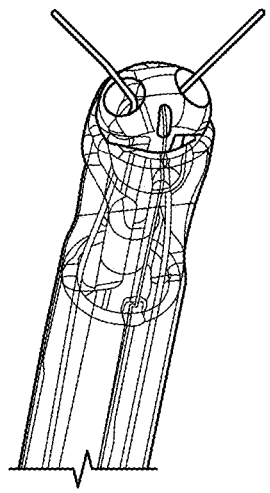
Figure 19H:
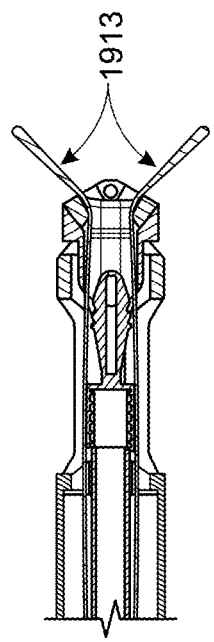
Figure 19J:
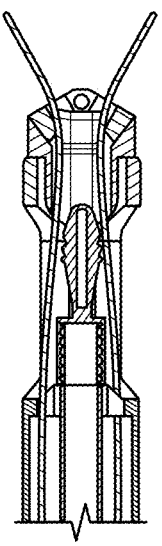
Figure 19L:
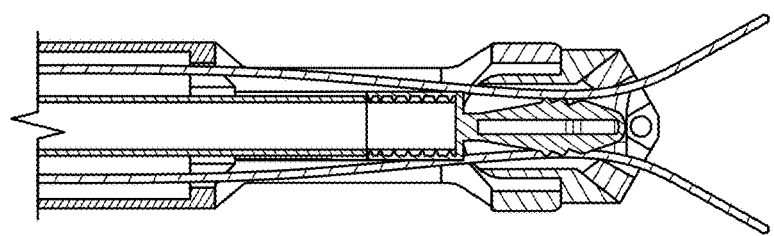
Figure 19M:
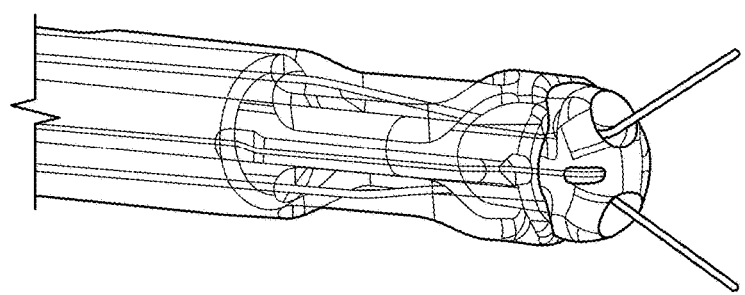
Figure 19N:
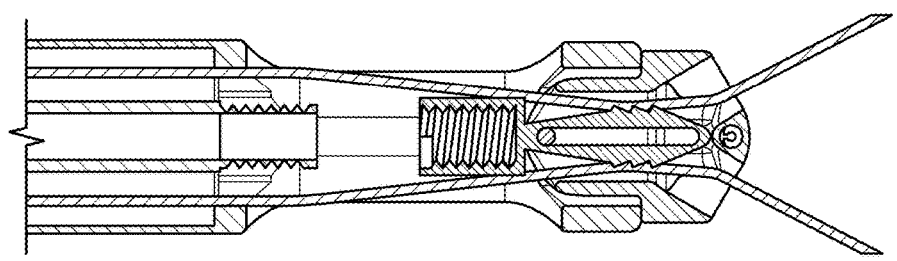
Figure 19O:
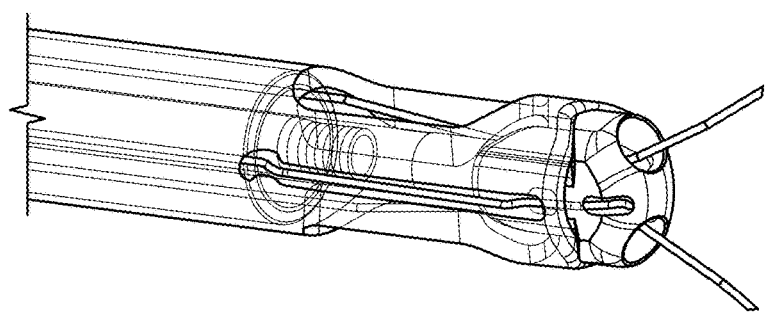
Figure 19P:
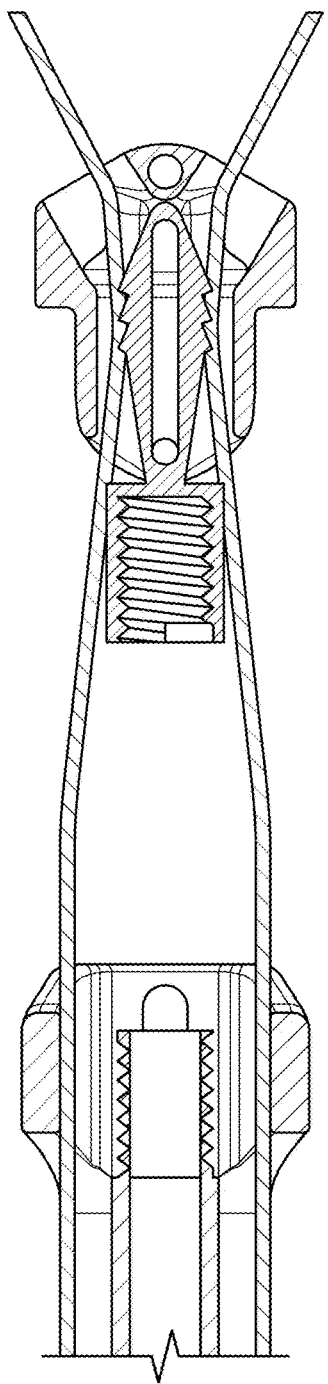
Figure 19Q:
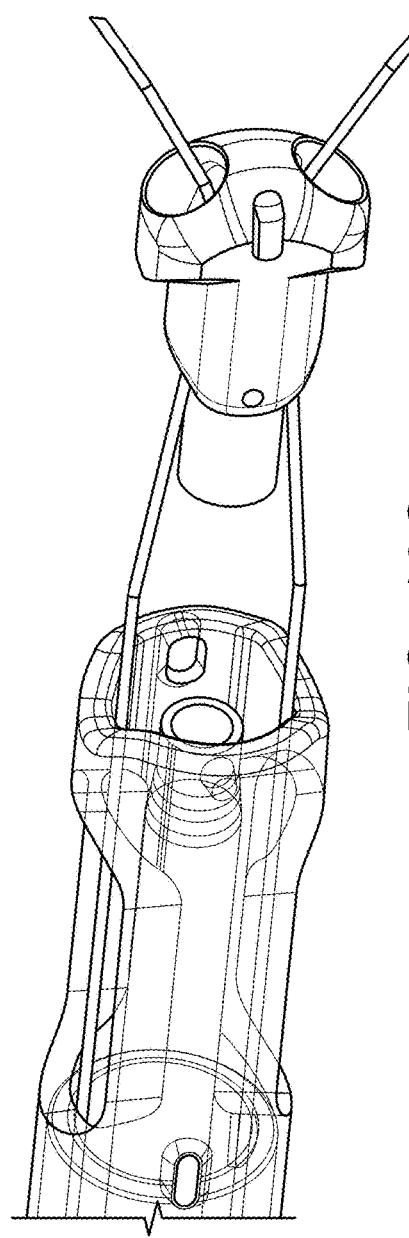
Figure 19R:
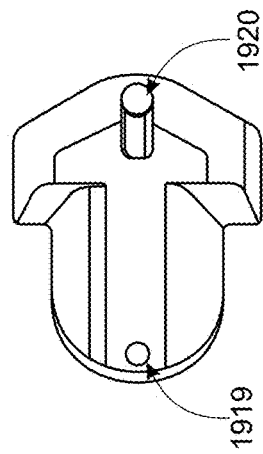
Figure 19S:
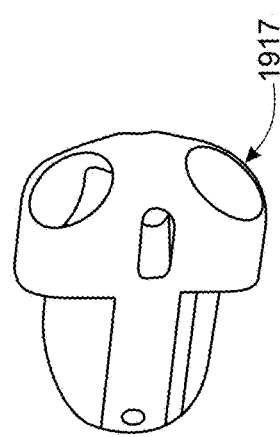
Figure 19T:
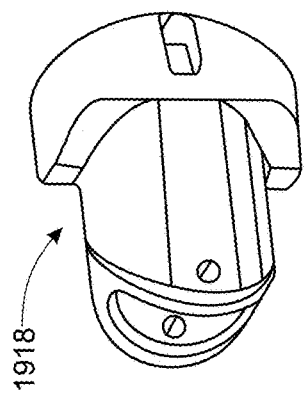
Figure 19U:
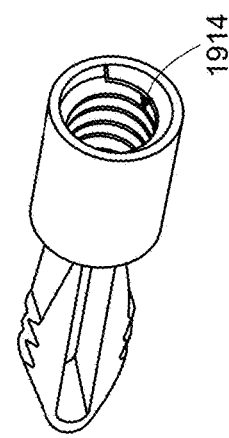
Figure 19V:
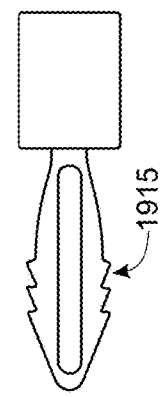
Figure 19W:
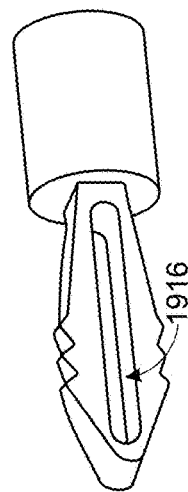
Figure 19X:
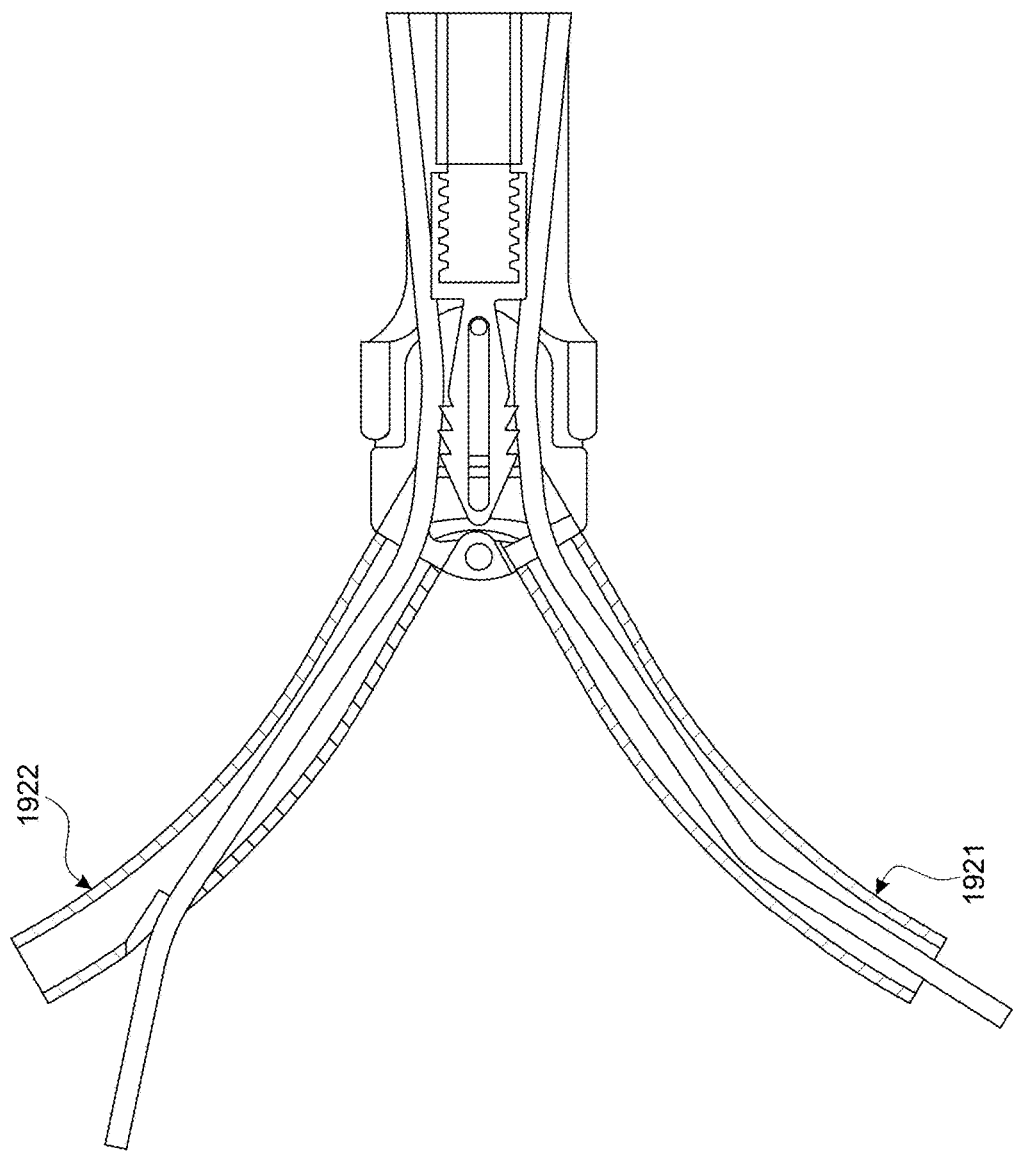

FIGS. 19C-19X illustrate aspects of a further embodiment of a lock delivery system and associated lock in accordance with the disclosure. By way of introduction, FIG. 19C depicts the overall lock system, FIG. 19D depicts the lock in an open position, and FIG. 19E depicts the lock in a closed position. As depicted, this embodiment of a lock delivery system bears certain similarities to that of FIGS. 19A-19B, but adds additional features. With reference to the Figures, the system includes a proximal housing 1905 connected to a hemostatic delivery device hub with flush port 1906 connected to a distal outer tubular member 1907 that is connected at its distal end to a housing 1908 for the lock body. Housing 1908 is configured and adapted to maintain the lock body 1912 in rotational registration with respect to the lock delivery system, such that turning the delivery system will cause the lock body 1912 to turn with it.

Lock body 1912 has a proximal body and a distal body that are coupled via a limiter pin (visible in cross section of FIG. 19G) received in opening 1919 in distal body. The proximal portion of lock body 1912 is in turn threadably attached to a distal end of a central articulation, or wedge shaft, 1909, that traverses the length of the delivery system to a proximal control handle or knob. Shaft 1909 is configured to wedge the two portions of the lock together so as to clamp down on both ends of the outer sheath 1901/50.

In accordance with one aspect, the lock delivery system includes a lock retaining tether 1910 that is configured and adapted to be routed through the delivery system and around the distal end of the distal portion of the lock element. As illustrated, tether 1910 is actually directed through an orifice defined in the distal portion of the lock element 1912. The lock retaining tether is directed from the proximal end through the distal end of the lock body, as illustrated. The purpose of the lock retaining tether 1910 is to provide adjustable tension to the distal portion of the lock body 1912 through housing 1908 and prevent it from movement, and thus to resist forces imparted by shaft 1909 to permit locking of the main sheath 1901/50 more efficiently. At the end of a procedure wherein the lock is placed, to fully release the lock, this tether 1910, which is simply looped through the distal body of the lock 1912 is removed. Prior to its removal, the tether 1910 permits a physician to fully retrieve the lock body after deployment, since the tether 1910 can act as a guiding rail for the delivery system and guide it toward and over the lock body 1912.

Figure 19Z:
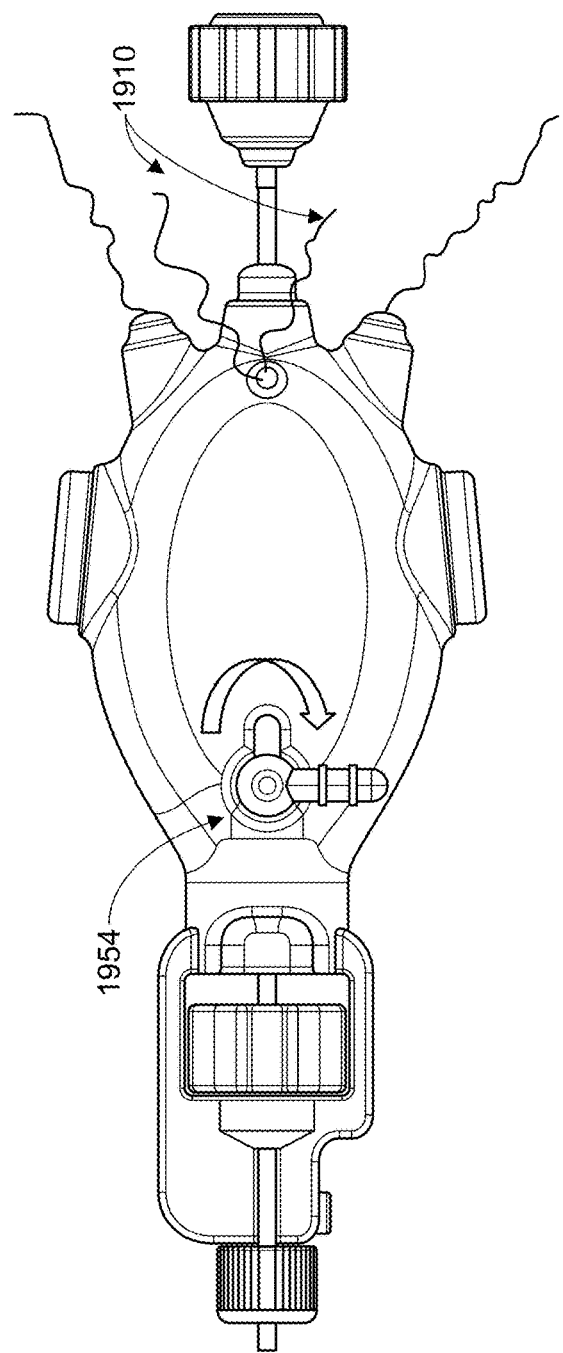
Figure 19A:
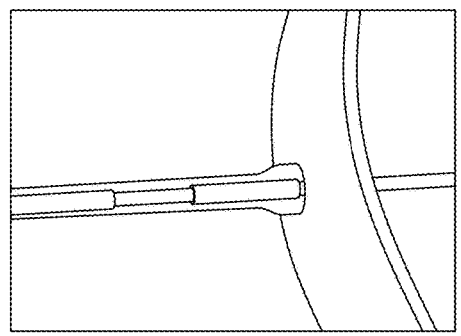
Figure 19A:
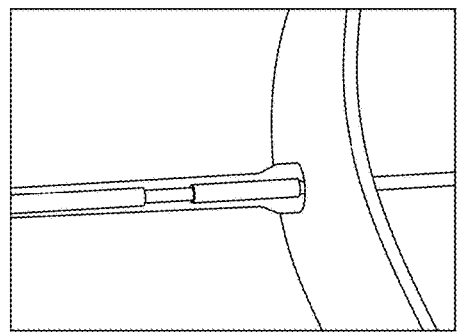
Figure 19A:
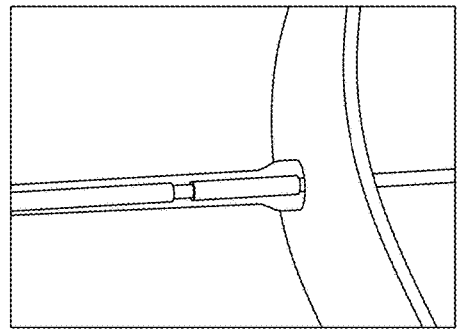
Figure 19A:
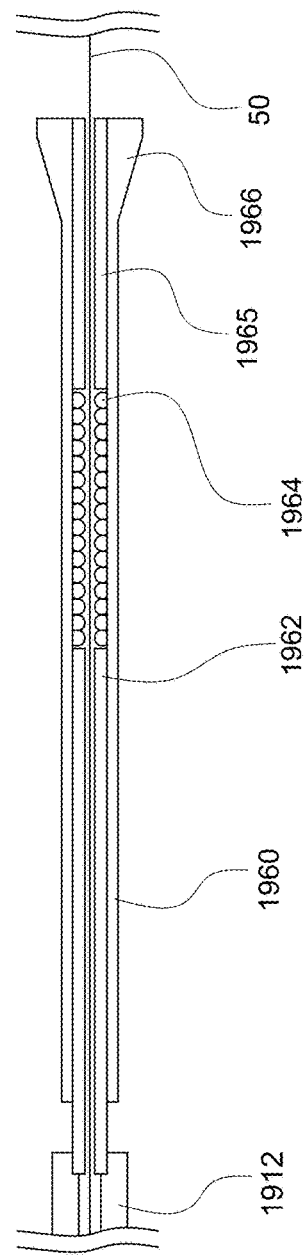
Figure 19A:
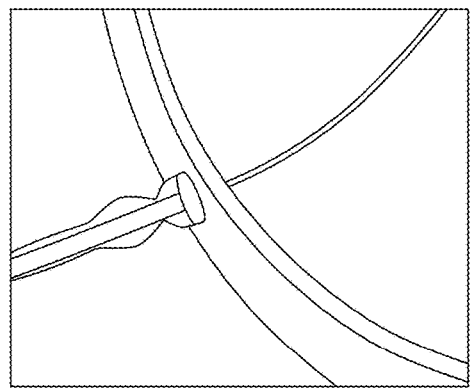
Figure 19A:
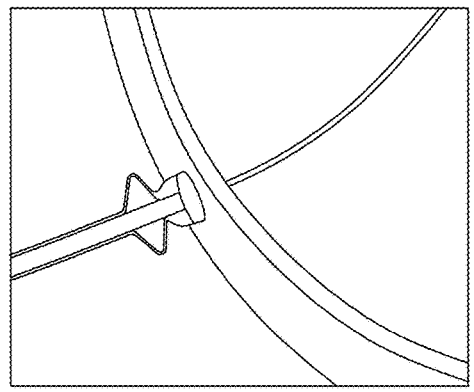
Figure 19A:
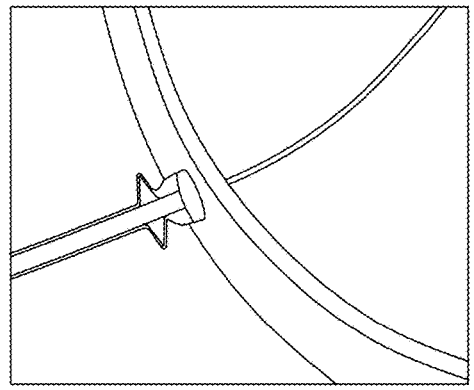
Figure 19A:
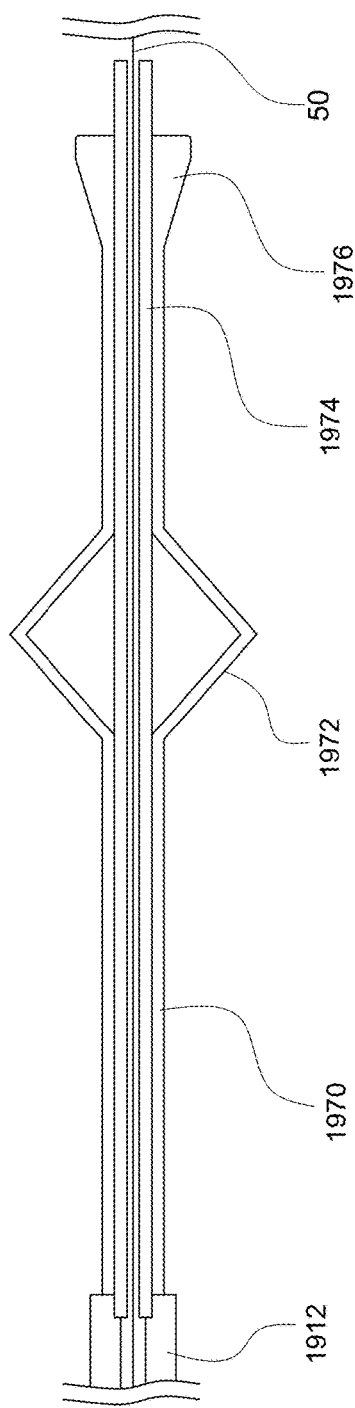

If desired, a release control, or button, 1904 can be provided for the lock retaining tether. As depicted, lock retaining tether 1904 is configured and adapted to maintain the lock retaining tether 1910 under tension until it is pressed down to allow release of tension on the retaining tether, and to permit removal of the tether 1910 at the end of the procedure once the physician is certain that the lock 1912 has been positioned correctly. FIGS. 19Y-19Z illustrate a side sectional view and a top view, respectively, of a further embodiment of a housing for a lock delivery catheter that includes a rotatable release knob or lever 1954 in lieu of a control button 1904. When in a locked position, the tether 1910 is held fast and locked in place via frictional forces. When the knob or lever 1954 is rotated by a predetermined amount about its rotation axis within the housing, such as 90 degrees, the tether 1910 is movable, and tension can be applied to the tether, if desired, or the tether 1910 can be withdrawn from the device.

The illustrated embodiment of the lock delivery system further includes one or more additional spring loaded push buttons 1902, or tension controls, for controlling grasping of either end of the outer sheath (e.g., 50) of the implant. In a default position where the button is not depressed, the tether passing through a capture mechanism associated with the push button will grip the implant tether 1901 (e.g., sheath 50 described elsewhere herein) and maintain it under tension. When each push button (individually and/or both) is pressed down, it will allow for release of one or both tethers associated with the implant. It will be appreciated that both ends of the tether can be routed through the same control button for purposes of simplicity.

As further illustrated, the proximally facing portion of the distal body of lock 1912 is generally convex in shape, and the distal portion of housing 1908 is concave, and is shaped in a complementary manner to match to facilitate recapture of the lock 1912 after it is released. That coupling can also be provided with an alignment boss to maintain rotational registration between lock body 1912 and housing 1908.

FIG. 19F presents a first section view through the handle, and FIG. 19G presents a second section view through the handle that is rotated 90 degrees about a longitudinal axis of the device from the section view of 19F. Implant tether 1901 is depicted as being under tension when spring loaded push button(s) 1902 is in a normal, or released, position. Compression springs 1923, 1924 can be provided for urging tether 1901 through a tortuous path to hold it in place.

With reference to FIGS. 19H and 19I, in a first step of employing the lock delivery catheter, the ends of the outer sheath (1901/50) of the implant must be snared by capturing them in loops 1913, which are in turn pulled proximally through the lock delivery system past the pressure buttons so that tension can be applied to the sheath 1901/50. This is done while the lock portions are separated, with the pressure button(s) 1902 depressed down so the path for snare to travel is clear.

With reference to FIGS. 19J and 19K, after snaring the implant tethers 1901, the lock is delivered to the desired location by sliding it over the tethers 1901 while the lock body 1912 is open and the push button(s) 1902 are still pressed down so the tethers 1901 are not engaged.

With reference to FIGS. 19L and 19M, after reaching the desired location, tension is be applied to the implant tether 1901 and the button(s) 1902 are released to maintain tension on the tether 1901. At this point, the lock 1912 is actuated by moving forward the central wedging shaft 1909 distally to engage the inner, proximal body (wedge portion) of the lock 1912 against the distal portion of the lock body, wedging the tether 1901 between the components of the lock, preventing it from moving with respect to the tether 1901.

With reference to FIGS. 19N and 19O, after activating the lock to engage the tether 1901, the next step is to unscrew or otherwise detach the proximal body of the lock from the set screw on the wedge shaft 1909 and withdrawing the wedge shaft.

With reference to FIGS. 19P and 19Q, after the preceding step, tension can be released on the lock retaining tether 1910, for example, by pressing down the release button 1904, thereby permitting the delivery system to be pulled proximally along the lock retaining tether 1910, releasing the lock, but for its connection to the tether 1910. If the physician is confident that the lock 1912 has been placed correctly, the tether 1910 can then be removed by pulling on one end of it and removing it from the lock 1912, and the patient.

FIGS. 19R to 19W particularly illustrate the proximal and distal bodies making up the lock 1912. Additional selfalignment is facilitated by providing a boss on either side of the distal lock that have convex surfaces 1918 that extend toward housing 1908 and are received by matching distally facing notches in housing 1908. This both helps facilitate recapture of the lock, and helps to apply torque to the lock when it is held fast against the housing 1908 by tether 1910. Also visible is an orifice 1920 for routing tether 1910 therethrough. The presence of tether 1910 permits the lock 1912 to be held fast against the distal face of housing 1908, and to facilitate recapture of the lock 1912 after it is positioned within a patient, as long as the tether 1910 is in place. As illustrated, the proximal body of the lock is provided with a female threaded proximal end 1914 to permit it to releasably engage the threads of wedge shaft 1909 open and close the lock. The threaded connection also makes it possible to recapture the lock with a snare after releasing it. Teeth 1915 are provided on the lock to hold the lock closed against tether 1901 when the lock 1912 is engaged with the tether. When the lock is open, the tether 1901 can easily pass through the lock. As with the previous embodiment of the lock set forth above, this embodiment also includes a pin slot 1916 that is configured and adapted to the proximal body 1911 of the lock to slide back and forth over the limiter pin to open and close the lock.

As illustrated in FIG. 19S, two orifices 1917 are provided, as with the preceding lock embodiment, to permit tethers to pass therethrough, as well as to accommodate a strain relief/protection leg, as depicted in FIG. 19X. The orifices 1917 are angularly disposed outwardly with respect to one another to provide for ease of use. As illustrated in FIG. 19R, a hole 1919 is provided to insert the limiter pin therethrough, which also passes through pin slot 1916 to hold the proximal and distal lock bodies together.

FIG. 19X illustrates a wedge lock system including two flexible protection legs 1921, 1922 wherein one of the legs 1922 includes an orifice through a wall thereof for routing the tether. One or both legs can be so equipped with an opening. This can be done to shorten the path along which the tether 1901 must traverse along the protection leg, and to provide a smoother transition in pressure to the underlying tissue. One or both protection legs 1921, 1922 can be so configured, or one or both can be equipped with stoppers at the end of the legs.

As set forth in FIGS. 19AA-19AD, a further embodiment of a limb with an adjustable length is presented. FIG. 19AD presents a cross sectional view of an implant (e.g., tether 50) passing through a limb of adjustable length that is attached at a proximal end to lock body 1912. The limb includes an outer tubular member 1960 that can include a bell-shaped atraumatic distal tip 1966, preferably integral thereto, for abutting a septal wall. Outer tubular member 1960 is also preferably attached to a distal section 1965 of an inner tubular member that extends from the distal tip 1966 along a proximal direction to a location where a compression spring 1964 is disposed underneath the outer tubular member 1960. The distal end of spring abuts the proximal end of the distal section 1965. A proximal inner tubular member 1962 is slidably disposed within a proximal section of tubular member 1960. A proximal end of proximal inner tubular member 1962 is attached to the lock body 1912, and a distal end of the proximal inner tubular member 1962 abuts a proximal end of the spring 1964. Thus, spring 1964 is contained in a compartment defined by an inner cylindrical surface of outer tubular member 1960 the proximal end of tubular member 1965 and the distal end of tubular member 1962. Spring 1964 defines and surrounds an interior lumen along its length that permits the passage of sheath 50.

In operation, when the distal tip 1966 abuts the septal wall, the overall length of the limb can be reduced by pushing distally on the lock body, which in turn pushes against the proximal inner tubular member 1962 that in turn slides distally within (and with respect to) the outer tubular member 1960, compressing the spring 1964. The proximal portion of inner tubular member 1962 that is not surrounded by outer tubular member 1960 defines the amount that the spring can compress, which can be arranged as desired. The spring can be configured to compress completely, or only partially. It will be appreciated that FIG. 19AD is a representative cross section, and is not intended to be to dimensional scale. To further illustrate this embodiment, FIG. 19AA illustrates the limb in a lengthened state wherein the spring 1964 is not compressed. FIG. 19AB shows the spring partially compressed, and FIG. 19AC shows the spring fully compressed.

As set forth in FIGS. 19AE-19AH, a further embodiment of a limb with an adjustable length is presented. FIG. 19AH presents a cross sectional view (not to dimensional scale) of an implant (e.g., tether 50) passing through a limb of adjustable length that is attached at a proximal end to lock body 1912. The limb includes an outer tubular member 1970 that can include a bell-shaped atraumatic distal tip 1976, preferably integral thereto, for abutting a septal wall. Outer tubular member 1970 includes a distal section and a proximal section separated by a compression section 1972. Compression section 1972 is defined by a plurality of parallel cuts passing from an outer surface of the outer tubular member to an inner surface of the outer tubular member. The cuts are arranged parallel to a central longitudinal axis of the limb, and (preferably uniformly) distributed circumferentially around the circumference of the outer tubular member 1970. The cuts are preferably of uniform length and lengthwise alignment (but this may be varied, as desired). Any suitable number of such cuts may be made around the tubular member 1970. The proximal section of the outer tubular member may be directly attached to lock 1912. As illustrated, the proximal section of tubular member 1970 is attached to a proximal section of an inner tubular member 1974, wherein the proximal end of tubular member 1974 is received within and attached to lock 1912. Tubular member 1974 is not attached to the section of tubular member 1970 that is located distally of the compression section 1972 to permit relative sliding contact between the tubular members 1970, 1974 in that section. In operation, and with reference to FIGS. 19AE-19AG, FIG. 19AE illustrates the limb at full length, wherein the legs defined between the cuts in the compression section 1972 are beginning to separate from each other and bow radially outwardly as the outer tubular member 1970 shortens. FIG. 19AF shows the legs bowed further outwardly as tubular member 1970 continues to shorten, and FIG. 19AG shows member 1970 at its shortest length, wherein the resilient legs of the "spring" or compression section 1972 are fully compressed, forming a petal arrangement around the circumference of the limb.

FIGS. 20A-20C illustrate deployment of the illustrated lock on the exemplary cerclage device in an animal. FIG. 20A illustrates an image of the lock delivery catheter 1410 delivered to a location where tension may be imposed on the sutures (e.g., 50) by pulling them proximally through the lock delivery system and locking the lock to maintain the tension. In FIG. 20B, the outer tubular member 1420 is released from the outer lock portion 1455 and withdrawn. In FIG. 20C, the inner tubular member 1430 is attached from the inner portion 1452 of the lock 1450, leaving the deployed lock 1450 in place, tensioning the cerclage implant.

Figure 21A:
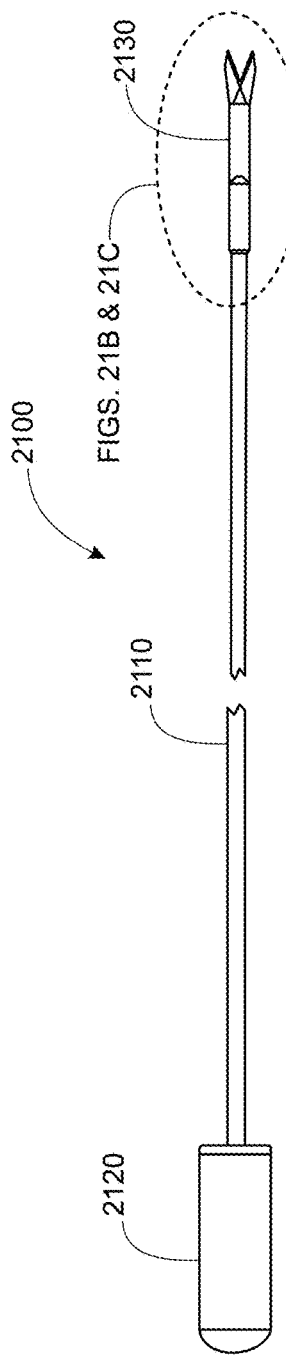
FIGS. 21A-21F illustrate portions of a cutting instrument in accordance with the disclosure.
Figure 21B:
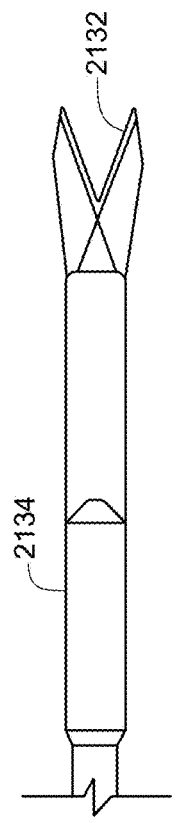
Figure 21C:
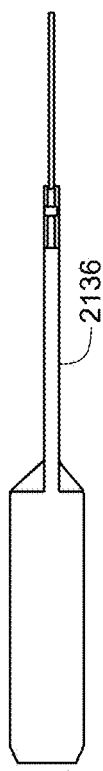
Figure 21D:
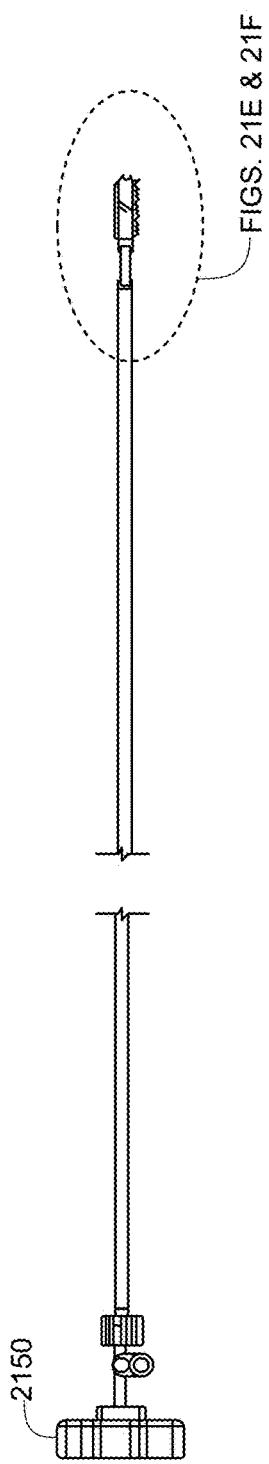
Figure 21E:
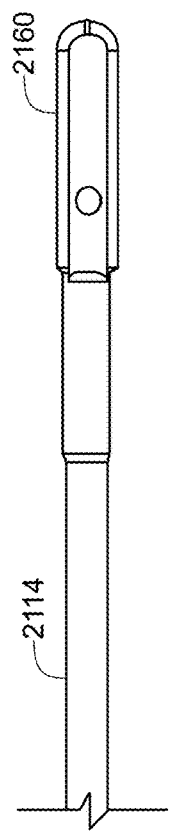
Figure 21F:
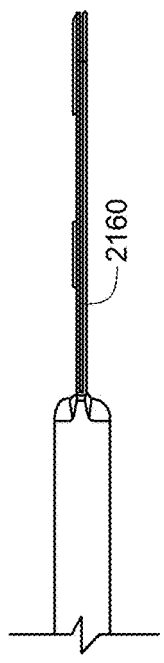

FIGS. 21A-21F illustrate portions of a cutting instrument 2100 in accordance with the disclosure for cutting the tethers/sheath material after the lock has been deployed. The cutting instrument 2100 includes an inner assembly with a blade that is slidably disposed within an outer assembly having a suture guide configured to hold suture/sheath material in position to facilitate cutting thereof while inside the heart, or other intracorporeal location. FIG. 21A illustrates the inner assembly of the cutting instrument, which includes an elongate core shaft member 2110 attached at a proximal end to a push hub 2120 and to a cutting blade holder 2130 at a distal end. FIGS. 21B-21C illustrate the cutting blade holder 2130, wherein a proximal, cylindrical portion 2134 of the cutting blade holder attaches to core shaft 2110 distal end, which in turn tapers down to a generally planar distal segment having a lateral slot 2138 formed in its distal end for receiving a "V"-shaped cutting blade 2132. Cutting blade 2132 includes two blades in a V configuration, wherein the blades define the inner portion of the V, and the apex of the inner portion of the V is distally directed. The V shape of the blade directs suture material toward the apex of the V, and the blades act to cut the suture material as they pass over it. FIG. 21D illustrates the outer assembly of the cutting instrument 2100, which includes an elongate hollow tubular member 2140 configured to slidably receive member 2110 therethrough connected at a proximal end to a glanded, hemostatic hub 2150 with a flush port for flushing the annular space between tubular members 2110, 2140. Tubular member 2140 includes a cutting blade outer housing 2160 mounted at a distal end thereof that is further illustrated in top and side views in FIGS. 21E-F. Outer housing 2160 includes a proximal tubular section that attaches to a distal end of tubular member 2140 that necks down to a flattened distal tubular section.

Figure 22A:
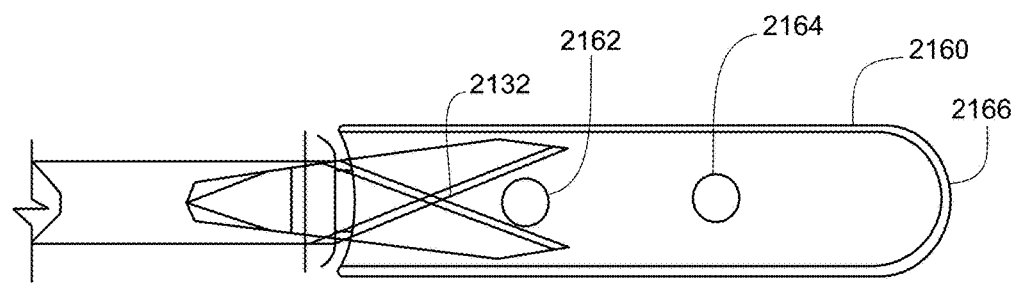
Figure 22B:
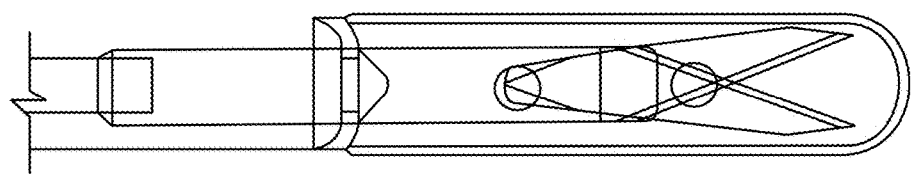
Figure 22C:
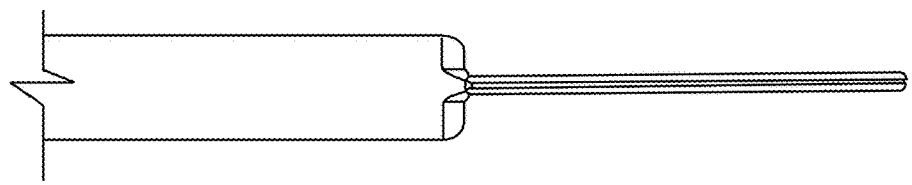
Figure 22D:
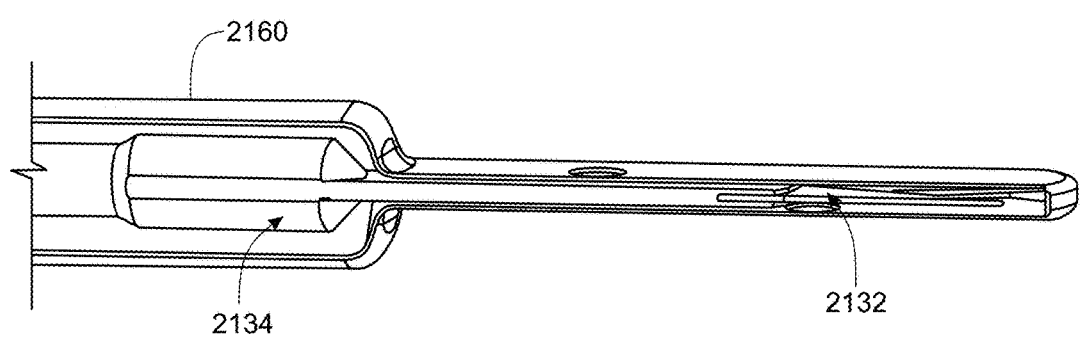

As illustrated in FIG. 22A, outer housing 2160 includes a rounded, atraumatic end 2166 and defines two axially spaced apart holes therethrough, wherein the distal hole 2164 accepts a sheath or suture (e.g., 50) therein as an entrance point or entrance hole, and the proximal hole 2162 provides an exit for the suture/sheath. In use, the cutting instrument 2100 is threaded over each tether of the implant in this manner through the holes 2162, 2164 after the lock delivery catheter is removed, and the sheath material (e.g., 50) is external to the patient or otherwise easily accessible. The cutting instrument is then delivered into the heart to a location near the lock 1450 that is already in place. The inner assembly of the cutting mechanism is then advanced distally with respect to the outer assembly of the cutting mechanism until the blade 2132 has advanced past both holes 2162, 2164, cutting the tether (e.g., 50), as illustrated in FIG. 22B. As illustrated in FIG. 22C, the flattened distal profile of the cutting instrument 2100 both reduces the profile of the instrument, as well as provide for superior alignment and smooth cutting operation. FIG. 22D provides a cutaway view of the distal end of the cutting instrument showing the relative placement of the inner and outer assemblies after the inner assembly has been fully extended distally to accomplish the cutting operation. FIGS. 22E-22F illustrate the distal to proximal tether threading direction. Holes 2162, 2164 can be pre-threaded with a snare suture with a loop in a manner similar to the lock delivery catheter 1400, if desired. In any event, the suture to be cut is threaded as disclosed, entering the distal hole 2164 and exiting via the proximal hole 2162. This provides an orientation of the suture with respect to the cutting instrument that facilitates sliding the cutting instrument 2100 along the tether to a region in the heart near the deployed lock 1450 in a manner similar to a "rapid exchange" (RX) type of catheter. FIG. 22G illustrates placement of the cutting instrument 2100 in a procedure, wherein both the distal and proximal tethers of the implant are routed through holes 2162, 2164 simultaneously.

Figure 22H:
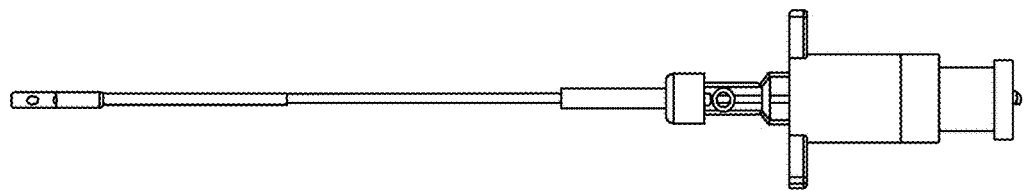
FIGS. 22H-22L illustrate a further embodiment of a cutting instrument in accordance with the present disclosure.
Figure 22I:
Figure 22J:
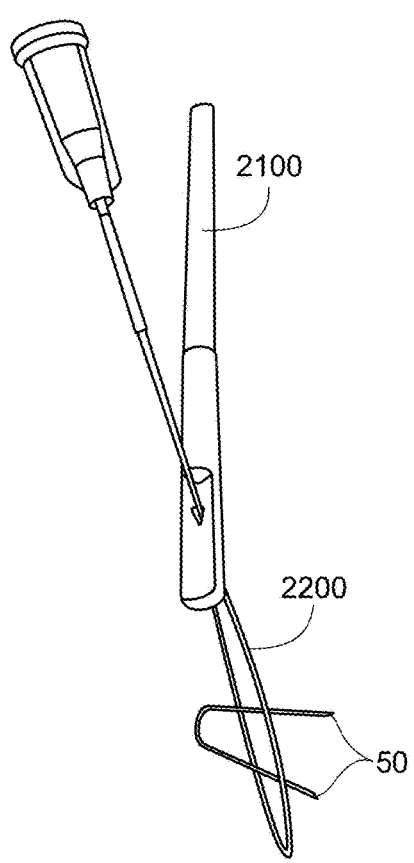
Figure 22K:
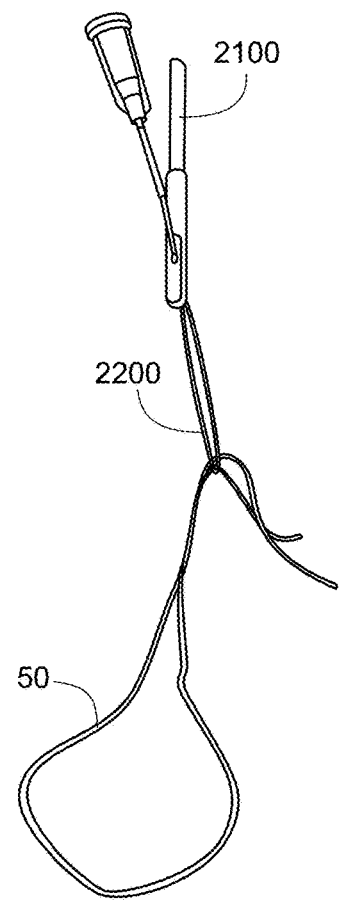
Figure 22L:
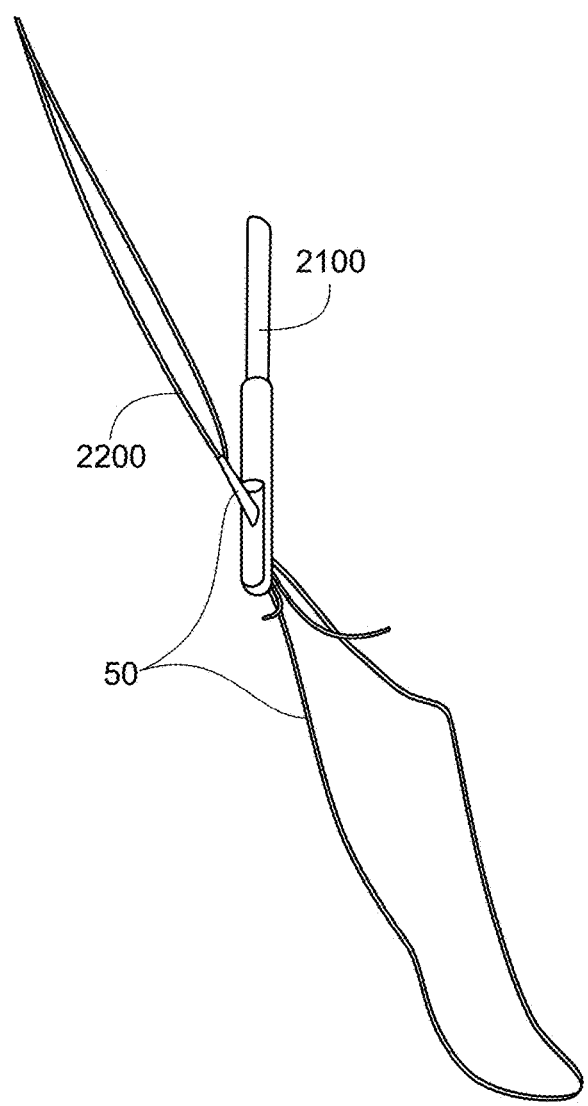

FIGS. 22H-22L illustrate a further embodiment of a cutting catheter 2100 in combination with a loading snare 2200. As illustrated in FIG. 22H, the catheter 2100 includes a distal end and internal mechanisms as set forth above, and including a proximal handle having a spring loaded push button trigger, wherein the button is biased in a proximal direction by the spring (not shown). The button is connected to the inner movable shaft of the cutting catheter at the proximal end of the shaft, which is in turn connected at its distal end to the cutting blade. When the button is depressed by a user, the blade advances distally past openings 2162, 2164 to cut any tether spanning the openings through the cutting catheter 2100. The snare is utilized by initially passing the elongate loop portion of the snare diagonally through the distal portion of catheter 2100 by way of openings 2162, 2164. As illustrated in FIGS. 22J-22L, after the loop of snare 2200 is positioned through catheter 2100, ends of loop tether/sheath 50 are passed through the snare 2200, and the snare is withdrawn through catheter 2100, carrying tethers 50 therewith, effectuating threading of the cutting catheter with the loop tether/sheath 50.

It will be appreciated that other structures can be cut or severed using the cutting catheters of FIGS. 22A-22I. For example, in a further implementation, the cutting catheter can be used to cut a cardiac lead previously attached to a pacemaker. Removal of cardiac leads is typically dangerous, but the presently disclosed embodiment can be threaded down the cardiac lead, for example, into the left ventricle or other cardiac location. The lead can then be severed near or at the anchoring point, leaving the anchor in place, but removing the wire.

Figure 23C:
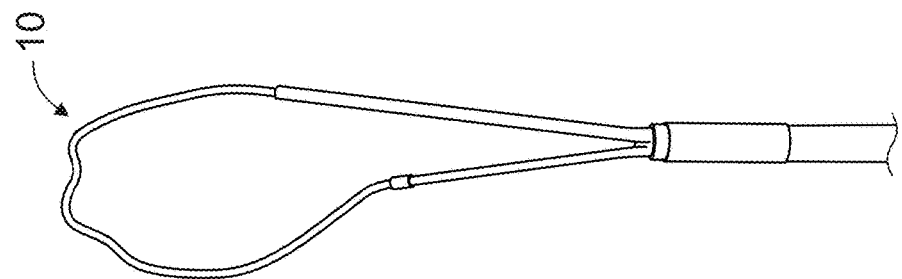
FIGS. 23A-23C illustrate various views of an illustrative cerclage system in accordance with the disclosure attached to an exemplary lock delivery catheter.
Figure 23B:
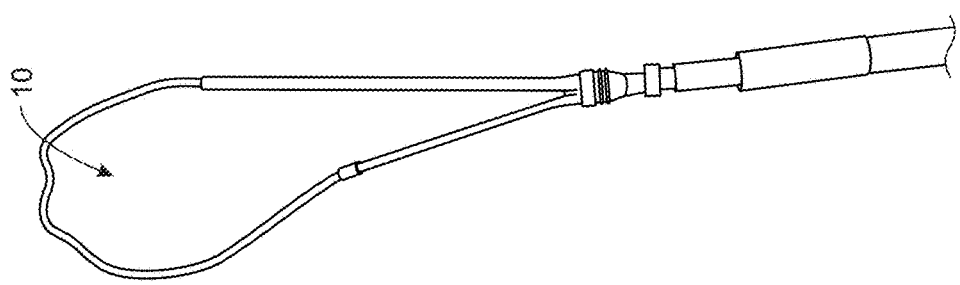
Figure 23A:
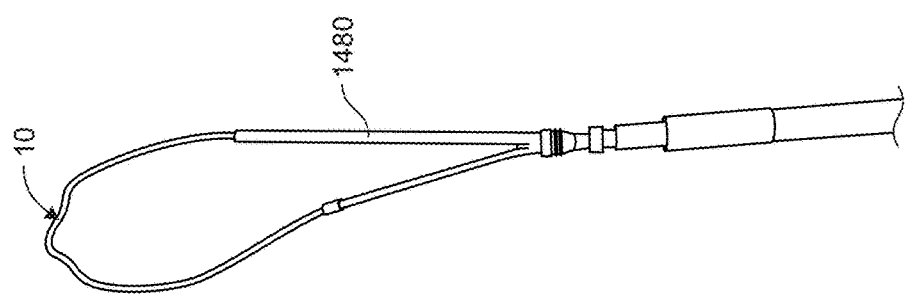
Figure 24C:
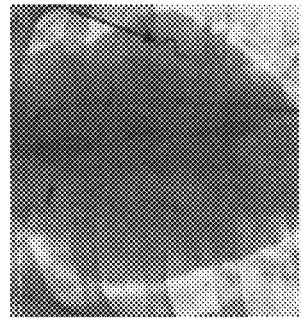
FIGS. 24A-24E illustrate an exemplary procedure for performing an annuloplasty procedure in accordance with the present disclosure.
Figure 24B:
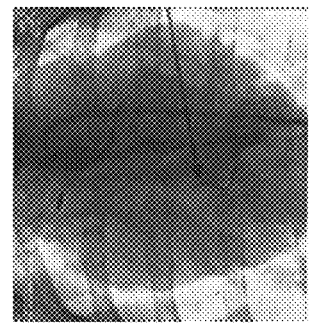
Figure 24A:
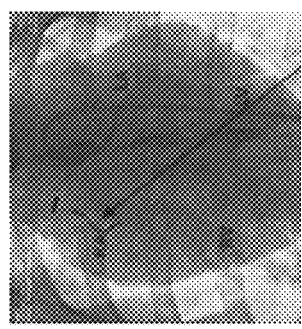
Figure 24E:
Figure 24D:
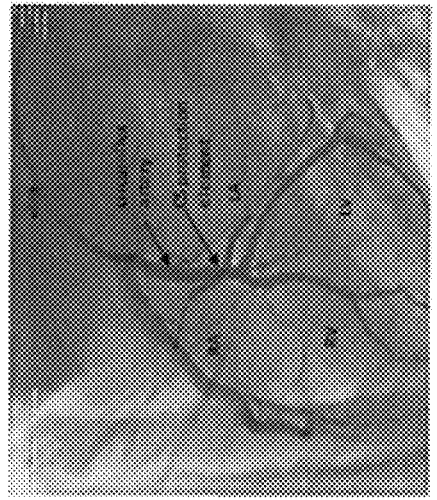

FIGS. 23A-23C illustrate various views of an illustrative cerclage system in accordance with the disclosure attached to an exemplary lock delivery catheter, showing relative placement of the various components including the implant and the strain relief legs of the lock delivery catheter. FIGS. 24A-24E illustrate an exemplary procedure for performing an annuloplasty procedure in accordance with the present disclosure. The figures clearly show advancement of the protection element (e.g., 20) within the implant (e.g., 10) advanced and delivered to a location spanning the LCx artery.

Figure 25A:
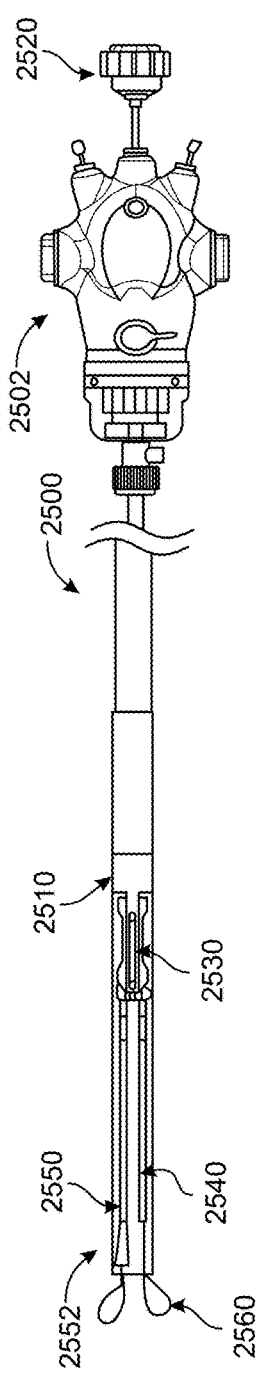
FIGS. 25A-25E illustrate aspects of a further embodiment of an implant delivery system in accordance with the present disclosure.
Figure 25B:
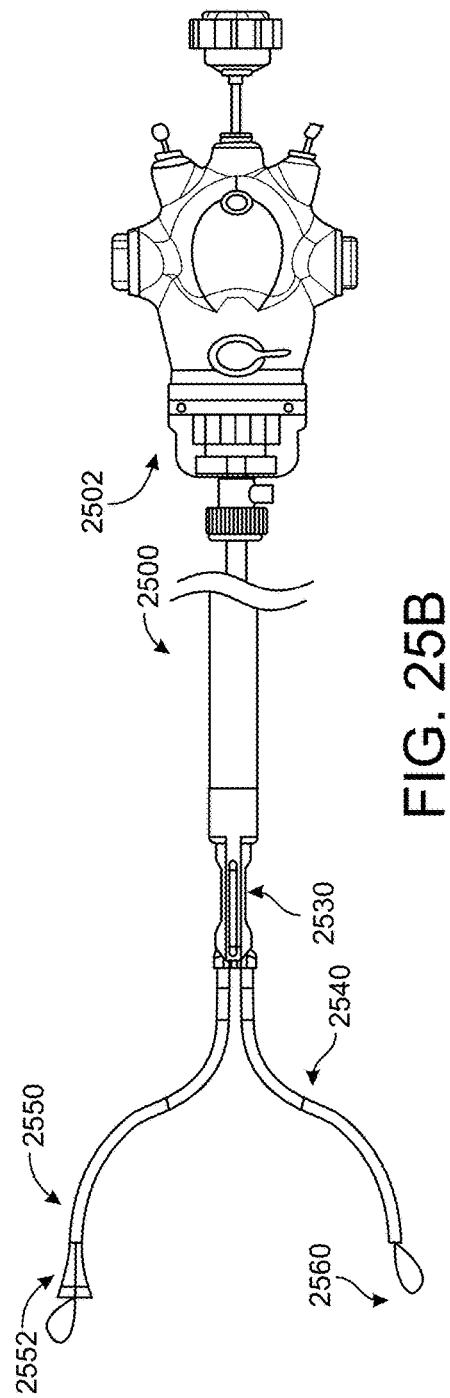
Figure 25C:
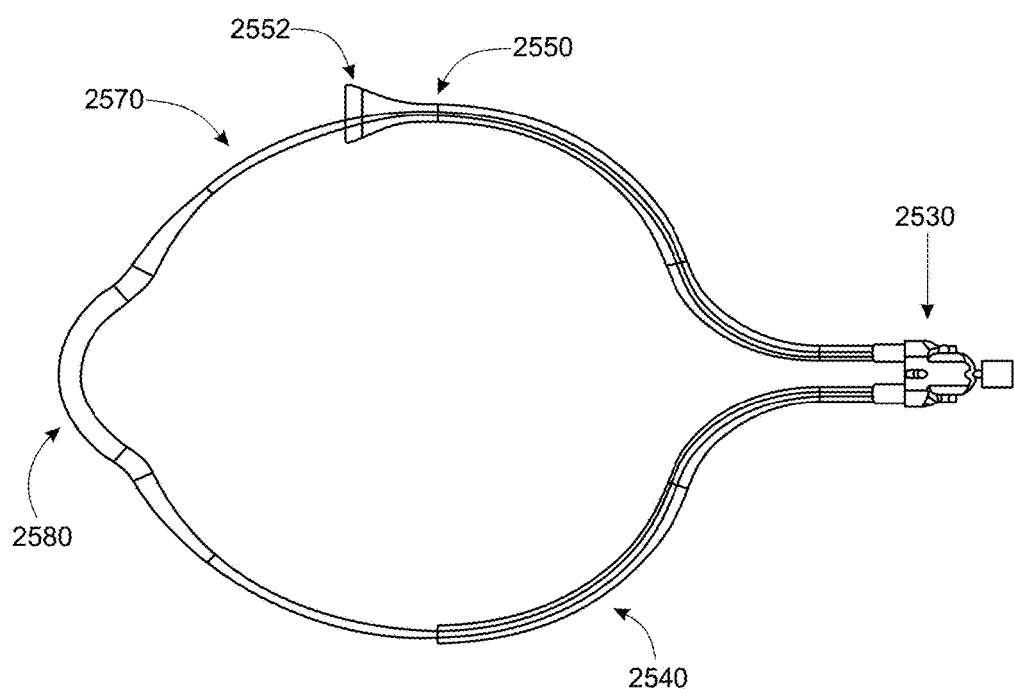
Figure 25E:
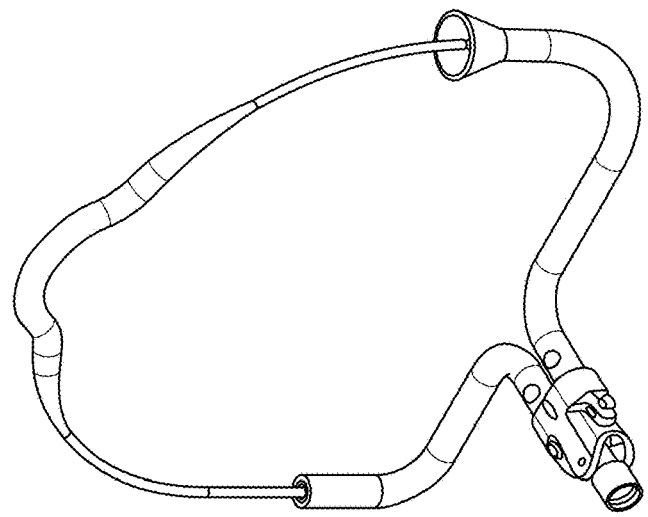
Figure 25D:
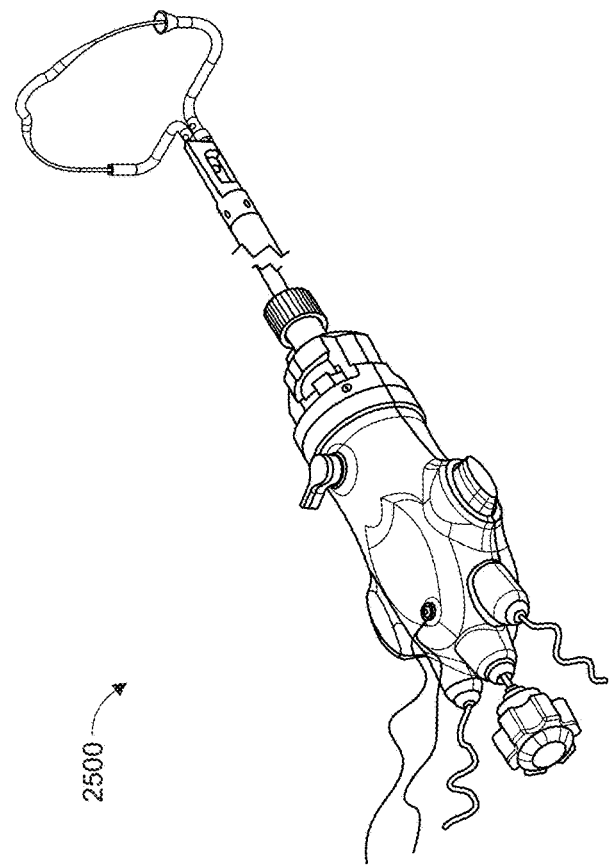

FIGS. 25A-25E illustrate a further embodiment of a lock delivery catheter 2500 including a handle 2502 similar to previous embodiments. Catheter 2500 includes a handle 2502 that has the same functionality as previous embodiments with a tensioning tether control as described above with reference to FIGS. 19Y-19Z. Catheter 2500 includes a lock release knob for advancing the lock mechanism proximally or distally with respect to the handle 2502, as well as for releasably engaging the lock body (e.g., via threaded connection) as set forth above. Catheter 2500 further includes a removable sheath 2510 that surrounds the lock body 2530, the coronary sinus limb 2540, the tricuspid valve limb 2550 that may include a bumper 2552 (for spreading out axial force applied to the septal wall), and may provide a conduit for guiding placement of the tether loading snares. The catheter including the sheath 2510 can be introduced into the patient's vasculature over the outer sheath (e.g., 50)

of the implant after the delivery tubes (or core wires, depending on the embodiment) are removed. The sheath can be withdrawn proximally, for example, via a pull wire (not shown) routed through handle 2502 or peeled off, ruptured, or the like at a suitable time, such as when the distal end of the sheath is near the patient's heart. The limbs are then exposed, which can be directed into the vasculature of the heart, and placed where desired. The sheath (e.g., 50) can then be locked inside of the lock body 2530, and the excess sheath extending proximally from the lock body 2530 can be severed using embodiments of the cutting catheter disclosed herein. FIG. 25C shows a schematic view of the installed implant and lock body with limbs, which may include the coronary protection element 2580 (if desired) surrounded by the sheath 2570, which may be radiopaque as discussed above. Also illustrated are the tricuspid valve limb 2550 with the bumper 2552, as well as the coronary sinus limb 2540. FIG. 25D presents an isometric view of the lock delivery system 2500 prior to deployment (release) of the lock body, whereas FIG. 25E illustrates a perspective view of the lock and implant after deployment. As illustrated, the limbs are presented as not being planar, but instead having a three dimensional curvature wherein the limbs curve out of plane toward the lock. As will be appreciated, the proximal ends of the limbs are preferably attached to the lock body.

The devices and methods disclosed herein can be used for other procedures in an as-is condition, or can be modified as needed to suit the particular procedure. In view of the many possible embodiments to which the principles of this disclosure may be applied, it should be recognized that the illustrated embodiments are only preferred examples of the disclosure and should not be taken as limiting the scope of the disclosure. Each and every patent and patent application referenced herein is expressly incorporated by reference herein in its entirety for any purpose whatsoever.

The invention claimed is:

1. An implant, comprising:
   a) a bridge having a proximal end, a distal end, and an arched portion defined between the proximal end and the distal end of the bridge;
   b) an elongate inner tether coupled to the bridge;
   c) an outer sheath material having a first end and a second end circumferentially surrounding the bridge and elongate inner tether; and
   d) an implant lock, wherein the first and second ends of the outer sheath material are directed through the implant lock.

2. The implant of claim 1, wherein at least one of the elongate inner tether and the outer sheath includes radiopaque material disposed along its length.

3. The implant of claim 2, wherein the elongate inner tether includes a radiopaque wire disposed therein, the radiopaque wire being disposed within a length of heat shrunk polymeric tube that resides within a hollow core of the elongate inner tether.

4. The implant of claim 1, further comprising an outer polymeric tube within the outer sheath material that is shrunk around the bridge and the inner elongate tether, the polymeric tube extending axially beyond the proximal end and the distal end of the bridge.

5. The implant of claim 4, wherein the elongate inner tether passes over a top face of the arched portion of the bridge within the outer polymeric tube and outer sheath material.

6. The implant of claim 4, wherein the outer sheath material is a hollow woven tubular material that extends proximally and distally beyond the outer polymeric tube, and further wherein portions of the outer polymeric tube extending beyond the proximal end and the distal end of the bridge form a strain relief to provide a transition in stiffness of the implant from the bridge to the outer sheath material.

7. The implant of claim 4, wherein the bridge is formed from shape memory material and is configured to change in shape from a first height to a second, lower height to facilitate introduction of the bridge into a percutaneous delivery system.

8. The implant of claim 7, wherein the shape memory material is in the shape of a flattened wire.

9. The implant of claim 1, wherein the implant lock is configured to maintain the length of the outer sheath material when installed in a heart.

10. The implant of claim 9, wherein the implant lock defines at least one distal opening therein, said at least one distal opening being connected to two distally extending tubular limbs for guiding the outer sheath material therethrough.

11. The implant of claim 10, wherein a first of the tubular limbs is configured to traverse the tricuspid valve and includes an atraumatic distal tip formed thereon for distributing axially applied stress across a surface of a native septum after traversing the tricuspid valve, the first tubular limb being configured to permit the outer sheath material to pass therethrough, and further wherein a second of the tubular limbs is configured to traverse the coronary sinus and is configured to permit the outer sheath material to pass therethrough.

12. The implant of claim 11, wherein the first and second tubular limbs are each polymeric tubes preformed with a curvature of about 90 degrees along their lengths to approximate the vascular anatomy that they traverse to reduce applied thereto.

13. The implant of claim 10, wherein at least one of the limbs is an adjustable limb having an adjustable length, wherein the length of said at least one adjustable limb can be adjusted while it is being urged against native anatomy.

14. The implant of claim 10, wherein at least one of said tubular limbs includes at least one radiopaque marker disposed thereon.

15. The implant of claim 14, wherein said at least one radiopaque marker includes a plurality of markers formed along the length of said at least one tubular limb.

16. The implant of claim 1, wherein the outer sheath material has a varying transverse dimension along its length.

17. The implant of claim 16, wherein the outer sheath material has an enlarged width in a region where the bridge is present.

\* \* \* \* \*